United States Patent
Gallagher et al.

(10) Patent No.: US 8,510,055 B2
(45) Date of Patent: Aug. 13, 2013

(54) METHODS FOR CHARACTERIZING AND TREATING COGNITIVE IMPAIRMENT IN AGING AND DISEASE

(75) Inventors: Michela Gallagher, Baltimore, MD (US); Rebecca Haberman, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1007 days.

(21) Appl. No.: 11/990,049

(22) PCT Filed: Aug. 3, 2006

(86) PCT No.: PCT/US2006/030446
§ 371 (c)(1),
(2), (4) Date: Mar. 16, 2009

(87) PCT Pub. No.: WO2007/019312
PCT Pub. Date: Feb. 15, 2007

(65) Prior Publication Data
US 2010/0081648 A1    Apr. 1, 2010

Related U.S. Application Data

(60) Provisional application No. 60/705,642, filed on Aug. 3, 2005, provisional application No. 60/705,560, filed on Aug. 3, 2005, provisional application No. 60/705,559, filed on Aug. 3, 2005, provisional application No. 60/705,702, filed on Aug. 3, 2005, provisional application No. 60/705,691, filed on Aug. 3, 2005, provisional application No. 60/705,686, filed on Aug. 3, 2005, provisional application No. 60/705,700, filed on Aug. 3, 2005, provisional application No. 60/705,698, filed on Aug. 3, 2005, provisional application No. 60/705,700, filed on Aug. 3, 2005, provisional application No. 60/705,698, filed on Aug. 3, 2005, provisional application No. 60/705,662, filed on Aug. 3, 2005, provisional application No. 60/705,697, filed on Aug. 3, 2005, provisional application No. 60/705,659, filed on Aug. 3, 2005, provisional application No. 60/705,683, filed on Aug. 3, 2005, provisional application No. 60/705,699, filed on Aug. 3, 2005, provisional application No. 60/705,417, filed on Aug. 3, 2005, provisional application No. 60/705,418, filed on Aug. 3, 2005, provisional application No. 60/705,511, filed on Aug. 3, 2005, provisional application No. 60/705,701, filed on Aug. 3, 2005, provisional application No. 60/705,661, filed on Aug. 3, 2005, provisional application No. 60/705,594, filed on Aug. 3, 2005, provisional application No. 60/705,695, filed on Aug. 3, 2005, provisional application No. 60/705,512, filed on Aug. 3, 2005, provisional application No. 60/705,416, filed on Aug. 3, 2005, provisional application No. 60/705,591, filed on Aug. 3, 2005, provisional application No. 60/705,703, filed on Aug. 3, 2005.

(51) Int. Cl.
*G01N 33/48* (2006.01)
*G01N 31/00* (2006.01)
*A01N 61/00* (2006.01)

(52) U.S. Cl.
USPC ............................... 702/19; 702/22; 514/1

(58) Field of Classification Search
None
See application file for complete search history.

(56) References Cited

U.S. PATENT DOCUMENTS 7,498,361 B2    3/2009    Fogel

FOREIGN PATENT DOCUMENTS

| GB | 2 352 630 | 2/2001 |
|---|---|---|
| GB | 2 352 631 | 2/2001 |
| GB | 2 352 632 | 2/2001 |
| WO | WO 00/27849 | 5/2000 |
| WO | WO 02/40487 | 5/2002 |
| WO | WO 02/069948 | 9/2002 |
| WO | WO 03/025122 | 3/2003 |
| WO | WO 2007/018660 | 2/2007 |

OTHER PUBLICATIONS

Blalock et al., "Gene microarrays in hippocampal aging: statistical profiling identifies novel processes correlated with cognitive impairment," *The Journal of Neuroscience*, 23(9):3807-3819 (2003).
Adams et al., "Hippocampal dependent learning ability correlates with N-methyl-D-aspartate (NMDA) receptor levels in CA3 neurons of young and aged rats," J. Comp. Neurol., 432:230-243 (2001).
Albert, "The ageing brain: normal and abnormal memory," Philos. Trans. R. Soc. Lond. B. Biol. Sci., 352:1703-1709 (1997).
Barnes et al., "Region-specific age effects on AMPA sensitivity: electrophysiological evidence for loss of synaptic contacts in hippocampal field CA1," Hippocampus, 2:457-468 (1992).
Bartus et al., "The cholinergic hypothesis of geriatric memory dysfunction," Science, 17:408-414 (1982).
Baxter et al., "Neurobiological substrates of behavioral decline: models and data analytic strategies for individual differences in aging," Neurobiol. Aging, 17:491-495 (1996).
Brewer et al., "Optimized survival of hippocampal neurons in B27-supplemented Neurobasal, a new serum-free medium combination," J. Neuroscience Res. 35:567-576 (1993).

(Continued)

*Primary Examiner* — Larry D Riggs, II
(74) *Attorney, Agent, or Firm* — Ropes & Gray LLP; James F. Haley, Jr.; Yang Xu

(57) ABSTRACT

This invention provides methods for identifying genes associated with cognitive impairment and for identifying compounds useful in the treatment of cognitive impairment. The methods can in particular be used to identify genes associated with, and compounds useful in treating, cognitive impairment in aging.

3 Claims, No Drawings

(56) References Cited

OTHER PUBLICATIONS

Chambers et al., "An Orally Bioavailable, Functionally Selective Inverse Agonist at the Benzodiazepine Site of GABAA?5 Receptors with Cognition Enhancing Properties," J. Med. Chem., 47:5829-5832 (2004).

Chappell et al., "A re-examination of the role of basal forebrain cholinergic neurons in spatial working memory," Neuropharmacology, 37: 481-488, (1998).

Colombo et al., "Spatial memory is related to hippocampal subcellular concentrations of calcium-dependent protein kinase C isoforms in young and aged rats," Proc. Natl. Acad. Sci. USA, 94:14195-14199 (1997).

Folstein et al., ""Mini-mental state". A practical method for grading the cognitive state of patients for the clinician," J Psychiatric Res., 12:189-198 (1975).

Gallagher et al., "Relationship of age-related decline across several behavioral domains," Neurobiol. Aging, 10:691-708 (1989).

Gallagher et al., "Severity of spatial learning impairment in aging: development of a learning index for performance in the Morris water maze," Behav. Neurosci., 107:618-626 (1993).

Gallagher, "Animal models of memory impairment," Philos. Trans. R. Soc. Lond. B. Biol. Sci., 352:1711-1717 (1997).

Jarrard, "On the role of the hippocampus in learning and memory in the rat," Behav. Neural. Biol. 60(1):9-26 (1993).

Kluger et al., "Neuropsychological prediction of decline to dementia in nondemented elderly," J Geriatr Psychiatry Neurol., 12:168-179 (1999).

Lein et al., "Defining a molecular atlas of the hippocampus using DNA microarrays and high-throughput in situ hybridization," J Neurosci., 24:3879-3889 (2004).

Morris, Learning and Motivation 12:239-260 (1981).

Petersen et al., "Mild cognitive impairment: clinical characterization and outcome," Arch. Neurol., 56: 303-308 (1999).

Platt et al., "Contribution of alpha 1GABAA and alpha 5GABAA receptor subtypes to the discriminative stimulus effects of ethanol in squirrel monkeys," J. Pharmacol. Exp. Ther., 313:658-667 (2005).

Qin et al., Evaluation of methods for oligonucleotide array data via quantitative real-time PCR. BMC Bioinformatics, 7:23 (2006).

Rapp et al., "Memory systems in normal and pathological aging," Curr. Opin. Neurol., 7:294-298 (1994).

Robbins et al., "Cambridge Neuropsychological Test Automated Battery (CANTAB): a factor analytic study of a large sample of normal elderly volunteers," Dementia, 5:266-281 (1994).

Small et al., "Imaging correlates of brain function in monkeys and rats isolates a hippocampal subregion differentially vulnerable to aging," Proc. Natl. Acad. Sci. USA., 101:7181-7186 (2004).

Smith et al., "Circuit-specific alterations in hippocampal synaptophysin immunoreactivity predict spatial learning impairment in aged rats," J. Neurosci., 20:6587-6593 (2000).

Sternfeld, et al., "Selective, orally active gamma-aminobutyric acidA alpha5 receptor inverse agonists as cognition enhancers,", J. Med. Chem., 47:2176-2179 (2004).

Szekeres et al., "3,4-Dihydronaphthalen-1(2H)-ones: novel ligands for the benzodiazepine site of alpha5-containing GABAA receptors," Bioorg. Med. Chem. Lett., 14:2871-2875 (2004).

Walsh et al., "Ionic currents in cultured rat suprachiasmatic neurons," Neuroscience, 69:915-929 (1995).

Whitehouse et al., "Alzheimer's disease and senile dementia: loss of neurons in the basal forebrain," Science, 215:1237-39 (1982).

Wu et al., "A Model Based Background Adjustment for Oligonucleotide Expression Arrays," Journal of American Statistical Association, 99:909-917 (2004).

Zoran et al., "Specific muscle contacts induce increased transmitter release and neuritic arborization in motoneuronal cultures," Dev Biol., 179:212-22 (1996).

Chambers et al., "Identification of a novel, selective $GABA_A$ $\alpha 5$ receptor inverse agonist which enhances cognition," J. Med. Chem., 46:2227-2240 (2003).

Berton et al., "Acamprosate Enhances N-Methyl-D-Apartate Receptor-Mediated Neurotransmission But Inhibits Presynaptic $GABA_B$ Receptors in Nucleus Accumbens Neurons," *Alcohol Clin Exp Res*, Feb. 1998, 22(1): 183-191.

Reilly et al., "Effects of Acamprosate on Neuronal Receptors and Ion Channels Expressed in *Xenopus* Oocytes," *Alcohol Clin Exp Res*, Feb. 2008, 32(2): 188-196.

Wisden et al., "The Distribution of 13 $GABA_A$ Receptor Subunit mRNAs in the Rat Brain. I. Telencephalon, Diencephalon, Mesencephalon," *The Journal of Neuroscience*, Mar. 1992, 12(3): 1040-1062.

METHODS FOR CHARACTERIZING AND TREATING COGNITIVE IMPAIRMENT IN AGING AND DISEASE

BACKGROUND OF THE INVENTION

A major focus of the field of aging and dementia is the investigation of the causes of cognitive impairment. Various conditions, such as dementias (e.g., Alzheimer's Disease, Lewy body dementia, vascular dementia, and HIV associated dementia), neurodegenerative diseases (e.g., Huntington's Disease, Parkinson's Disease, amyotrophic lateral sclerosis), neurological disorders (e.g., schizophrenia, depression), and age-related conditions (e.g., Mild Cognitive Impairment, Age-Related Cognitive Decline), are associated with cognitive impairment. As the understanding of cognitive impairment increases, so does the need to develop sensitive methods to both detect and to treat such impairment.

Accumulating evidence suggests that there is a neurogenetic component to cognitive impairment. For example, changes in the mammalian brain appear to parallel alterations in distinct learning and memory processes. See, e.g., Albert, *Philos. Trans. R. Soc. Lond. B. Biol. Sci.* 352(1362):1703-09 (1997). In particular, alterations in the hippocampal formation are among the most prominent and consistent features observed in age-related cognitive impairment. Gallagher, *Philos. Trans. R. Soc. Lond. B. Biol. Sci.* 352(1362):1711-7 (1997). Changes in the aged hippocampus also parallel, to some extent, the hippocampal changes observed in other conditions associated with cognitive impairment, such as Alzheimer's Disease. Whitehouse et al., *Science.* 215(4537):1237-39 (1982); Bartus et al., *Science.* 17(4558):408-14 (1982); Rapp and Heindel, *Curr. Opin. Neurol.* 7(4):294-8 (1994). Thus, the effects of aging on hippocampal function may be related at some level to disease processes in progressive neurodegenerative illnesses.

The mammalian hippocampus is a structure that contains distinct populations of neurons organized into separate anatomical subregions. These subregions include, for example, the dentate gyrus (DG) and the Cornu Ammonis (CA) subfields CA1 and CA3. Each hippocampal subregion is characterized by a unique molecular profile. Lein et al. *J. Neurosci.* 24(15):3879-89 (2004). These different profiles may account for the differential vulnerability of these regions to various mechanisms of cognitive impairment. See, e.g., Small et al. *Proc. Natl. Acad. Sci. USA.* 101(18):7181-6 (2004).

Considerable research has examined the correlation between changes in cognitive function and neuronal changes in specific hippocampal subregions. This research suggests that the specific nature and extent of hippocampal damage parallels in some cases the degree and type of cognitive impairment. See, Jarrard, *Behav. Neural. Biol.* 60(1):9-26 (1993). For example, synaptic alterations specific to the CA1 region correlate with age-related impairments in cellular responsiveness to glutamate receptor stimulation. Barnes et al., *Hippocampus.* 2(4):457-68 (1992). Likewise, individual differences in spatial learning ability correlate with expression levels of NR1, an N-methyl-D-Aspartate (NMDA) receptor subunit, selectively in CA3 neurons. Adams et al., *J. Comp. Neurol.* 432(2):230-43 (2001). And, levels of synaptic markers in the DG correlate with individual levels of cognitive impairment in spatial learning capacity among aged rats. Smith et al., *J. Neurosci.* 20(17):6587-93 (2000). These correlations do not, however, establish that the neuronal changes cause the observed functional changes. Just as, importantly, changes in the hippocampus and cognitive function do not occur solely as a result of aging per se. Thus, comparisons based on chronological age alone often fail to capture the hippocampal changes that correlate with individual levels of cognitive impairment.

Although some impairment in both cognitive function and hippocampal integrity may be a normal consequence of healthy aging, a significant population of elderly adults experiences a decline in cognitive ability that exceeds normal development. Thus, the effect of aging itself on cognition, in the absence of dementia or disease, is important for defining the boundary between illness and normal aging.

Heterogeneous patterns of progressive cognitive impairment are characteristic of mammalian test populations, e.g., aged humans and aged laboratory animals. The increasing preponderance of 'individual differences' in cognitive impairment has been used to characterize normal mammalian aging itself. Baxter and Gallagher, *Neurobiol. Aging.* 17(3):491-95 (1996).

There is, therefore, a need to elucidate the molecular basis of and to treat cognitive impairment, both in aging and in disease. There is also a need to understand the neurogenetic components of cognitive impairment and to develop a range of treatment options for individuals with varying levels of impaired cognition.

The examination of changes in expressed gene products in the hippocampus of the mammalian brain, as described in this invention, may serve to elucidate the genetic or molecular basis of cognitive impairment. Moreover, the examination of changes in expressed gene products in the aged hippocampus may serve to elucidate the genetic or molecular basis of cognitive impairment in aging. The identification of genes, or a plurality of genes, that are associated with cognitive impairment, and particularly that are associated with age-related cognitive impairment, would also allow the identification of compounds for treating such impairment.

SUMMARY OF THE INVENTION

This invention provides methods for identifying genes and their expressed gene products, e.g., RNAs, polypeptides, peptides and proteins, associated with cognitive impairment and for identifying compounds useful in the treatment of cognitive impairment. The methods of this invention can, in particular, be used to identify genes and expressed gene products associated with and compounds useful in treating cognitive impairment in aging.

This invention provides a method of identifying a gene or a plurality of genes associated with cognitive impairment by determining the abundance of expressed gene products in one or more of CA1, CA3 and DG hippocampal tissue of mammals in a population of aged mammals with cognitive impairment (aged impaired or "AI"), aged mammals without cognitive impairment (aged unimpaired or "AU") and young mammals ("Y"), and selecting the genes based on a significant change—increase or decrease—in the relative abundance of the gene's expressed gene product in the AI population relative to the combined AU and Y populations or based on a significant change—increase or decrease—in the relative abundance of the gene's expressed gene product in the AU population relative to the combined AI and Y populations. The AI genes and their expressed gene products may be related to and markers of cognitive impairment and unhealthy aging. Conversely the AU genes and their expressed genes products may be related to and markers of adaptive aging to preserve and protect cognitive function.

One preferred gene in accordance with this invention, the abundance of whose expressed gene product in the AI population relative to the expressed gene product in the combined AU and Y populations is decreased is the GABA-A α5 receptor gene (corresponding to GENBANK® accession number NM_017295), as shown in Example 36 and Table 36 (CA3 AI ANOVA decrease) and its homologues.

This invention provides a method of correlating the changed abundance—increase or decrease—of a selected gene's or its homologue's expressed gene product with the level of cognitive impairment or age-related cognitive impairment in each mammal of the AU and AI populations and selecting one or more genes, the changed abundance—increase or decrease—of whose expressed gene product(s) significantly correlates with the level of cognitive impairment or age-related cognitive impairment in the mammal. Preferably, one gene whose decreased expressed gene product significantly correlates with the level of cognitive impairment is the GABA-A α5 receptor gene (corresponding to GENBANK® accession number NM_017295), as shown in Example 10 and Table 10 (CA3 AI ANOVA negative correlation).

This invention also provides methods for identifying compounds useful for treating cognitive impairment by determining the abundance or function, either in a mammalian cell or in the hippocampus of a mammal, of the expressed gene product of at least one gene, identified by the above methods of the invention, or listed in Tables 1-48, or their homologues, in the presence or absence of a candidate compound and identifying a compound from among the candidate compounds that significantly changes that abundance or alters the function of those genes or expressed gene products in the appropriate direction as defined herein, either in the mammalian cell or in the hippocampus of the mammal, preferably in the CA1, CA3 or DG hippocampal tissue from which the gene was identified, to whom the candidate compound is administered. The same method may also be used for identifying compounds useful in treating age-related cognitive impairment by testing the candidate compounds in aged mammals. Preferably, compounds useful for treating cognitive impairment are (1) the GABA-A α5 receptor agonist QH-ii-066 (1-methyl-7-acetyleno-5-phenyl-1,3-dihydro-benzo[e]-1,4-diazepin-2-one), see, Platt et al., Contribution of $_{\alpha 1}GABA_A$ and $_{\alpha 5}GABA_A$ Receptor Subtypes to the Discriminative Stimulus Effects of Ethanol in Squirrel Monkeys, *J. Pharmacol. Exp. Ther.* 313: 658-667 (2005); (2) 6,6 dimethyl-3-(3-hydroxypropyl)thio-1-(thiazol-2-yl)-6,7-dihydro-2-benzothiophen-4(5H)-one, corresponding to compound number 44 in Chambers et al., Identification of a Novel, Selective $GABA_A$ α5 Receptor Inverse Agonist Which Enhances Cognition, *J. Med. Chem.* 46:2227-2240 (2003); and (3) 8-ethylthio-3-methyl-5-(1-oxidopyridin-2-yl)-3,4-dihydronaphthalen-1(2H)-one, corresponding to compound number 19 in Szekeres et al., 3,4-Dihydronaphthalen-1(2H)-ones: novel ligands for the benzodiazepine site of alpha5-containing GABAA receptors. *Bioorg. Med. Chem. Lett.* 14:2871-2875 (2004).

This invention provides methods for identifying a compound useful in the treatment of cognitive impairment by determining the cognitive status of a mammal in the presence or absence of a candidate compound believed to change the abundance of the expressed gene product of at least one gene, identified by the method of this invention, or listed in Tables 1-48, or their homologues, or to alter the function of those genes or expressed gene products in the appropriate direction, as defined herein, and identifying a compound from among the candidate compounds that beneficially alters the cognitive status of the mammal. The same method may also be used to identify compounds useful for treating age-related cognitive impairment by testing candidate compounds in aged mammals.

DETAILED DESCRIPTION OF THE INVENTION

Unless otherwise defined herein, scientific and technical terms used in this application shall have the meanings that are commonly understood by those of ordinary skill in the art. Further, unless otherwise required by context, singular terms include pluralities and plural terms include the singular. Generally, nomenclatures used in connection with, and techniques of, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present invention are generally performed, unless otherwise indicated, according to conventional methods well known in the art and as described in various general and more specific references that are cited and discussed throughout the present specification. See, e.g. Ausubel et al., "Current Protocols in Molecular Biology", Greene Publishing Associates (1992, and Supplements to 2003); Cooper and Hausman, "The Cell—A Molecular Approach, 2nd ed.", Sinauer Associates, Inc., Sunderland, Mass. (2000); Kandel et al., "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); Gilbert et al., "Developmental Biology, 6th ed.", Sinauer Associates, Inc., Sunderland, Mass. (2000); Sambrook et al., "Molecular Cloning: A Laboratory Manual, 2d ed.", Cold Spring Harbor Laboratory Press, Cold Spring Harbor, N.Y. (1989).

Chemistry terms used herein are used according to conventional usage in the art, as exemplified by "The McGraw-Hill Dictionary of Chemical Terms", Parker S., Ed., McGraw-Hill, San Francisco, Calif. (1985).

All of the above, and any other publications, patents and published patent applications, referred to in this application are specifically incorporated by reference herein. In case of conflict, the present specification, including its specific definitions, will control.

The Specific Terms Used in the Methods of this Invention

The following terms, unless otherwise indicated, shall be understood to have the following meanings.

"Abundance" refers to the level of expression, activity or amount of an expressed gene product of a gene or its homologue from another organism. The abundance of an expressed gene product includes, but is not limited to, the level of expression of the function that the gene performs and the way in which it does so, including chemical or structural differences and/or differences in binding or association with other factors. It also includes the amount of the product whatever its source, e.g., expression or direct addition to the tissue, cell or animal. Abundance can be detected by any method useful in quantitatively measuring the expressed gene product. These include, for example, enzymatic assays, binding assays, immunoassays, structural and chemical assays (e.g., which measure modifications such as phosphorylation status, conformational changes).

The methods for measuring the abundance of an expressed gene product according to this invention include, but are not limited to, microarray analysis, macroarray analysis, in situ hybridization histochemistry, fluorescent in situ hybridization (FISH), immunocytochemistry (ICC), immunofluorescence, enzyme linked immunosorbent assay (ELISA), fluorescence polarization immunoassay (FPIA), nephelometric inhibition immunoassay (NIA), immunoprecipitation, quantitative polymerase chain reaction (PCR), RNase protection assay, reverse-transcription PCR, competitive PCR, real-time quantitative PCR (i.e., TagMan PCR), serial analysis of gene expression (SAGE) analysis, two-dimensional gel electrophoresis, mass spectrometry, MALDI-TOF mass spectrometry, radioimmunoassay (RIA) and blot analysis (e.g. Northern blot, Western blot, protein slot blot, immunoblot, dot blot). If desired, any of the expression and activity assays described above can be used in combination, either sequentially or simultaneously. Such assays can also be partially or completely automated, using methods known in the art.

"Aged" refers to a mammal advanced in years, preferably in or near the latter third of their average lifespan. For example, an aged human would be fifty or more years of age. An aged rat would be fifteen months of age or more.

"Age-related cognitive decline" or "ARCD", or an equivalent construct such as "age-associated memory impairment", refers to a diagnosis of mild memory deficit that is not expected to worsen considerably over time. As used herein, ARCD can also be defined as Stage 2 on the Global Deterioration Scale (GDS). The GDS is a seven-point rating system of cognitive and functional capabilities. It is widely used for rating cognitive performance in older adults, with scores ranging from normal aging (Stage 1) to severe dementia (Stage 7). Stage 2 is characterized, for example, by the following clinical characteristics: subjective cognitive complaints in the absence of clinically manifest deficit.

"AI" or "aged impaired" refers to one or more aged mammals with cognitive impairment relative to young mammals of the same species. The preferred species used as models of age impairment in this invention is rats. Most preferably, the rat is from an outbred strain. Aged rats naturally segregate into two populations, with about half of the aged rats being AI and about half being aged unimpaired (AU). To identify these populations, the cognitive ability of young and aged rats is measured. Methods for identifying populations of AI rats are known in the art, e.g., Gallagher and Burwell, *Neurobiol. Aging* 10:691-708 (1989) and an exemplary method is described in the Example. A number of methods for assessing rat cognitive ability are also known, e.g., the Barnes circular maze, the radial arm maze, the Morris water maze, delayed alternation (delayed nonmatch-to-sample), novel object recognition, conditioned avoidance, and fear conditioning.

"ANOVA" or "analysis of variance" refers to a statistical technique broadly applicable for analyzing data. An ANOVA compares the distribution of two or more populations to determine if one or more of the populations are significantly different from the others. The average variance within each of the populations is factored out from the variance between each of the populations before computing the probability of significant differences between the populations. When an ANOVA tests the difference between the means of two (and not more) populations, it is equivalent to a t-test. As used herein, for example, ANOVA is used to test the hypothesis that the abundance of an expressed gene product of a gene or a plurality of genes is different in mammals with cognitive impairment (e.g., the AI population) relative to mammals without cognitive impairment (e.g., the combined AU and Y populations), by computing the probability that significant differences among populations or treatments are too large to be due to chance.

The statistic calculated by an ANOVA is an F-ratio, which reveals the significance of the hypothesis that Y depends on X. It comprises the ratio of two mean-squares: $MS[X]/MS[\epsilon]$, which is the sum of squared deviations from the mean X or c divided by the appropriate degrees of freedom. One of skill in the art would use standard tables to determine whether the observed F-ratio indicates a significant relationship. When there are two groups, the F-ratio is equivalent to the t as determined by a t-test. As used herein, when the mean abundance of an expressed gene product of a gene or a plurality of genes is being compared between two groups (e.g., between Aged Impaired and Aged Unimpaired with Young) by ANOVA, the F-ratio would be equivalent to the t test statistic, as determined by a t-test.

A "MAS5" statistical analysis produces absolute and comparison analysis results for microarrays and preferably GeneChip microarrays. It is an algorithm for deriving gene expression scores from microarrays based on present or absent calls, where a percentage of transcripts that are considered significantly hybridized to the chip are considered present. The MAS5 analysis also comprises an algorithm, not used in the present invention, that can deduce present, absent and also marginal calls.

A "gcRMA" statistical analysis is another algorithm for deriving gene expression scores from microarrays and preferably GeneChip microarrays. It is an open-source method that is based on robust averaging techniques and sequence-dependent affinity corrections. The robust averaging employed in gcRMA confers a strong immunity to outliers.

"Appropriate direction" refers to the direction of the change in the abundance of the expressed gene product(s) of at least one gene identified by the methods of this invention or listed in Tables 1-48 or their homologues or the change in the function of the gene or expressed gene product. For genes, whose gene products increase in the AI population relative to the combined AU and Y populations, the "appropriate direction" is a decrease or attenuation of function. For genes, whose gene products decrease in the AI population relative to the combined AU and Y population, the "appropriate direction" is an increase or enhancement in function. For genes, whose gene products increase in the AU population relative to the combined AI and Y populations, the "appropriate direction" is an increase or enhancement of function. And, for genes, whose gene products decrease in the AU population relative to the combined AI and Y populations, the "appropriate direction" is a decrease.

"AU" or "aged unimpaired" refers to one or more aged mammals without cognitive impairment relative to young mammals of the same species. The preferred species used as models of age impairment in this invention is rats. Most preferably, the rat is from an outbred strain. As noted above, aged rats naturally segregate into two populations, with about half of the aged rats being AI and about half being AU. To identify these populations, the cognitive ability of young and aged rats can be measured. Methods for identifying populations of AU rats are known in the art, e.g., Gallagher and Burwell, *Neurobiol. Aging* 10:691-708 (1989), and an exemplary method is described in the Example. A number of methods for assessing rat cognitive ability are known, e.g., the Barnes circular maze, the radial arm maze, the Morris water maze, delayed alternation (delayed nonmatch-to-sample), novel object recognition, conditioned avoidance, and fear conditioning.

"Beneficially alters" refers to the state of promoting, improving, or preserving cognitive function, or of alleviating or attenuating cognitive decline. A beneficial alteration in accordance with this invention also includes the alleviation or amelioration of one or more manifestations of cognitive impairment, or the delay of onset or slowing of the progression of cognitive impairment. A beneficial alteration of this invention includes, but is not limited to, a change in cognitive function sufficient to result in an improved score in a test of cognitive function; the improvement of cognitive function in a subject with impaired cognitive function so that it more closely resembles the function of a control subject, preferably, e.g., a young subject or an aged unimpaired subject; the improvement over an aged cognitively impaired subject or population; and the preservation of cognitive function over time such that it does not decline or fall below the level observed in the subject upon first presentation or diagnosis.

"Candidate compound" or "compound" means a pharmaceutical, chemical or other composition of matter with known or unknown physiological effects. A compound can be any natural or synthetic agent made up of one or more elements, including, but not limited to, a small molecule, peptide, polypeptide, peptidomimetic, carbohydrate, lipid, protein, glycoprotein, lipoprotein, nucleic acid, and antibody. A compound may or may not have been characterized for its target, or mode of action, in cells or animals prior to its use in the methods of this invention.

As used herein, the compound that is identified and selected from among one or more candidate compounds as being useful in treating cognitive impairment refers to a compound that is capable of altering the abundance—increase or decrease—of the expressed gene product of at least one gene identified in accordance with this invention, one or more genes listed in Tables 1-48, or their homologues in the appropriate direction, as defined herein, i.e., in a manner consistent with the beneficial treatment of cognitive function or that is capable of beneficially altering the cognitive status of a mammal to whom it is administered. Preferably, the compound crosses the blood-brain barrier. More preferably, the compound is orally bioavailable.

"Cognitive function" or "cognitive status" refers to any higher order intellectual brain process or brain state, respectively, involved in learning and memory including, but not limited to, attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behavior, and expressing an interest in one's surroundings and self-care.

"Cognitive impairment" or "CI" or an equivalent construct, such as "impaired cognitive function" or "cognitive decline", refers to a deficit or reduction in cognitive status or cognitive function, as defined above, compared to that same function in an age-matched control subject or more usually a population. Cognitive impairment may be observed as a consequence of aging, as well as in various diseases and conditions, including but not limited to, Alzheimer's Disease, Lewy body dementia, vascular dementia, HIV associated dementia, Huntington's Disease, Parkinson's Disease, amyotrophic lateral sclerosis, schizophrenia, depression, MC1, and ARCD.

"Expressed gene product" refers to any form of expression of a gene that can be detected and measured, for example, RNA, amino acid, peptide, polypeptide or protein. It also includes the product itself, whether or not it was actually derived from expression in the cell or tissues of an animal.

"Hippocampal-dependent function" refers to a cognitive function, more specifically a learning or memory process, that includes the encoding and acquisition of memories for specific facts and events and episodes of experiences. Hippocampal-dependent function includes the processing of memory representations and the maintenance of memories. Hippocampal-dependent function in mammals includes, for example, spatial memory acquisition, long-term spatial memory, and spatial memory retrieval. A mammal with impaired hippocampal-dependent function may display, e.g., anterograde amnesia for newly acquired facts and events, including maze-specific information in a spatial water maze.

"Hippocampal formation" or "hippocampus" or "hippocampal tissue" refers to the whole or part of the hemispheric structure in the brain folded into the ventromedial surface of the temporal lobe, caudal to the amygdaloid complex. Hippocampal tissue comprises hippocampal cells from, without limitation, the CA1, CA3 and DG subregions. Hippocampal cells include, but are not limited to, pyramidal cells of the CA subregions and granule cells of the DG subregion.

"Homologue" refers to a gene that has the same origin and functions in two or more species. Preferably, a mammal's homologue of a gene, as identified by the method of the invention, refers to the mammal's equivalent of a gene identified in another mammalian species, e.g., the genes encoding human and rat growth hormones.

"Level of cognitive impairment" refers to a measure of the degree of cognitive impairment observed in a mammal. In humans, the level of cognitive impairment may be measured by various neuropsychological tests, alone or in combination, including, but not limited to, the Alzheimer's Disease Assessment Scale-cognitive subscale (ADAS-cog); Global Deterioration Scale (GDS); the clinical global impression of change scale (CIBIC-plus scale); the Alzheimer's Disease Cooperative Study Activities of Daily Living Scale (ADCS-ADL); the Mini Mental State Exam (MMSE); the Neuropsychiatric Inventory (NPI); the Clinical Dementia Rating Scale (CDR); the Rey Auditory Verbal Learning Test (AVLT), Logical Memory Subtest of the revised Wechsler Memory Scale (WMS-R); the New York University (NYU) Paragraph Recall Test the Cambridge Neuropsychological Test Automated Battery (CANTAB) or the Sandoz Clinical Assessment-Geriatric (SCAG).

In non-human mammalian models, for example, a rat or non-human primate model, the level of cognitive function may be measured by methods including, but not limited to, using a maze in which subjects use spatial information (e.g., Morris water maze, Barnes circular maze, elevated radial arm maze, elevated plus maze, T-maze and others), recognition tests using odor and novel objects, conditioning tests (e.g., fear conditioning, discrimination tasks, active avoidance, illuminated open-field, two-compartment exploratory test, second and third order conditioning tasks), and tests of higher level executive function (e.g., serial reaction time tests, delayed match and non-match to sample, and stimulus-reward associations including choices involving delayed reinforcement).

In addition, the level of cognitive function may be measured in mammals, including humans, using neuroimaging techniques, e.g., Positron Emission Tomography (PET), magnetic resonance imaging (MRI), functional magnetic resonance imaging (fMRI), Single Photon Emission Computed Tomography (SPECT), or any other imaging technique that allows one to measure brain function. The level of cognitive function in aging can be tested by any of the above methods using aged mammals.

"Microarray" or "macroarray" refers to an array (i.e. a matrix) that consist of a surface to which probes (e.g., cDNAs, mRNAs, oligonucleotides, peptides, polypeptides, proteins, antibodies or their equivalents) that correspond or are complementary to in sequence or bind to expressed gene products are bound at known or addressable positions. Each position represents a discrete binding site, e.g., a nucleic acid or nucleic acid analogue, to which a particular expressed gene product can specifically bind. Each array typically, but not necessarily, possesses binding sites for products of most or almost all of the expressed gene products in the mammal's genome. It may also be a representative of such genome. A microarray has a higher density of individual probe species or binding sites per area than a macroarray. A nucleic acid or analogue of a binding site can be, e.g., a synthetic oligomer, a full-length cDNA, a less-than full-length cDNA, an expressed sequence tag (EST) as part of a cDNA molecule, or a gene fragment, e.g., an oligonucleotide corresponding to an overlapping portion of a gene. Preferably, oligonucleotide probes are used. Most preferably, the Affymetrix RAT genome 230-2 array (or an equivalent) is used. The RAT genome 230-2 array contains more than 31,000 probe sets to transcripts from approximately 28,000 genes.

"Mild Cognitive Impairment" or "MCI" refers to a condition characterized by isolated memory impairment accompanied by no other cognitive abnormality and relatively normal functional abilities. One set of criteria for a clinical characterization of MCI specifies the following characteristics: (1) memory complaint (as reported by patient, informant, or physician), (2) normal activities of daily living (ADLs), (3) normal global cognitive function, (4) abnormal memory for age (defined as scoring more than 1.5 standard deviations below the mean for a given age), and (5) absence of indicators of dementia (as defined by DSM-IV guidelines). Petersen et al., *Srch. Neurol.* 56: 303-308 (1999); Petersen, "Mild cognitive impairment: Aging to Alzheimer's Disease." Oxford University Press, N.Y. (2003).

Diagnosis of MCI usually entails an objective assessment of cognitive impairment, which can be garnered through the use of well-established neuropsychological tests, including the Mini Mental State Examination (MMSE), the Cambridge Neuropsychological Test Automated Battery (CANTAB) and individual tests such as Rey Auditory Verbal Learning Test (AVLT), Logical Memory Subtest of the revised Wechsler Memory Scale (WMS-R) and the New York University (NYU) Paragraph Recall Test. See Folstein et al., *J Psychiatric Res* 12: 189-98 (1975); Robbins et al., *Dementia* 5: 266-81 (1994); Kluger et al., *J Geriatr Psychiatry Neurol* 12:168-79 (1999).

"Non-human animal model" refers to a non-human mammal or other animal or organism useful for research.

"Non-parametric test" refers to a statistical test that does not rely on parametric assumptions such as normality. A non-parametric test is used in place of a parametric test when some assumptions about the underlying population are uncertain. In the present invention, a non-parametric test is used when the test or control population is sampled from a non-Gaussian distribution or when a gene's expressed gene product is too high or too low in abundance to be accurately determined.

One of skill in the art would appreciate that non-parametric tests rank the outcome variable from low to high and then analyze the ranks. Preferably, the non-parametric test used for comparing populations in accordance with this invention is selected from the group consisting of a Mann-Whitney U test, a Wilcoxon rank-sum test, a Wilcoxon matched pairs signed-rank test, a Mann-Whitney-Wilcoxon test, a Kruskal-Wallis analysis of variance by ranks, a Friedman two way analysis of variance and a Kolmogorov-Smirnov test. Preferably, the non-parametric test used for assessing the linear association (i.e. correlation) between variables is the Spearman rank correlation coefficient.

"Overexpressed", "overexpression" or "increase" in expression refers to an abundance of an expressed gene product that is higher than the abundance of that same product under other conditions or in other cells or tissues. Overexpression or increased expression may be effected, for example, by one or more structural changes to the gene's encoding nucleic acid or encoded polypeptide sequence (e.g., primary nucleotide or amino acid changes or post-transcriptional modifications such as phosphorylation), altered gene regulation (e.g., in the promoters, regulators, repressors or chromatin structure of the gene), a chemical modification, an altered association with itself or another cellular component, an altered subcellular localization, a modification which causes higher levels of activity through association with other molecules in the cell (e.g., attachment of a targeting domain) and the like.

"Parametric test" refers to a statistical test that requires a parametric assumption, such as normality, i.e., the assumption that the data are sampled from a Gaussian distribution. Preferably, the parametric test, used when comparing levels of expression across populations, in accordance with this invention, is an analysis of variance (ANOVA). Preferably, the parametric test used for assessing the linear association (i.e. correlation) between variables is the Pearson correlation coefficient.

"P value" is the probability associated with an obtained statistic, such as an F-ratio or at statistic (see "ANOVA", infra). If the p value is less than the significance level, preferably 0.05, then the result constitutes evidence against the null hypothesis, which states that there is no difference among a set of true population means.

"Plurality" refers to two or more.

"Significant" refers to a confidence level for a measurement being real as opposed to being due to chance, for example, as the result of a random sampling error. In accordance with this invention, significant means a confidence or significance level of at least 95%, wherein $p<0.05$. More preferably, a significance level of 99%, wherein $p<0.01$.

"Treatment" refers to the use of a compound to beneficially alter cognitive function in the treated mammal. A treatment, as used herein, is administered by providing a mammal with a compound by any appropriate means and in any appropriate formulation and dosing regime.

"Underexpressed", "underexpression" or "decrease" in expression refers to an abundance of an expressed gene product that is lower than the abundance of the same product under other conditions or in other cells or tissues. Such underexpression or decreased expression may be effected, for example, by one or more structural changes to the gene's encoding nucleic acid or polypeptide sequence (e.g., primary nucleotide or amino acid changes or post-transcriptional modifications such as phosphorylation), altered gene regulation (e.g., in the promoters, regulators, repressors or chromatin structure of the gene), an altered structure (which causes reduced levels of activity), an altered association with itself or another cellular component, an altered subcellular localization, a modification which causes reduced levels of activity through association with other molecules in the cell (e.g., binding proteins which inhibit activity or sequestration) and the like.

"Young" or "Y" refers to one or more adolescent or adult mammals in or near the first third of their average lifespan, at or after the age of sexual maturity and when the hippocampus is fully mature. For example, a young human would be twenty-five years of age or less. A young rat would be ten months of age or less, and preferably at least four months of age.

Description of Various Claims of the Invention

This invention provides methods of identifying a gene or a plurality of genes associated with cognitive impairment in a mammal.

The method comprises providing three populations of mammals—AI, AU and Y—as defined above. Preferably, the mammals used in identifying the genes of this invention are rats and most preferably outbred rat strains.

CA1, CA3 and DG hippocampal tissue is prepared from each member of the three populations using conventional techniques. The abundance of the expressed gene products in each member of these populations is then determined using standard techniques. These techniques include microarray analysis, macroarray analysis, in situ hybridization histochemistry, fluorescent in situ hybridization (FISH), immunocytochemistry (ICC), enzyme linked immunosorbent assay (ELISA), immunoprecipitation, quantitative polymerase chain reaction (PCR), serial analysis of gene expression (SAGE) analysis, radioimmunoassay (RIA) and blot analysis. More preferably, microarray analysis is used.

Genes or a plurality of genes are then selected based on a significant change—decrease or increase—in the gene's expressed gene product (e.g., RNAs, proteins, polypeptides and peptides) in the AI population relative to the combined AU and Y populations or in the AU population relative to the combined AI and Y populations.

The significance of the change in the abundance of the expressed gene product is assessed using conventional statistical tests, including parametric and non-parametric tests. Preferably, the parametric test, ANOVA is used. Among the preferred non-parametric tests useful in this invention are a Mann-Whitney U test, a Wilcoxon rank-sum test, a Wilcoxon matched pairs signed-rank test, a Mann-Whitney-Wilcoxon test, a Kruskal-Wallis analysis of variance by ranks, a Friedman two way analysis of variance, and a Kolmogorov-Smirnov test.

The preferred selected genes or plurality of genes whose expressed gene products have increased abundances in CA1, CA3 or DG tissue are displayed in Tables 1, 3, 6, 7, 25, 27, 30, and 31; 9, 11, 14, 15, 33, 35, 38 and 39; or 17, 19, 22, 23, 41, 43, 46 and 47, respectively. Tables 1, 3, 9, 11, 17, 19, 25, 27, 33, 35, 41 and 43 depict the genes whose expressed gene products are increased in the AI populations relative to the combined AU and Y populations. Tables 6, 7, 14, 15, 22, 23, 30, 31, 38, 39, 46 and 47 depict the genes whose expressed gene products are increased in the AU population relative to the combined AI and Y populations.

The preferred selected genes or plurality of genes whose expressed gene products have decreased abundances in CA1, CA3 or DG tissue are displayed in Tables 2, 4, 5, 8, 26, 28, 29 and 32; 10, 12, 13, 16, 34, 36, 37 and 40; or 18, 20, 21, 24, 42, 44, 45 and 48, respectively. Tables 5, 8, 13, 16, 21, 24, 29, 32, 37, 40, 45 and 48 depict the genes whose expressed gene products are decreased in the AI population relative to the combined AU and Y populations. Tables _____ depict the genes whose expressed gene products are decreased in the AU population relative to the combined AI and Y populations.

In some elements of this invention, the change in the abundance—increase or decrease—of the expressed gene product(s) of the selected gene or plurality of genes is also correlated with the level of cognitive impairment in each member of the AU and AI populations. The increased or decreased abundances of the expressed gene products of the selected genes or plurality of genes positively or negatively, respectively, correlate with the learning index or cognitive impairment of the animals when poorer learners have higher or lower abundances, respectively. Thus, some of the genes in the above Tables, which depict the genes whose expressed gene products are increased in the AI population relative to the combined AU and Y populations or in the AU population relative to the combined AI and Y populations, will positively and negatively correlate, respectively, with cognitive impairment. See, e.g., Tables 1, 6, 9, 14, 17, 22, 25, 30, 33, 38, 41 and 46. Other genes whose expressed gene products are decreased in the AI population relative to the combined AU and Y populations or in the AU population relative to the combined AI and Y populations, will negatively or positively, correlate, respectively, with cognitive impairment. See, e.g., Tables 2, 5, 10, 13, 18, 21, 26, 29, 34, 37, 42 and 45.

A gene or a plurality of genes whose abundances of expressed gene product(s) have a significant positive or negative correlation with the learning index or level of cognitive impairment is then selected. The significance of the correlation is assessed using standard methods, including but not limited to parametric and non-parametric statistical tests. Preferably, the parametric Pearson correlation coefficient or the non-parametric Spearman ranked coefficient is used.

The preferred selected genes or plurality of genes, whose expressed gene products have increased abundances in CA1, CA3 or DG tissue and whose abundances positively or negatively, respectively correlate with the learning scores or cognitive impairment of the AI and AU outbred rat populations, are displayed in Tables 1, 6, 25 and 30; 9, 14, 33, 38; and 17, 22, 41 and 46, respectively.

The preferred selected genes or plurality of genes whose expressed gene products have decreased abundances in CA1, CA3 and DG tissue and whose abundances negatively or positively, respectively correlate with the learning scores or cognitive impairment of the AI and AU outbred rat populations are displayed in Tables 2, 5, 26 and 29; 10, 13, 34 and 37; and 18, 21, 42 and 45, respectively.

The Tables referred to above list the rat genes identified in the preferred claims of this invention by GENBANK® or "UniGene" accession numbers. GENBANK® is the National Institute of Health's genetic sequence database and provides an annotated collection of all publicly available DNA sequences (Nucleic Acids Research 33 (Database Issue): D34-D36 (2005)). GENBANK® is part of the International Nucleotide Sequence Database Collaboration, which comprises the DNA DataBank of Japan (DDBJ), the European Molecular Biology Laboratory (EMBL), and GENBANK® at the National Center for Biotechnology Information (NCBI). The actual rat nucleotide sequence of the accession numbers listed herein may be found by searching the GENBANK® database on the "Entrez Nucleotide" portal of the NCBI website. Each UniGene entry comprises a set of transcript sequences that appear to come from the same transcription locus (gene or expressed pseudogene), together with information on protein similarities, gene expression, cDNA clone reagents, and genomic location, and is also accessible on the NCBI website.

Non-rat mammalian homologues, including human homologues, of the selected genes may be determined in a variety of ways. For example, one method is to access the "HomoloGene" portal of the NCBI website. and enter the GENBANK® or UniGene accession number to obtain a listing of all HomoloGene listings showing the homologues in every identified species in which the gene is conserved, including humans. The link on the desired species will produce the Entrez gene listing, which will have a reference ID for the human sequence of the gene. Alternatively, the human homologue may be identified by directly accessing the above-listed Entrez Gene website and entering the rat GENBANK® accession number. A map viewer of the homologous chromosomes is then accessible via the gene link. The map viewer identifies the human homologues and a click on the gene symbol will access several databases, including the Entrez Gene Sequence viewer (sv), which provides genomic, protein and mRNA sequences; HomoloGene (hm), see above; and Consensus CDS (CODS), another gene identification database that contains several links to protein and sequences.

The genes, identified and selected, by the above methods, and those specific individual genes listed in the Tables above, and their homologues are useful in identifying compounds useful in the treatment of cognitive impairment, and preferably cognitive impairment in aging in accordance with this invention.

One method to identify a compound useful in treating cognitive impairment in mammals, particularly humans, in accordance with this invention, comprises the steps of determining the abundance of an expressed gene product in a mammalian cell of the mammalian cell's homologue(s) of a gene or a plurality of genes identified as described above or listed in Tables 1-48 in the presence or absence of a candidate compound.

The mammalian cells can be any species of cell, e.g., human cells, mouse cells, rat cells, non-human primate cells. The cells can be from any known or established mammalian cell line, such as those available from the American Type Culture Collection (ATCC; Mannassas, Va.), for example, CHO cells, HEK293 cells or COS7 cells. The cells can be in primary cell culture or from a transformed cell line. The cells may naturally express the gene product (i.e., the gene may be wholly endogenous to the cell or multicellular organism) or the cell may be a recombinant cell or transgenic organism comprising one or more recombinantly expressed gene products.

Preferably, the cells are of human origin and more preferably are selected from the group consisting of neuronal cells and glial cells, including but not limited to, oligodendrocytes, astrocytes, microglia, pyramidal cells, granule cells, motoneurons, and Purkinje cells. Methods for culturing neuronal cells are well known see, e.g., Brewer et al., *J. Neuroscience Res.* 35:567 (1993) [hippocampal neurons]; Walsh et al., *Neuroscience* 69:915-29 (1995) [suprachiasmatic neurons]; Zoran et al., *Dev Biol.* 179:212-22 (1996) [motoneuronal cultures]. Preferably, the neuronal cell is a hippocampal cell or line derived from the hippocampus or a hippocampal region. More preferably, the cell is selected from a CA1, CA3 or DG hippocampal cell.

A number of different screening protocols can be utilized to identify compounds that change the abundance of an expressed gene product of a mammalian cell's homologue(s) of a gene or a plurality of genes identified as described above or individually listed in the above Tables in the mammalian cells. In general terms, the methods include culturing the cells in the presence of individual members of a plurality of candidate compounds to identify a compound that significantly changes—increases or decreases—in the appropriate direction, as defined herein, the abundance of an expressed gene product of a mammalian cell's homologue(s) of a gene or a plurality of genes identified as described above or individually listed in the Tables 1-48.

For example, a compound that decreases the abundance or attenuates the function of an expressed gene product of a gene identified in the methods of this invention or listed in Tables 1, 3, 9, 11, 17, 19, 25, 27, 33, 35, 41 and 43 that was increased in the AI population as compared to the combined AU and Y populations would be useful in treating cognitive impairment. Similarly, a compound that increases the abundance or enhances the function of an expressed gene product of a gene identified in the methods of this invention or listed in Tables 2, 4, 10, 12, 18, 20, 26, 28, 34, 36, 42 and 44 that was decreased in the AI population as compared to the combined AU and Y population would be useful in treating cognitive impairment.

In contrast, a compound that decreases the abundance or attenuates the function of expressed gene products of at least one gene identified in the methods of this invention or listed in Tables 5, 8, 13, 16, 21, 24, 29, 32, 37, 40, 45 and 48 that was decreased in the AU populations as compared to the combined AI and Y populations would be useful in treating cognitive impairment. Similarly, a compound that increases the abundance or enhances the function of one or more expressed gene products of at least one gene identified in the methods of this invention or listed in Tables 6, 7, 14, 15, 22, 23, 30, 31, 38, 39, 46 and 47 that was increased in the AU population as compared to the combined AI and Y populations would be useful in treating cognitive impairment.

One or more compounds from among the candidate compounds are then selected based on the compound's ability to significantly change, in the appropriate direction, as defined herein, the abundance or function of the expressed gene product of a selected gene or plurality of genes in the cell treated with the compound. Preferably, one gene whose decreased abundance of expressed gene product significantly correlates (negatively) with the level of cognitive impairment is the GABA-A α5 receptor gene (corresponding to GENBANK® accession number NM_017295), as shown in Example 10 and Table 10 (CA3 AI ANOVA negative correlation) and its homologues. Preferably, compounds that can significantly increase the abundance or enhance the function of GABA-A α5 protein produced by the gene would be useful for treating cognitive impairment are (1) the GABA-A α5 receptor agonist QH-ii-066 (1-methyl-7-acetyleno-5-phenyl-1,3-dihydro-benzo[e]-1,4-diazepin-2-one), see, Platt et al., Contribution of $_{\alpha 1}GABA_A$ and $_{\alpha 5}GABA_A$ Receptor Subtypes to the Discriminative Stimulus Effects of Ethanol in Squirrel Monkeys, *J. Pharmacol. Exp. Ther.* 313: 658-667 (2005); (2) 6,6 dimethyl-3-(3-hydroxypropyl)thio-1-(thiazol-2-yl)-6,7-dihydro-2-benzothiophen-4(5H)-one, corresponding to compound number 44 in Chambers et al., Identification of a Novel, Selective $GABA_A$ α5 Receptor Inverse Agonist Which Enhances Cognition, *J. Med. Chem.* 46:2227-2240 (2003); and (3) 8-ethylthio-3-methyl-5-(1-oxidopyridin-2-yl)-3,4-dihydronaphthalen-1(2H)-one, corresponding to compound number 19 in Szekeres et al., 3,4-Dihydronaphthalen-1(2H)-ones: novel ligands for the benzodiazepine site of alpha5-containing GABAA receptors. *Bioorg. Med. Chem. Lett.* 14:2871-2875 (2004).

Another method of identifying compounds useful in treating cognitive impairment assays the candidate compounds in mammals, preferably aged mammals, and more preferably aged mammals with cognitive impairment. In this element, the abundance or function of the expressed gene product of the mammal's homologue of a gene or plurality of genes selected in accordance with this invention or individually listed in the above Tables, is measured in hippocampal tissue, preferably CA1, CA3 or DG tissue of the mammal, to whom the candidate compound has been administered. Those compounds that cause a significant change—increase or decrease—in the appropriate direction, as defined herein, in that abundance or function in mammals treated with the compound are selected.

Compounds are selected that significantly change—increase or decrease—in the appropriate direction, as defined herein, the abundance or function of the expressed gene product of the mammal's homologue of a gene or plurality of genes selected in the method described above or individually listed in the above Tables in an aged mammal with cognitive impairment who has been treated with the compound, relative to a member of the group consisting of an aged mammal without cognitive impairment, a young mammal, an aged cognitively impaired mammal in the absence of the compound, and two or more of them. Preferably, the selected compound does not alter that abundance or function in a young mammal and/or an aged cognitively unimpaired mammal to whom the candidate compound is administered. Also preferably, the selected compound does not significantly alter the cognitive status of a young mammal and/or an aged cognitively unimpaired mammal to whom the candidate compound is administered.

The methods of this invention for identifying compounds useful in the treatment of cognitive impairment, and preferably that due to aging, also include assays based on the cognitive status of a mammal in the presence and absence of the candidate compound.

The cognitive status of a mammal, preferably an aged mammal and most preferably an aged cognitively impaired mammal, and more preferably a rat, is determined in the presence and absence of a candidate compound. The cognitive status of the mammal may be assessed using various functions. Preferably, the functions are hippocampal-dependent functions. More preferably, the functions are spatial memory acquisition, long-term spatial memory, and spatial memory retrieval.

It is preferable that the candidate compound be one that is believed to increase or decrease, in the appropriate direction, as defined herein, the abundance or function of an expressed gene product of the mammal's homologue of a gene or plurality of genes selected in the methods described above or listed in the Tables.

This belief may be based on actual experimental data using other elements of this invention or may be based on information in the scientific literature. A compound that beneficially alters the cognitive status of the treated animal is then selected as being useful in the treatment of cognitive impairment. Preferably, the selected compound beneficially alters the cognitive status in the treated mammal relative to a member of the group consisting of an aged mammal without cognitive impairment, a young mammal, an aged cognitively impaired mammal to whom the compound is not administered and two or more of them. Preferably, the compound does not significantly alter the cognitive status of young mammals or aged unimpaired mammals of the same species who are treated with the compound.

Candidate compounds for use in the methods of the invention include a wide variety of general types of well-known and available compounds including, but not limited to, small organic molecules (e.g., MW<1000, preferably <500); polypeptides; carbohydrates such as oligosaccharides and polysaccharides; polynucleotides; antibodies, lipids or phospholipids; fatty acids; steroids; amino acid analogs, and peptidomimetics. Candidate compounds can be obtained from libraries, such as natural product libraries and combinatorial libraries. A number of different libraries and collections containing large numbers of natural and synthetic compounds are commercially available and one of ordinary skill in the art would be familiar with methods for preparing and obtaining such libraries. Methods of automating assays are also known that permit screening of several thousands of compounds in a short period.

Compounds identified in accordance with the methods of this invention are useful in the treatment of cognitive impairment in mammals, preferably human, and preferably in methods of treating cognitive impairment in aged mammals, preferably humans. The particular compound from among the compounds selected by the methods of this invention to be used can be determined by those skilled in the art, and will depend, for example, on factors such as the severity of the cognitive impairment; the time period over which treatment of the cognitive impairment is desired; whether the compound is administered in a clinical setting or by the individual; or whether an individual suffers from age-related cognitive impairment.

Compounds, selected in accordance with this invention for use in treating cognitive impairment, and particularly that due to aging, or for use in the screening methods of this invention, can be formulated in pharmaceutical compositions in such a manner to ensure proper distribution in vivo. For example, the blood-brain barrier excludes many highly hydrophilic compounds. To ensure that the selected compounds the blood-brain barrier, they can be formulated, for example, in liposomes, or chemically derivatized. A wide variety of carriers can be used to facilitate targeted drug delivery across the blood-brain barrier to brain tissues, preferably the hippocampus, including but not limited to the use of liposomes, nanoparticles, microparticles, microspheres, encapsulated microbubbles or similar structures which envelope biologically or pharmaceutically active agents, carrier molecules including polymers, and protein including hydrophile proteins.

Administration of a selected compound, or candidate compound(s) to be screened can be in a single dose, or in multiple doses. An effective amount of a compound can be determined by those skilled in the art, and can depend on the chemical and biological properties of the compound and the method of contacting the subject. Typically between 0.1 and 1000 mg/kg is administered daily, for one or more days.

Administration of the compound can be carried out using one of a variety of methods known to those of skill in the art. For example, a compound can be administered, intravenously, arterially, intradermally, intramuscularly, intraperitonealy, intravenously, subcutaneously, ocularly, sublingually, orally (by ingestion), intranasally (by inhalation), intraspinally, intracerebrally, and transdermally (by absorbtion, e.g., through a skin duct). A compound can also appropriately be introduced by rechargeable or biodegradable polymeric devices, which provide for the slow release or controlled delivery of drugs.

Appropriate methods of administering a compound to a mammal will also depend, for example, on the age of the mammal, whether the mammal is active or inactive at the time of administering, whether the mammal is cognitively impaired at the time of administering, and the chemical and biological properties of the compound (e.g. solubility, digestibility, bioavailability, stability and toxicity). Preferably, a compound is administered orally, e.g., to a mammal by ingestion, where the compound is dissolved in food and provided to the mammal at mealtime.

Pharmaceutical compositions for oral administration can be formulated using pharmaceutically acceptable carriers well known in the art in dosages suitable for oral administration that enable the compositions to be formulated as, e.g., tablets, pills, dragees, capsules, liquids, gels, syrups, slurries, suspensions, and the like. Other appropriate routes of administration and doses of the compound can be determined by those skilled in the art.

It will be understood that the efficacy and safety of a compound in laboratory mammals can be evaluated before administering the compound to humans. For example, the compound can be tested for its maximal efficacy and any potential side-effects using several different non-human mammals, across a range of doses, in a range of formulations, and at various times of day, such as before or after sleeping, before or after eating, and the like. Preferably, the compound selected by the methods of the invention will cause few or no deleterious or unwanted side effects in any of the test populations. More preferably, the compound will cause few or no deleterious side effects in the mammal whose cognitive status is beneficially altered by the administration of the compound. Most preferably, the compound will cause few or no deleterious side effects in an aged cognitively impaired mammal to which the compound is administered.

Illustrative methods of this invention are described in the following Examples. Methods and materials similar or equivalent to those described can also be used in the practice of the present invention and will be apparent to those of skill in the art. The materials, methods, and examples are thus illustrative only and not intended to be limiting.

EXAMPLES

We performed the following examples using rats of an outbred strain behaviorally characterized as described in more detail below into one of three groups: Y, AU and AI.

Behavioral Characterization of Rats

We performed behavioral tests on 9 young (4-6 months) and 18 aged (25-27 months) pathogen-free male outbred Long-Evans rats with the Morris Water Maze (MWM) protocol. An additional 10 aged rats were tested in the MWM, followed by training and testing in the Radial Arm Maze to assess test-retest reliability for individual differences in cognitive function across the two tasks.

Morris Water Maze Apparatus

In the MWM assay, rats learn and remember the location of an escape platform guided by a configuration of spatial cues surrounding the maze. See, Morris, *Learning and Motivation* 12:239-260 (1981). The cognitive basis of performance is tested in probe trials using measures of the animal's spatial bias in searching for the location of the escape platform. Aged rats in the study population have no difficulty swimming to a visible platform, but an age-dependent cognitive impairment can be detected when the platform is camouflaged, requiring the use of spatial information.

When reassessed using the MWM in a new spatial environment several weeks after the original characterization, the AI animals are consistently impaired, whereas the AU animals again perform proficiently. Colombo et al., *Proc. Natl. Acad. Sci. USA*, 94:14195-99 (1997). The difference in cognitive ability in the MWM assessment for AI and AU rats is reliable even over an interval of 3 months. See, Gallagher and Burwell, *Neurobiol. Aging* 10:691-708 (1989). Further, AI and AU characterization in the MWM differentiates the performance of the same aged subjects in other behavioral tasks that require the same cognitive function, such as the Barnes circular maze, and the radial arm maze (RAM). This naturally occurring impairment in an aged population of rodents indicates that cognitive aging is not inevitable or strictly linked to chronological age, and, importantly, it affords the opportunity to compare the trajectory of changes in the brain that lead to decline or preserved memory.

The MWM apparatus consists of a large, circular pool (diameter 1.83 m; height, 0.58 m) filled with water (27° C.) that has been made opaque through the addition of non-toxic pigment or some other substance. In the typical "hidden platform" version of the task, rats are trained to find a camouflaged white escape platform (height, 34.5 cm) that is positioned in the center of one quadrant of the maze just 1.0 cm below the water surface. This platform can be retracted to the bottom of the tank or raised to its normal position from outside the maze during behavioral testing. The location of this platform remained constant from trial to trial. Because there were no local cues that marked the position of the platform, the rat's ability to locate it efficiently from any starting position at the perimeter of the pool depended on using information surrounding the maze. The maze was surrounded by black curtains with white patterns affixed to provide a configuration of spatial cues.

A second platform (height 37.5 cm) with its surface painted black was elevated 2 cm above the water surface during cue training, the version of the task used to control for factors unrelated to cognition. The behavior of a rat in the pool was recorded by a camera suspended 2.5 m above the center of the pool, connected to a video tracking system (HVS Image Advanced Tracker VP200) and a PC computer running HVS software developed by Richard Baker of HVS Image, Hampton, UK.

Morris Water Maze Procedure

We optimized the MWM protocol for sensitivity to the effects of aging on cognition and for measures of reliable individual differences within the aged population of outbred Long-Evans rats (Gallagher et al., *Behav. Neurosci.* 107:618-626 (1993)).

Rats received three trials per day for 8 consecutive days, using a 60 second inter-trial interval. On each training trial, the rat was released in the maze from one of four equally spaced starting positions around the perimeter of the pool. The starting position varied from trial to trial, thus preventing the use of a response strategy (e.g. always turning left from the start location to locate the escape platform). If a rat did not locate the escape platform within 90 sec on any trial, the experimenter guided the rat to the platform, where it remained for 30 sec. Every sixth trial consisted of a probe trial to assess the development of spatial bias in the maze. During these trials, the rat swam with the platform retracted to the bottom of the pool for 30 sec, at which time the platform was raised to its normal position for completion of an escape trial. At the completion of the protocol using the hidden platform, rats were assessed for cue learning using the visible platform. The location of this platform varied from trial to trial in a single session of 6 training trials.

We used the proximity of the animal's position with respect to the goal for analysis of training trial and probe trial performance. The proximity measure was obtained by sampling the position of the animal in the maze (10x/sec) to provide a record of distance from the escape platform in 1 sec averages. For both probe trials and training trials, a correction procedure was implemented so that trial performance was relatively unbiased by differences in distance to the goal from the various start locations at the perimeter of the pool. In making this correction the average swimming speed was calculated for each trial (path length/latency). Then, the amount of time required to swim to the goal at that speed from the start location used in the trial was removed from the record prior to computing trial performance, i.e. cumulative distance on training trials and average distance from the goal on probe trials. Thus, scores obtained using the proximity measure are designed to reflect search error, representing deviations from an optimal search, i.e. direct path to the goal and search in the immediate vicinity of that location during probe trials.

Morris Water Maze Analysis

Computer records of video-tracking were compiled to provide data on each rat's performance in the maze. Measures on training trials and probe trials were analyzed by ANOVA.

Morris Water Maze Data Results

The performance during training with the hidden, camouflaged platform differed between the groups of young and aged rats [F(1,23)=12.69, p<0.002]. No difference between the groups occurred for the cue training trials with a visible platform. Latencies to escape during cue training averaged 9.36 seconds for young and 10.60 seconds for the aged rats.

The average proximity measure on interpolated probe trials was used to calculate a spatial learning index for each individual subject as described in detail in Gallagher et al., *Behav. Neurosci.* 107:618-626 (1993). When a rat rapidly learned to search for the platform close to its position, its spatial learning index is low. Overall, aged rats differed from young [F(1,23)=15.18, p<0.001]. Aged rats were classified as either AU or AI relative to the learning index profile of the young study population. Aged rats that fall within the normative range of young rats (index scores<241) were designated AU. The remaining aged subjects that have index scores outside the range of young performance were designated AI.

Radial Arm Maze Apparatus

Each arm (7×75 cm) of the elevated eight arm radial arm maze (RAM) projected from each facet of an octagonal center platform (30 cm diameter, 51.5 cm height). Clear side walls on the arms were 10 cm high and were angled at 65° to form a trough. A food well (4 cm diameter, 2 cm deep) was located at the distal end of each arm. Blocks constructed of Plexiglas (30 cm H×12 cm W) could be positioned to block entry to any arm. Numerous extra maze cues were provided in the room surrounding the apparatus and overhead fixtures provided lighting.

Radial Arm Maze Procedures

Rats were first habituated to the maze for an 8 min session on four consecutive days. In each of these sessions food rewards were scattered on the RAM, initially on the center platform and arms and then progressively confined to the arms. After this habituation phase, a standard training protocol was used in which a food pellet was located at the end of each arm. Rats received one trial each day for 18 days; each daily trial terminated when all eight food pellets had been obtained or when either 16 choices were made or 15 min had elapsed. An error consisted of returning to an arm (all four paws on the arm) from which food had already been obtained.

After completion of this phase, the memory demand of the task was increased by imposing a delay during the trial. At the beginning of each trial three arms were blocked. The identity and configuration of the blocked arms was varied across trials. Rats were allowed to obtain food on the five arms to which access was permitted at the beginning of the trial. The rat was then removed from the maze for 60 seconds, during which time the barriers on the maze were removed, thus allowing access to all eight arms. Rats were then placed back onto the center platform and allowed to obtain the remaining food rewards.

Radial Arm Maze Analysis

A memory error occurred during test trials using a 60 second delay when a rat returned to one of the five arms that were already visited prior to the delay. Each rat's performance was averaged across four consecutive test trials. Parametric statistics (unpaired t-tests) were used to compare performance between young and aged groups. Correlational analysis (Pearson's r) was used to examine the relationship between performance of aged rats (N=10) in the MWM (learning index scores) and RAM (memory errors).

Radial Arm Maze Results

The performance of young adult rats in the delay version of the RAM varies as a function of the delay interval, ranging from 60 seconds to eight hours (Chappell et al. *Neuropharmacology* 37: 481-488, (1998)). Aged rats previously characterized in the MWM, committed more memory errors after a 60 second delay relative to young rats (p<0.025). On average young rats committed 0.17 errors, whereas aged rats committed an average of 1.52 errors. The ten aged rats, however, exhibited a wide range of performance on the RAM. A significant relationship was found between the initial MWM characterization and memory performance in the RAM (r value=0.82).

Gene Expression Analysis

We then analyzed the gene expression profiles in the CA1, CA3 or DG hippocampal regions. We determined the abundance of a plurality of expressed gene products in CA1, CA3 or DG hippocampal tissue from each mammal of the three populations—AI, AU and Y. We selected those genes, the abundance of whose expressed gene products was significantly increased or decreased in the AI population as compared to the combined Y and AU populations or significantly increased or decreased in the AU population as compared to the combined Y and AI populations. These genes may relate specifically to age-related cognitive impairment.

We selected from the above genes those whose increased or decreased abundance of expressed gene product(s) showed a significant correlation with the level of cognitive impairment in the AU and AI populations.

These analyses are described below.

Preparation of RNA from Behaviorally Characterized Rats

Twenty-four outbred Long-Evans rats, behaviorally characterized as described above, were killed by live decapitation to obtain fresh brain tissue. The brain was removed, the hippocampus dissected and the CA1, CA3 or DG hippocampal region was microdissected from 500 micron sections taken through the transverse axis of the entire hippocampal formation (both left and right hippocampi) of 24 characterized rats. There were 8 animals in each group (AI, AU and Y) and the CA1, CA3 or DG region of each animal was processed independently.

Total RNA was isolated using Trizol reagent (Invitrogen, Carlsbad, Calif.) according to the standard protocol (homogenization in Trizol reagent followed by chloroform extraction and isopropanol precipitation). Total RNA was further purified using the RNeasy mini kit (Qiagen, Valencia, Calif.). cRNA probes were then generated from the RNA samples at The Johns Hopkins Microarray Core Facility, generally according to Affymetrix specifications as detailed herein.

Briefly, 5 micrograms of total RNA were used to synthesize first strand cDNA using oligonucleotide probes with 24 oligo-dT plus T7 promoter as primer (Proligo LLC, Boulder, Calif.), and the SuperScript Choice System (Invitrogen). Following the double stranded cDNA synthesis, the product was purified by phenol-chloroform extraction, and biotinilated anti-sense cRNA was generated through in vitro transcription using the BioArray RNA High Yield Transcript Labeling kit (ENZO Life Sciences Inc., Farmingdale, N.Y.). 15 ug of the biotinilated cRNA was fragmented at 94° C. for 35 min (100 mM Trix-acetate, pH 8.2, 500 mM KOAc, 150 mM MgOAC). Hug of total fragmented cRNA was hybridized to the RAT genome 230-2 Affymetrix GeneChip array for 16 hours at 45° C. with constant rotation (60 rpm). The cRNA prepared from the CA1, CA3 or DG regions for each animal were hybridized to an individual microarray.

Affymetrix Fluidics Station 450 was then used to wash and stain the chips, removing the non-hybridized target and incubating with a streptavidin-phycoerythrin conjugate to stain the biotinilated cRNA. The staining was then amplified using goat immunoglobulin-G (IgG) as blocking reagent and biotinilated anti-streptavidin antibody (goat), followed by a second staining step with a streptavidin-phycoerythrin conjugate.

For quality control of the total RNA from the samples, the Agilent Bioanalyzer, Lab on a Chip technology, was used to confirm that all the samples had optimal rRNA ratios (1:2, for 18S and 28S, respectively) and clean run patterns.

For quality control of the hybridization, chip image, and comparison between chips, the following parameters were considered: Scaling factor: related to the overall intensity of the chip, to confirm the similar signal intensity and staining through out the samples; Background: estimation of unspecific or cross-hybridization; Percentage of present calls (for "MAS5" analysis only, see infra, Data Analysis of Microarray): percentage of transcripts that are considered significantly hybridized to the chip (present) by the algorithm; Glyseraldehyde-3-phosphate dehydrogenase (GAPDH) (3'/5'): representation of the RNA integrity by measuring the ratio of 3' to 5' regions for the housekeeping gene GAPDH, its presence in the chip and a ratio close to 1 advocates for a good integrity of the target (sample); Spikes (BioB/BioC) to confirm the detection level and sensitivity after hybridization.

Data Analysis of Microarray

Fluorescence was detected using the Affymetrix G3000 GeneArray Scanner and image analysis of each GeneChip was done through the GeneChip Operating System 1.1.1 (GCOS) software from Affymetrix, using the standard default settings. All of the GeneChip arrays use short oligonucleotides to probe for genes in an RNA sample.

For comparison between different chips, global scaling was used, scaling all probe sets to a user defined target intensity (TGT) of 150. Two different methods were used to estimate the relative expression of genes in different RNA samples. Examples 1-24 processed and summarized the probe set data by "MAS5" analysis. Examples 25-48 processed and summarized the probe set data by "gcRMA" analysis.

The first method, the MAS5 statistical method, produces absolute and comparison analysis results for GeneChip expression arrays. Mas5 employs a statistical algorithm that performs a background adjustment by making regional adjustments or "calls". This process makes expression level calls as to whether a particular probe set is present or absent. (See, Affymetric statistical algorithm description document, available on the Affymetrix website.)

In Examples 1-24, the total number of present calls and scaling factors were similar across all chips (normalization was scaled by a constant). Further analysis for presence/absence and statistical difference was performed on a region by region basis in the following manner. Probe sets were determined to be present in a region if it had a present call in four of eight animals in a single group, as per the standard MAS5 default settings using Affymetrix software.

The second method used to process and summarize the probe set data was "gcRMA" analysis. This statistical method employs background adjustment by estimating a global signal over the entire probe set and making a whole array adjustment, using quantile normalization. GcRMA is an open-source method that is based on robust averaging techniques and sequence-dependent affinity corrections. The robust averaging employed in gcRMA confers a strong immunity to outliers. See, Wu et al. A Model Based Background Adjustement for Oligonucleotide Expression Arrays. *Journal of American Statistical Association*. 99:909-917 (2004).

In Examples 25-48, gcRMA analysis was used to perform background and normalization processing, which coupled all the genes together, as did the MAS5 analysis in Examples 1-24. Further analysis for statistical difference included performing a background subtraction. Mismatched sequences (11 for each probe set) were ignored and only the perfect match sequences were considered. There was no elimination of genes based on present/absent calls. See, Quin et al., Evaluation of methods for oligonucleotide array data via quantitative real-time PCR. *BMC Bioinformatics,* 7:23 (2006).

For Examples 25-48, probe sets were annotated using the most recent Affymetrix annotation of April 2006 and all probe sets representing a specific gene were identified. For Examples 1-24, probe sets were annotated using the Affymetrix annotations of Jun. 20, 2005.

The probe set signal values were then analyzed in the following Examples by various statistical methods to identify those genes or plurality of genes expressed gene products that significantly changed in abundance—increase or decrease— and to identify those genes whose increased or decreased expression product(s) abundance correlated to cognitive impairment.

Example 1

An ANOVA was conducted on the probe set signal values for all present probe sets by combining two groups of animals and comparing them to the third group. An "AI ANOVA" was performed, where Aged Unimpaired were combined with Young and compared to Aged Impaired. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 1 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 1

| CA1 - AI ANOVA POSITIVE CORRELATION |
|---|
| GENBANK ® ID |
| BI295776 |
| AA963364 |
| AY190520 |
| NM_001002016 |
| NM_001005534 |
| NM_001008374 |
| NM_001008862 |
| NM_001012177 |
| NM_001013112 |
| NM_012543 |
| NM_012577 |
| NM_012650 |
| NM_012918 |
| NM_013001 |
| NM_013157 |
| NM_017068 |
| NM_017223 |
| NM_017347 |
| NM_019212 |
| NM_019289 |
| NM_019305 |
| NM_019359 |
| NM_019362 |
| NM_021657 |
| NM_022244 |
| NM_022261 |

TABLE 1-continued

| CA1 - AI ANOVA POSITIVE CORRELATION |
|---|
| NM_022617 |
| NM_023981 |
| NM_024138 |
| NM_030863 |
| NM_031037 |
| NM_031147 |
| NM_031818 |
| NM_053418 |
| NM_053485 |
| NM_053525 |
| NM_053536 |
| NM_053669 |
| NM_053774 |
| NM_053896 |
| NM_053910 |
| NM_057103 |
| NM_080887 |
| NM_130413 |
| NM_133621 |
| NM_134390 |
| NM_145674 |
| NM_172038 |
| NM_173325 |
| NM_175582 |
| NM_198738 |
| NM_198759 |
| NM_207602 |
| NM_212528 |
| XM_214769 |
| XM_214968 |
| XM_215095 |
| XM_216004 |
| XM_221231 |
| XM_224538 |
| XM_230616 |
| XM_235566 |
| XM_237000 |
| XM_243637 |
| XM_340967 |
| XM_343773 |
| XM_344524 |
| XM_345140 |
| XM_575962 |
| UniGene ID |
| Rn.110441 |
| Rn.11453 |

The genes in this set show abundance of expressed gene product(s) in the Aged Impaired population that are significantly increased, as determined by ANOVA, compared to those abundances in Young and Aged Unimpaired populations combined. In addition, the abundance of expressed gene product(s) in the aged animals positively correlate with learning index of the animals, such that poorer learners have higher abundances of expressed gene products of the selected genes. Therefore, compounds useful in treating cognitive impairment selected using these genes should decrease the abundance or attenuate the function of the expressed gene products of these genes.

Example 2

An ANOVA was conducted on the probe set signal values for all present probe sets by combining two groups of animals and comparing them to the third group. An "AI ANOVA" was performed, where Aged Unimpaired were combined with Young and compared to Aged Impaired. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 2 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 2

| CA1 - AI ANOVA NEGATIVE CORRELATION |
|---|
| GENBANK ® ID |
| BG381750 |
| NM_001004210 |
| NM_001004279 |
| NM_001004442 |
| NM_001011955 |
| NM_001012035 |
| NM_001013178 |
| NM_001024765 |
| NM_012919 |
| NM_013083 |
| NM_013086 |
| NM_017322 |
| NM_020078 |
| NM_022395 |
| NM_022867 |
| NM_022934 |
| NM_024000 |
| NM_030861 |
| NM_031699 |
| NM_031707 |
| NM_031730 |
| NM_031821 |
| NM_053328 |
| NM_053402 |
| NM_053434 |
| NM_053686 |
| NM_053748 |
| NM_053883 |
| NM_133563 |
| NM_134383 |
| NM_134408 |
| NM_138838 |
| NM_139091 |
| NM_153472 |
| NM_172332 |
| NM_173133 |
| NM_199091 |
| XM_214043 |
| XM_214245 |
| XM_214428 |
| XM_214836 |
| XM_215812 |
| XM_215883 |
| XM_216102 |
| XM_216884 |
| XM_217464 |
| XM_217893 |
| XM_218502 |
| XM_218506 |
| XM_220281 |
| XM_220629 |
| XM_221635 |
| XM_222773 |
| XM_223693 |
| XM_226779 |
| XM_232995 |
| XM_235878 |
| XM_236914 |
| XM_341663 |
| XM_342044 |
| XM_342920 |

TABLE 2-continued

CA1 - AI ANOVA NEGATIVE CORRELATION

XM_343059
XM_343154
XM_343581
UniGene ID

Rn.101929

The genes in this set show abundance of expressed gene product(s) in the Aged Impaired population that are significantly decreased, as determined by ANOVA, compared to those abundances in Young and Aged Unimpaired populations combined. In addition, the abundance of expressed gene product(s) in the aged animals negatively correlate with learning index of the animals, such that poorer learners have lower abundances of expressed gene products of the selected genes. Therefore, compounds useful in treating cognitive impairment selected using these genes should increase the abundance or enhance the function of the expressed gene products of these genes.

Example 3

An ANOVA was conducted on the probe set signal values for all present probe sets by combining two groups of animals and comparing them to the third group. An "AI ANOVA" was performed, where Aged Unimpaired were combined with Young and compared to Aged Impaired. Any probe sets having a p-value less than 0.05 were considered significantly changed and the genes or plurality of genes selected.

Microarray Results

Table 3 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 3

CA1 - AI ANOVA INCREASE

GENBANK ® ID

AJ249701
NM_017154
AW528959
AF452647
NM_001002835
NM_001004209
NM_001005539
NM_001005565
NM_001007654
NM_001007682
NM_001007749
NM_001009651
NM_001011890
NM_001011934
NM_001011946
NM_001011974
NM_001011993
NM_001012069
NM_001012097
NM_001012141
NM_001012154
NM_001012351
NM_001013086
NM_001013118
NM_001013121

TABLE 3-continued

CA1 - AI ANOVA INCREASE

NM_001013179
NM_001013238
NM_001015004
NM_012488
NM_012512
NM_012523
NM_012562
NM_012654
NM_012671
NM_012703
NM_012749
NM_012771
NM_012823
NM_012838
NM_012884
NM_012899
NM_012984
NM_013015
NM_013055
NM_013091
NM_013096
NM_013107
NM_013198
NM_017009
NM_017109
NM_017169
NM_017181
NM_017209
NM_017320
NM_017351
NM_017356
NM_019238
NM_019278
NM_019335
NM_019363
NM_019620
NM_021576
NM_021690
NM_022390
NM_022500
NM_022502
NM_022512
NM_022526
NM_022531
NM_022864
NM_022948
NM_024155
NM_024387
NM_030992
NM_031153
NM_031357
NM_031509
NM_031552
NM_031640
NM_031714
NM_031797
NM_031798
NM_053021
NM_053314
NM_053323
NM_053424
NM_053455
NM_053492
NM_053502
NM_053516
NM_053538
NM_053612
NM_053639
NM_053818
NM_054001
NM_057107
NM_057120
NM_057123
NM_057185
NM_057197
NM_080890
NM_130409
NM_130428

TABLE 3-continued

CA1 - AI ANOVA INCREASE

NM_133298
NM_133392
NM_133393
NM_133548
NM_133605
NM_134334
NM_134349
NM_134407
NM_134410
NM_138508
NM_138521
NM_138539
NM_138826
NM_139060
NM_139110
NM_139185
NM_139192
NM_139256
NM_145775
NM_153315
NM_153621
NM_173095
NM_173118
NM_173123
NM_173141
NM_175578
NM_175756
NM_176077
NM_178095
NM_182821
NM_199404
NM_207591
NM_212466
XM_213329
XM_213574
XM_213610
XM_214250
XM_214298
XM_214403
XM_214518
XM_215037
XM_215578
XM_215935
XM_216367
XM_216565
XM_216665
XM_216882
XM_217252
XM_217470
XM_219447
XM_220264
XM_221369
XM_221387
XM_223080
XM_223087
XM_223190
XM_223781
XM_223785
XM_224337
XM_225885
XM_227701
XM_228073
XM_229225
XM_230296
XM_231120
XM_231287
XM_232531
XM_232671
XM_234483
XM_237049
XM_341081
XM_341509
XM_342291
XM_342331
XM_342794
XM_343057
XM_343126
XM_343159

TABLE 3-continued

CA1 - AI ANOVA INCREASE

XM_343259
XM_343310
XM_343640
XM_343650
XM_573983
XM_576401
XM_579460
XM_579675

UniGene ID

Rn.116787
Rn.129174
Rn.24948

The genes in this set show abundance of expressed gene product(s) in the Aged Impaired population that are significantly increased, as determined by ANOVA, compared to those abundances in Young and Aged Unimpaired populations combined. Therefore, compounds useful in treating cognitive impairment selected using these genes should decrease the abundance or attenuate the function of the expressed gene products of these genes.

Example 4

An ANOVA was conducted on the probe set signal values for all present probe sets by combining two groups of animals and comparing them to the third group. An "AI ANOVA" was performed, where Aged Unimpaired were combined with Young and compared to Aged Impaired. Any probe sets having a p-value less than 0.05 were considered significantly changed and the genes or plurality of genes selected.

Microarray Results

Table 4 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 4

CA1 - AI ANOVA DECREASE

GENBANK ® ID

AI231320
BF284573
BF392810
NM_001002289
NM_001004133
NM_001004284
NM_001009605
NM_001009953
NM_001011901
NM_001011964
NM_001011998
NM_001012011
NM_001012078
NM_001012144
NM_001012179
NM_001012214
NM_001012473
NM_001013036
NM_001013096
NM_001013244
NM_001013910
NM_001014793
NM_012527

TABLE 4-continued

CA1 - AI ANOVA DECREASE

NM_012550
NM_012561
NM_012573
NM_012576
NM_012769
NM_012911
NM_012985
NM_013102
NM_017041
NM_017074
NM_017204
NM_017242
NM_017318
NM_017336
NM_019169
NM_019211
NM_020306
NM_021597
NM_021697
NM_021850
NM_022252
NM_022254
NM_022289
NM_022548
NM_031036
NM_031318
NM_031325
NM_031514
NM_031560
NM_031740
NM_031745
NM_031753
NM_031777
NM_032085
NM_053375
NM_053401
NM_053410
NM_053441
NM_053483
NM_053772
NM_053849
NM_053868
NM_053933
NM_057196
NM_057200
NM_080411
NM_080582
NM_080902
NM_133406
NM_133425
NM_133429
NM_138837
NM_138849
NM_138866
NM_138887
NM_144758
NM_172034
NM_173145
NM_181380
NM_184051
NM_198726
NM_212520
U57097
X53232
XM_213426
XM_213679
XM_213906
XM_213954
XM_214454
XM_214668
XM_215566
XM_216158
XM_216656
XM_217115
XM_218828
XM_219128
XM_221496
XM_221888

TABLE 4-continued

CA1 - AI ANOVA DECREASE

XM_221962
XM_222251
XM_222661
XM_222726
XM_224707
XM_224929
XM_225220
XM_226888
XM_230449
XM_232220
XM_236932
XM_239171
XM_239260
XM_341157
XM_341239
XM_341391
XM_341712
XM_341745
XM_342107
XM_342344
XM_342600
XM_342808
XM_343046
XM_343175
XM_343761
XM_344594
XM_345861
XM_345981

UniGene ID

Rn.122667
Rn.15446
Rn.48866

The genes in this set show abundance of expressed gene product(s) in the Aged Impaired population that are significantly decreased, as determined by ANOVA, compared to those abundances in Young and Aged Unimpaired populations combined. Therefore, compounds useful in treating cognitive impairment selected using these genes should increase the abundance or enhance the function of the expressed gene products of these genes.

Example 5

An ANOVA was conducted on the probe set signal values for all present probe sets by combining two groups of animals and comparing them to the third group. An "AU ANOVA" was performed, where Aged Impaired were combined with Young and compared to Aged Unimpaired. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 5 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 5

CA1 - AU ANOVA POSITIVE CORRELATION

| GENBANK® ID |
| --- |
| AI145040 |
| NM_001007629 |
| NM_001012028 |
| NM_012546 |
| NM_019152 |
| NM_022177 |
| NM_022286 |
| NM_022858 |
| NM_022946 |
| NM_080692 |
| NM_138515 |
| NM_139260 |
| NM_172041 |
| XM_213564 |
| XM_214003 |
| XM_222245 |
| XM_233462 |
| XM_341100 |
| XM_341558 |
| XM_342548 |
| XM_343468 |
| XM_343764 |
| XM_346061 |
| UniGene ID |
| Rn.36521 |

The genes in this set show abundance of expressed gene product(s) in the Aged Unimpaired population that are significantly decreased, as determined by ANOVA, compared to those abundances in Young and Aged Impaired populations combined. In addition, the abundance of expressed gene product(s) in the aged animals positively correlate with learning index of the animals, such that poorer learners have higher abundances of expressed gene products of the selected genes. Therefore, compounds useful in treating cognitive impairment selected using these genes should decrease the abundance or attenuate the function of the expressed gene products of these genes.

Example 6

An ANOVA was conducted on the probe set signal values for all present probe sets by combining two groups of animals and comparing them to the third group. An "AU ANOVA" was performed, where Aged Impaired were combined with Young and compared to Aged Unimpaired. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 6 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 6

CA1 - AU ANOVA NEGATIVE CORRELATION
GENBANK® ID

| |
| --- |
| NM_001002830 |
| NM_001012034 |
| NM_001012036 |
| NM_012806 |
| NM_017126 |
| NM_019249 |
| NM_019361 |
| NM_021754 |
| NM_031058 |
| NM_031315 |
| NM_032083 |
| NM_053578 |
| NM_080584 |
| NM_175604 |
| NM_182844 |
| NM_199397 |
| NM_199463 |
| XM_214033 |
| XM_215528 |
| XM_218041 |
| XM_218963 |
| XM_221213 |
| XM_225253 |
| XM_226334 |
| XM_228197 |
| XM_237115 |
| XM_341694 |
| XM_342580 |
| XM_343228 |

The genes in this set show abundance of expressed gene product(s) in the Aged Unimpaired population that are significantly increased, as determined by ANOVA, compared to those abundances in Young and Aged Impaired populations combined. In addition, the abundance of expressed gene product(s) in the aged animals negatively correlate with learning index of the animals, such that poorer learners have lower abundances of expressed gene products of the selected genes. Therefore, compounds useful in treating cognitive impairment selected using these genes should increase the abundance or enhance the function of the expressed gene products of these genes.

Example 7

An ANOVA was conducted on the probe set signal values for all present probe sets by combining two groups of animals and comparing them to the third group. An "AU ANOVA" was performed, where Aged Impaired were combined with Young and compared to Aged Unimpaired. Any probe sets having a p-value less than 0.05 were considered significantly changed and the genes or plurality of genes selected.

Microarray Results

Table 7 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 7

CA1 - AU ANOVA INCREASE
GENBANK® ID

| |
| --- |
| NM_001004256 |
| NM_001007797 |

TABLE 7-continued

CA1 - AU ANOVA INCREASE
GENBANK® ID

NM_001008317
NM_001008509
NM_001008515
NM_001008556
NM_001008876
NM_001009619
NM_001011953
NM_001011979
NM_001012105
NM_001012131
NM_001013110
NM_001013151
NM_001013201
NM_001013210
NM_001013213
NM_001015003
NM_001015015
NM_012935
NM_012992
NM_013088
NM_013150
NM_016994
NM_017000
NM_017031
NM_017137
NM_017271
NM_017303
NM_017306
NM_017313
NM_019251
NM_019257
NM_020092
NM_021266
NM_022215
NM_022270
NM_022545
NM_022921
NM_024125
NM_031087
NM_031623
NM_031694
NM_032065
NM_053662
NM_053842
NM_053876
NM_053901
NM_057101
NM_130740
NM_131911
NM_133411
NM_134326
NM_134395
NM_138536
NM_139253
NM_145084
NM_145092
NM_153303
NM_153475
NM_175762
NM_175764
NM_199117
NM_199118
NM_212496
NM_213565
U77829
XM_213883
XM_214163
XM_215283
XM_215733
XM_215947
XM_216225
XM_216968
XM_217388
XM_218648
XM_218816
XM_219885
XM_221307
XM_221656
XM_221787
XM_227674
XM_232413
XM_236263
XM_236911
XM_237828
XM_341742
XM_341803
XM_342154
XM_342459
XM_342579
XM_342591
XM_343619
XM_344606
XM_345421
XM_573903
XM_575860
XM_576437

The genes in this set show abundance of expressed gene product(s) in the Aged Unimpaired population that are significantly increased, as determined by ANOVA, compared to those abundances in Young and Aged Impaired populations combined. Therefore, compounds useful in treating cognitive impairment selected using these genes should increase the abundance or enhance the function of the expressed gene products of these genes.

Example 8

An ANOVA was conducted on the probe set signal values for all present probe sets by combining two groups of animals and comparing them to the third group. An "AU ANOVA" was performed, where Aged Impaired were combined with Young and compared to Aged Unimpaired. Any probe sets having a p-value less than 0.05 were considered significantly changed and the genes or plurality of genes selected.

Microarray Results

Table 8 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 8

CA1 - AU ANOVA DECREASE
GENBANK® ID

AI236198
NM_001004446
NM_001007150
NM_001008279
NM_001013071
NM_001013122
NM_012545
NM_012648
NM_012762
NM_012784
NM_012808
NM_013197
NM_017061
NM_019159
NM_021671
NM_021703

TABLE 8-continued

CA1 - AU ANOVA DECREASE

NM_022250
NM_022609
NM_022676
NM_022853
NM_023972
NM_030988
NM_031018
NM_031654
NM_052983
NM_053428
NM_053788
NM_053797
NM_053811
NM_053859
NM_053893
NM_053996
NM_080394
NM_080580
NM_130430
NM_131906
NM_133313
NM_133400
NM_138854
NM_207592
XM_214963
XM_220884
XM_220982
XM_221273
XM_223768
XM_232640
XM_234901
XM_340775
XM_340999
XM_342134
XM_342863
XM_343559
XM_574284
UniGene ID Rn.95299

The genes in this set show abundance of expressed gene product(s) in the Aged Unimpaired population that are significantly decreased, as determined by ANOVA, compared to those abundances in Young and Aged Impaired populations combined. Therefore, compounds useful in treating cognitive impairment selected using these genes should decrease the abundance or attenuate the function of the expressed gene products of these genes.

Example 9

An ANOVA was conducted on the probe set signal values for all present probe sets by combining two groups of animals and comparing them to the third group. An "AI ANOVA" was performed, where Aged Unimpaired were combined with Young and compared to Aged Impaired. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 9 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 9

CA3 - AI ANOVA POSITIVE CORRELATION

GENBANK ® ID

BF420467
AF452731
AY190520
NM_001001511
NM_001007146
NM_001007617
NM_001007797
NM_001008289
NM_001008331
NM_001008880
NM_001008893
NM_001009474
NM_001011890
NM_001011893
NM_001011915
NM_001011946
NM_001011991
NM_001012025
NM_001012072
NM_001012075
NM_001012097
NM_001012106
NM_001012123
NM_001012162
NM_001012203
NM_001012215
NM_001013112
NM_001013121
NM_001013130
NM_001013192
NM_001013218
NM_001017386
NM_012502
NM_012519
NM_012577
NM_012618
NM_012671
NM_012720
NM_012778
NM_012781
NM_012804
NM_012809
NM_012825
NM_012925
NM_012999
NM_013005
NM_013045
NM_013060
NM_013096
NM_013137
NM_013199
NM_017012
NM_017015
NM_017026
NM_017031
NM_017041
NM_017068
NM_017073
NM_017175
NM_017181
NM_017197
NM_017206
NM_017214
NM_017223
NM_017239
NM_017248
NM_017261
NM_017274
NM_017307
NM_017329
NM_017333
NM_017354

TABLE 9-continued

CA3 - AI ANOVA POSITIVE CORRELATION

| |
|---|
| NM_017357 |
| NM_019161 |
| NM_019185 |
| NM_019249 |
| NM_019256 |
| NM_019288 |
| NM_019312 |
| NM_019341 |
| NM_019358 |
| NM_020098 |
| NM_021595 |
| NM_021682 |
| NM_021769 |
| NM_021868 |
| NM_022178 |
| NM_022207 |
| NM_022285 |
| NM_022861 |
| NM_024161 |
| NM_024364 |
| NM_030832 |
| NM_031006 |
| NM_031022 |
| NM_031034 |
| NM_031049 |
| NM_031092 |
| NM_031093 |
| NM_031140 |
| NM_031357 |
| NM_031521 |
| NM_031576 |
| NM_031587 |
| NM_031613 |
| NM_031755 |
| NM_031798 |
| NM_031841 |
| NM_032062 |
| NM_032066 |
| NM_032617 |
| NM_052807 |
| NM_053314 |
| NM_053328 |
| NM_053416 |
| NM_053467 |
| NM_053492 |
| NM_053536 |
| NM_053615 |
| NM_053639 |
| NM_053643 |
| NM_053681 |
| NM_053741 |
| NM_053766 |
| NM_053799 |
| NM_053814 |
| NM_053824 |
| NM_053936 |
| NM_057137 |
| NM_057138 |
| NM_057148 |
| NM_057197 |
| NM_057200 |
| NM_130403 |
| NM_133560 |
| NM_133602 |
| NM_133605 |
| NM_134351 |
| NM_138832 |
| NM_138905 |
| NM_138914 |
| NM_139038 |
| NM_139103 |
| NM_145081 |
| NM_145094 |
| NM_147136 |
| NM_147210 |
| NM_152847 |
| NM_153470 |
| NM_172030 |
| NM_172033 |
| NM_173120 |
| NM_175578 |
| NM_175582 |
| NM_175595 |
| NM_175838 |
| NM_177928 |
| NM_178095 |
| NM_199119 |
| NM_199253 |
| NM_212529 |
| NM_213629 |
| XM_213779 |
| XM_213824 |
| XM_213849 |
| XM_213920 |
| XM_214172 |
| XM_214187 |
| XM_214539 |
| XM_214740 |
| XM_214968 |
| XM_215095 |
| XM_215184 |
| XM_215264 |
| XM_215733 |
| XM_215739 |
| XM_216340 |
| XM_216688 |
| XM_216755 |
| XM_217062 |
| XM_217279 |
| XM_217409 |
| XM_217570 |
| XM_218162 |
| XM_218226 |
| XM_218292 |
| XM_218816 |
| XM_219262 |
| XM_219998 |
| XM_220420 |
| XM_220805 |
| XM_220986 |
| XM_222745 |
| XM_222780 |
| XM_223583 |
| XM_225008 |
| XM_225014 |
| XM_225404 |
| XM_225628 |
| XM_226237 |
| XM_226779 |
| XM_227203 |
| XM_228073 |
| XM_229225 |
| XM_229988 |
| XM_230288 |
| XM_231121 |
| XM_231193 |
| XM_231287 |
| XM_231714 |
| XM_232172 |
| XM_232671 |
| XM_232809 |
| XM_235326 |
| XM_237042 |
| XM_237232 |
| XM_237381 |
| XM_238057 |
| XM_238103 |
| XM_238213 |
| XM_240330 |
| XM_241375 |
| XM_242032 |
| XM_242057 |
| XM_340739 |
| XM_340825 |
| XM_340879 |
| XM_340911 |

TABLE 9-continued

CA3 - AI ANOVA POSITIVE CORRELATION

XM_341052
XM_341172
XM_341352
XM_341538
XM_341940
XM_342141
XM_342405
XM_342591
XM_342626
XM_342648
XM_342662
XM_342928
XM_343131
XM_343174
XM_343358
XM_343380
XM_343570
XM_343919
XM_343971
XM_344403
XM_345446
XM_573298
XM_574593
XM_576343
XM_579200
XM_579675

UniGene ID

Rn.22102

The genes in this set show abundance of expressed gene product(s) in the Aged Impaired population that are significantly increased, as determined by ANOVA, compared to those abundances in Young and Aged Unimpaired populations combined. In addition, the abundance of expressed gene product(s) in the aged animals positively correlate with learning index of the animals, such that poorer learners have higher abundances of expressed gene products of the selected genes. Therefore, compounds useful in treating cognitive impairment selected using these genes should decrease the abundance or attenuate the function of the expressed gene products of these genes.

Example 10

An ANOVA was conducted on the probe set signal values for all present probe sets by combining two groups of animals and comparing them to the third group. An "AI ANOVA" was performed, where Aged Unimpaired were combined with Young and compared to Aged Impaired. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 10 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 10

CA3 - AI ANOVA NEGATIVE CORRELATION

GENBANK ® ID

BG379941
BM389079
AI228348
AY325138
NM_001004133
NM_001004210
NM_001004235
NM_001004442
NM_001005564
NM_001005884
NM_001006972
NM_001007150
NM_001007656
NM_001009605
NM_001009679
NM_001011901
NM_001011923
NM_001011955
NM_001011978
NM_001011996
NM_001012012
NM_001012035
NM_001012103
NM_001012144
NM_001012170
NM_001013087
NM_001013170
NM_001014785
NM_012600
NM_012664
NM_012670
NM_012784
NM_012869
NM_013067
NM_013083
NM_013090
NM_013174
NM_013192
NM_013219
NM_017010
NM_017011
NM_017051
NM_017135
NM_017294
NM_017295
NM_019133
NM_019166
NM_019226
NM_019368
NM_021688
NM_021842
NM_021850
NM_022188
NM_022249
NM_022264
NM_022399
NM_022511
NM_022688
NM_022860
NM_022867
NM_022934
NM_023957
NM_023979
NM_024139
NM_024403
NM_030830
NM_030841
NM_030869
NM_031030
NM_031070
NM_031104
NM_031119
NM_031134
NM_031569
NM_031641
NM_031642

TABLE 10-continued

CA3 - AI ANOVA NEGATIVE CORRELATION

| |
|---|
| NM_031662 |
| NM_031693 |
| NM_031715 |
| NM_031763 |
| NM_031840 |
| NM_033349 |
| NM_053291 |
| NM_053301 |
| NM_053316 |
| NM_053404 |
| NM_053490 |
| NM_053556 |
| NM_053585 |
| NM_053607 |
| NM_053660 |
| NM_053682 |
| NM_053693 |
| NM_053795 |
| NM_053801 |
| NM_053849 |
| NM_053876 |
| NM_053883 |
| NM_053928 |
| NM_053961 |
| NM_057098 |
| NM_057099 |
| NM_057190 |
| NM_130779 |
| NM_133394 |
| NM_133562 |
| NM_133609 |
| NM_134346 |
| NM_138548 |
| NM_138866 |
| NM_138899 |
| NM_138910 |
| NM_138911 |
| NM_139325 |
| NM_145098 |
| NM_145677 |
| NM_153730 |
| NM_172008 |
| NM_172039 |
| NM_172062 |
| NM_172074 |
| NM_173133 |
| NM_173154 |
| NM_173309 |
| NM_181377 |
| NM_181379 |
| NM_198726 |
| NM_199086 |
| NM_199091 |
| NM_199373 |
| NM_212490 |
| XM_213234 |
| XM_213469 |
| XM_213906 |
| XM_214072 |
| XM_214153 |
| XM_214307 |
| XM_214554 |
| XM_214859 |
| XM_215069 |
| XM_215124 |
| XM_215751 |
| XM_215826 |
| XM_215883 |
| XM_215931 |
| XM_216013 |
| XM_216180 |
| XM_216212 |
| XM_216766 |
| XM_216910 |
| XM_217147 |
| XM_217464 |
| XM_217893 |
| XM_218084 |
| XM_218186 |
| XM_218717 |
| XM_220178 |
| XM_220219 |
| XM_220428 |
| XM_220604 |
| XM_220698 |
| XM_221023 |
| XM_221034 |
| XM_221043 |
| XM_221202 |
| XM_221962 |
| XM_222107 |
| XM_223580 |
| XM_223693 |
| XM_223921 |
| XM_223981 |
| XM_224733 |
| XM_226888 |
| XM_227499 |
| XM_230523 |
| XM_230531 |
| XM_231176 |
| XM_231925 |
| XM_232735 |
| XM_233544 |
| XM_235500 |
| XM_238177 |
| XM_238346 |
| XM_239171 |
| XM_239504 |
| XM_340906 |
| XM_340916 |
| XM_341090 |
| XM_341157 |
| XM_341314 |
| XM_341669 |
| XM_341763 |
| XM_342107 |
| XM_342295 |
| XM_342588 |
| XM_342823 |
| XM_342924 |
| XM_342930 |
| XM_343910 |
| XM_344048 |
| XM_347168 |
| XM_574001 |
| XM_576494 |
| XM_577170 |

| UniGene ID |
|---|
| Rn.102180 |
| Rn.21816 |
| Rn.24317 |

The genes in this set show abundance of expressed gene product(s) in the Aged Impaired population that are significantly decreased, as determined by ANOVA, compared to those abundances in Young and Aged Unimpaired populations combined. In addition, the abundance of expressed gene product(s) in the aged animals negatively correlate with learning index of the animals, such that poorer learners have lower abundances of expressed gene products of the selected genes. Therefore, compounds useful in treating cognitive impairment selected using these genes should increase the abundance or enhance the function of the expressed gene products of these genes.

Example 11

An ANOVA was conducted on the probe set signal values for all present probe sets by combining two groups of animals and comparing them to the third group. An "AI ANOVA" was performed, where Aged Unimpaired were combined with Young and compared to Aged Impaired. Any probe sets having a p-value less than 0.05 were considered significantly changed and the genes or plurality of genes selected.

Microarray Results

Table 11 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 11

| CA3 - AI ANOVA INCREASE |
| --- |
| GENBANK ® ID |
| BI295776 |
| AI178069 |
| AF022087 |
| AF155825 |
| AF187100 |
| M17422 |
| NM_001005539 |
| NM_001005761 |
| NM_001007002 |
| NM_001007005 |
| NM_001007145 |
| NM_001007607 |
| NM_001007628 |
| NM_001007636 |
| NM_001007641 |
| NM_001007744 |
| NM_001008306 |
| NM_001008316 |
| NM_001008356 |
| NM_001008509 |
| NM_001008767 |
| NM_001009623 |
| NM_001011910 |
| NM_001011954 |
| NM_001011959 |
| NM_001011981 |
| NM_001012040 |
| NM_001012163 |
| NM_001012181 |
| NM_001012193 |
| NM_001012217 |
| NM_001012459 |
| NM_001012464 |
| NM_001013058 |
| NM_001013086 |
| NM_001013148 |
| NM_001013173 |
| NM_001013179 |
| NM_001013195 |
| NM_001013200 |
| NM_001014843 |
| NM_001024278 |
| NM_012507 |
| NM_012532 |
| NM_012543 |
| NM_012654 |
| NM_012655 |
| NM_012714 |
| NM_012747 |
| NM_012749 |
| NM_012776 |
| NM_012788 |
| NM_012844 |
| NM_012908 |
| NM_012913 |
| NM_012948 |
| NM_012984 |
| NM_013015 |
| NM_013016 |
| NM_013044 |

TABLE 11-continued

| CA3 - AI ANOVA INCREASE |
| --- |
| NM_013088 |
| NM_013107 |
| NM_013132 |
| NM_013176 |
| NM_013198 |
| NM_017009 |
| NM_017024 |
| NM_017030 |
| NM_017060 |
| NM_017062 |
| NM_017075 |
| NM_017109 |
| NM_017125 |
| NM_017148 |
| NM_017192 |
| NM_017200 |
| NM_017347 |
| NM_017365 |
| NM_019140 |
| NM_019146 |
| NM_019152 |
| NM_019156 |
| NM_019168 |
| NM_019252 |
| NM_019269 |
| NM_019311 |
| NM_019318 |
| NM_019359 |
| NM_020073 |
| NM_020084 |
| NM_021663 |
| NM_021672 |
| NM_021681 |
| NM_021694 |
| NM_021746 |
| NM_021853 |
| NM_022184 |
| NM_022198 |
| NM_022226 |
| NM_022236 |
| NM_022250 |
| NM_022270 |
| NM_022272 |
| NM_022390 |
| NM_022500 |
| NM_022592 |
| NM_022629 |
| NM_022799 |
| NM_024148 |
| NM_024154 |
| NM_024155 |
| NM_024373 |
| NM_024404 |
| NM_030872 |
| NM_031035 |
| NM_031052 |
| NM_031091 |
| NM_031144 |
| NM_031235 |
| NM_031509 |
| NM_031556 |
| NM_031599 |
| NM_031620 |
| NM_031648 |
| NM_031771 |
| NM_031772 |
| NM_031797 |
| NM_031818 |
| NM_031837 |
| NM_031970 |
| NM_032083 |
| NM_053021 |
| NM_053323 |
| NM_053349 |
| NM_053418 |
| NM_053534 |
| NM_053538 |
| NM_053576 |

TABLE 11-continued

CA3 - AI ANOVA INCREASE

| | |
|---|---|
| NM_053749 | XM_216188 |
| NM_053763 | XM_216386 |
| NM_053794 | XM_216565 |
| NM_053901 | XM_217197 |
| NM_053917 | XM_217239 |
| NM_053926 | XM_217651 |
| NM_053985 | XM_218195 |
| NM_053986 | XM_218337 |
| NM_053994 | XM_218523 |
| NM_054001 | XM_218617 |
| NM_057139 | XM_218939 |
| NM_057187 | XM_218977 |
| NM_058210 | XM_219785 |
| NM_058211 | XM_219885 |
| NM_130420 | XM_219948 |
| NM_131911 | XM_220357 |
| NM_133298 | XM_221497 |
| NM_133300 | XM_223190 |
| NM_133303 | XM_223535 |
| NM_133307 | XM_223781 |
| NM_133318 | XM_223786 |
| NM_133383 | XM_224337 |
| NM_133398 | XM_224944 |
| NM_133418 | XM_225147 |
| NM_133534 | XM_225160 |
| NM_133571 | XM_227217 |
| NM_133615 | XM_227444 |
| NM_134334 | XM_228164 |
| NM_134349 | XM_230284 |
| NM_134372 | XM_231620 |
| NM_134411 | XM_231749 |
| NM_138506 | XM_232194 |
| NM_138521 | XM_232343 |
| NM_139115 | XM_232354 |
| NM_145092 | XM_232364 |
| NM_145678 | XM_232732 |
| NM_145777 | XM_233141 |
| NM_147206 | XM_233403 |
| NM_147207 | XM_235057 |
| NM_152790 | XM_235558 |
| NM_153298 | XM_235566 |
| NM_172029 | XM_236020 |
| NM_172334 | XM_236227 |
| NM_173118 | XM_237371 |
| NM_173153 | XM_237415 |
| NM_173328 | XM_237754 |
| NM_175764 | XM_237907 |
| NM_181363 | XM_240311 |
| NM_181388 | XM_242062 |
| NM_181639 | XM_242644 |
| NM_182737 | XM_341494 |
| NM_199093 | XM_341495 |
| NM_199270 | XM_341548 |
| NM_199390 | XM_341578 |
| NM_199401 | XM_341584 |
| NM_203335 | XM_341605 |
| NM_207609 | XM_341957 |
| NM_212508 | XM_342007 |
| NM_212523 | XM_342291 |
| NM_213628 | XM_342317 |
| XM_213270 | XM_342545 |
| XM_213329 | XM_342653 |
| XM_213421 | XM_343055 |
| XM_213484 | XM_343117 |
| XM_213684 | XM_343205 |
| XM_213688 | XM_343259 |
| XM_214035 | XM_343274 |
| XM_214403 | XM_343332 |
| XM_214480 | XM_343395 |
| XM_214967 | XM_343468 |
| XM_214979 | XM_343552 |
| XM_215080 | XM_343773 |
| XM_215361 | XM_343975 |
| XM_215576 | XM_343986 |
| XM_215607 | XM_344112 |
| XM_215889 | XM_344409 |
| XM_215924 | XM_344785 |
| XM_216004 | XM_345825 |

TABLE 11-continued

CA3 - AI ANOVA INCREASE

XM_346854
XM_573810
XM_574618
XM_575585
XM_576312
XM_576519
UniGene ID

Rn.110441
Rn.129720

The genes in this set show abundance of expressed gene product(s) in the Aged Impaired population that are significantly increased, as determined by ANOVA, compared to those abundances in Young and Aged Unimpaired populations combined. Therefore, compounds useful in treating cognitive impairment selected using these genes should decrease the abundance or attenuate the function of the expressed gene products of these genes.

Example 12

An ANOVA was conducted on the probe set signal values for all present probe sets by combining two groups of animals and comparing them to the third group. An "AI ANOVA" was performed, where Aged Unimpaired were combined with Young and compared to Aged Impaired. Any probe sets having a p-value less than 0.05 were considered significantly changed and the genes or plurality of genes selected.

Microarray Results

Table 12 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 12

CA3 - AI ANOVA DECREASE

GENBANK ® ID

BI294968
BF284573
AW142828
L13193
BG663483
AF452727
AY316590
NM_001000716
NM_001004072
NM_001004078
NM_001004132
NM_001004233
NM_001005547
NM_001005554
NM_001005905
NM_001005908
NM_001006970
NM_001006997
NM_001007020
NM_001007608
NM_001007626
NM_001007714
NM_001007728
NM_001007742
NM_001008301
NM_001008323

TABLE 12-continued

CA3 - AI ANOVA DECREASE

NM_001008338
NM_001008339
NM_001008520
NM_001008558
NM_001008562
NM_001008766
NM_001008888
NM_001009180
NM_001009258
NM_001009424
NM_001009666
NM_001009677
NM_001009688
NM_001009967
NM_001010965
NM_001011969
NM_001011998
NM_001012060
NM_001012066
NM_001012078
NM_001012119
NM_001012187
NM_001012191
NM_001012468
NM_001012473
NM_001013034
NM_001013059
NM_001013153
NM_001013156
NM_001013178
NM_001013189
NM_001013207
NM_001013235
NM_001014792
NM_001014793
NM_001015003
NM_001017374
NM_001024765
NM_012500
NM_012517
NM_012526
NM_012583
NM_012598
NM_012647
NM_012663
NM_012734
NM_012736
NM_012757
NM_012839
NM_012892
NM_012923
NM_012932
NM_012952
NM_012953
NM_012956
NM_012960
NM_012963
NM_012985
NM_013002
NM_013011
NM_013019
NM_013038
NM_013048
NM_013081
NM_013102
NM_013111
NM_013127
NM_013134
NM_013177
NM_013214
NM_013223
NM_017025
NM_017029
NM_017039
NM_017040
NM_017042
NM_017102
NM_017107

TABLE 12-continued

CA3 - AI ANOVA DECREASE

| |
|---|
| NM_017136 |
| NM_017195 |
| NM_017232 |
| NM_017243 |
| NM_017246 |
| NM_017268 |
| NM_017270 |
| NM_017282 |
| NM_017318 |
| NM_017340 |
| NM_017343 |
| NM_017359 |
| NM_017364 |
| NM_019124 |
| NM_019131 |
| NM_019169 |
| NM_019196 |
| NM_019264 |
| NM_019277 |
| NM_019302 |
| NM_019304 |
| NM_019356 |
| NM_021655 |
| NM_021697 |
| NM_021758 |
| NM_021852 |
| NM_022008 |
| NM_022209 |
| NM_022262 |
| NM_022387 |
| NM_022498 |
| NM_022542 |
| NM_022585 |
| NM_022609 |
| NM_022674 |
| NM_022700 |
| NM_022865 |
| NM_022869 |
| NM_022939 |
| NM_023093 |
| NM_023950 |
| NM_023971 |
| NM_023975 |
| NM_024125 |
| NM_024152 |
| NM_024156 |
| NM_024378 |
| NM_024484 |
| NM_024486 |
| NM_030835 |
| NM_030856 |
| NM_031064 |
| NM_031138 |
| NM_031146 |
| NM_031151 |
| NM_031152 |
| NM_031237 |
| NM_031606 |
| NM_031639 |
| NM_031643 |
| NM_031655 |
| NM_031718 |
| NM_031720 |
| NM_031735 |
| NM_031742 |
| NM_031745 |
| NM_031757 |
| NM_031783 |
| NM_031785 |
| NM_031802 |
| NM_031811 |
| NM_031824 |
| NM_031987 |
| NM_032057 |
| NM_032614 |
| NM_033021 |
| NM_053346 |
| NM_053357 |
| NM_053409 |
| NM_053414 |
| NM_053420 |
| NM_053428 |
| NM_053439 |
| NM_053441 |
| NM_053484 |
| NM_053502 |
| NM_053518 |
| NM_053527 |
| NM_053581 |
| NM_053590 |
| NM_053605 |
| NM_053613 |
| NM_053622 |
| NM_053623 |
| NM_053638 |
| NM_053726 |
| NM_053747 |
| NM_053748 |
| NM_053752 |
| NM_053758 |
| NM_053764 |
| NM_053772 |
| NM_053812 |
| NM_053842 |
| NM_053856 |
| NM_053868 |
| NM_053888 |
| NM_053893 |
| NM_053912 |
| NM_053927 |
| NM_053948 |
| NM_053974 |
| NM_053979 |
| NM_053996 |
| NM_054002 |
| NM_054003 |
| NM_057107 |
| NM_057141 |
| NM_057196 |
| NM_057210 |
| NM_080777 |
| NM_080780 |
| NM_080886 |
| NM_080887 |
| NM_080902 |
| NM_130423 |
| NM_130746 |
| NM_130749 |
| NM_130894 |
| NM_131904 |
| NM_133313 |
| NM_133320 |
| NM_133402 |
| NM_133415 |
| NM_133427 |
| NM_133566 |
| NM_133589 |
| NM_134331 |
| NM_134383 |
| NM_134404 |
| NM_138519 |
| NM_138833 |
| NM_138839 |
| NM_138856 |
| NM_138883 |
| NM_139097 |
| NM_139098 |
| NM_139106 |
| NM_139254 |
| NM_145184 |
| NM_147211 |
| NM_152935 |
| NM_153297 |
| NM_153630 |
| NM_153735 |
| NM_171990 |

TABLE 12-continued

CA3 - AI ANOVA DECREASE

NM_171994
NM_172072
NM_173102
NM_173146
NM_173290
NM_177425
NM_177929
NM_178091
NM_181090
NM_181626
NM_182668
NM_182814
NM_182819
NM_183052
NM_183332
NM_184050
NM_184051
NM_198132
NM_198732
NM_198758
NM_198760
NM_198765
NM_198787
NM_198788
NM_199385
NM_199395
NM_199405
NM_199410
NM_199500
NM_207617
NM_212494
NM_212519
NM_212520
XM_213362
XM_213426
XM_213487
XM_213564
XM_213571
XM_213679
XM_213765
XM_213782
XM_213840
XM_214003
XM_214108
XM_214147
XM_214241
XM_214475
XM_214485
XM_214491
XM_214583
XM_214646
XM_214701
XM_214969
XM_215251
XM_215286
XM_215416
XM_215549
XM_215570
XM_215612
XM_216158
XM_216265
XM_216378
XM_216641
XM_216893
XM_217105
XM_217209
XM_217560
XM_217592
XM_217868
XM_218620
XM_218660
XM_219377
XM_219525
XM_219939
XM_220230
XM_220281
XM_220717
XM_220754
XM_221212
XM_221888
XM_221910
XM_222669
XM_222717
XM_223729
XM_224271
XM_225078
XM_226561
XM_227301
XM_228345
XM_230495
XM_231271
XM_231803
XM_232220
XM_232739
XM_232901
XM_233485
XM_233529
XM_234483
XM_234555
XM_235185
XM_235878
XM_236698
XM_237808
XM_238280
XM_238770
XM_239761
XM_340775
XM_340872
XM_340889
XM_340921
XM_340999
XM_341288
XM_341374
XM_341448
XM_341700
XM_341822
XM_341930
XM_342149
XM_342174
XM_342217
XM_342300
XM_342306
XM_342312
XM_342493
XM_342534
XM_342553
XM_342582
XM_342600
XM_342612
XM_342679
XM_342812
XM_342894
XM_342920
XM_343154
XM_343389
XM_343459
XM_343557
XM_343761
XM_343776
XM_344231
XM_344434
XM_344594
XM_573052
XM_573063
XM_573256
XM_574916
XM_578542
XM_579413

UniGene ID

Rn.128732
Rn.15446
Rn.23342
Rn.25029
Rn.92383

The genes in this set show abundance of expressed gene product(s) in the Aged Impaired population that are significantly decreased, as determined by ANOVA, compared to those abundances in Young and Aged Unimpaired populations combined. Therefore, compounds useful in treating cognitive impairment selected using these genes should increase the abundance or enhance the function of the expressed gene products of these genes.

Example 13

An ANOVA was conducted on the probe set signal values for all present probe sets by combining two groups of animals and comparing them to the third group. An "AU ANOVA" was performed, where Aged Impaired were combined with Young and compared to Aged Unimpaired. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 13 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 13

| CA3 - AU ANOVA POSITIVE CORRELATION |
|---|
| GENBANK ® ID |
| BF419095 |
| BF420440 |
| NM_001005889 |
| NM_001009665 |
| NM_001009825 |
| NM_001011974 |
| NM_001012038 |
| NM_001012061 |
| NM_001012150 |
| NM_001012183 |
| NM_001012504 |
| NM_001013128 |
| NM_012504 |
| NM_012518 |
| NM_012527 |
| NM_012574 |
| NM_012633 |
| NM_012836 |
| NM_012920 |
| NM_013029 |
| NM_013065 |
| NM_013066 |
| NM_013126 |
| NM_013135 |
| NM_017065 |
| NM_017066 |
| NM_017211 |
| NM_017213 |
| NM_017242 |
| NM_017262 |
| NM_017290 |
| NM_017304 |
| NM_017327 |
| NM_019128 |
| NM_019204 |
| NM_019275 |

TABLE 13-continued

| CA3 - AU ANOVA POSITIVE CORRELATION |
|---|
| NM_019351 |
| NM_019375 |
| NM_020075 |
| NM_020088 |
| NM_021597 |
| NM_021678 |
| NM_021767 |
| NM_021835 |
| NM_021847 |
| NM_022254 |
| NM_022380 |
| NM_022690 |
| NM_022703 |
| NM_022850 |
| NM_022946 |
| NM_023020 |
| NM_023983 |
| NM_024366 |
| NM_024397 |
| NM_030871 |
| NM_031028 |
| NM_031036 |
| NM_031081 |
| NM_031515 |
| NM_031535 |
| NM_031608 |
| NM_031665 |
| NM_031743 |
| NM_032613 |
| NM_053311 |
| NM_053369 |
| NM_053424 |
| NM_053457 |
| NM_053475 |
| NM_053508 |
| NM_053589 |
| NM_053859 |
| NM_053878 |
| NM_053891 |
| NM_053910 |
| NM_057116 |
| NM_080482 |
| NM_080583 |
| NM_080904 |
| NM_131907 |
| NM_133395 |
| NM_133579 |
| NM_134413 |
| NM_138502 |
| NM_138509 |
| NM_138896 |
| NM_139060 |
| NM_139189 |
| NM_139217 |
| NM_144756 |
| NM_148891 |
| NM_153309 |
| NM_153317 |
| NM_173152 |
| NM_181550 |
| XM_213626 |
| XM_213746 |
| XM_213969 |
| XM_214253 |
| XM_215403 |
| XM_215467 |
| XM_215578 |
| XM_215919 |
| XM_215990 |
| XM_217021 |
| XM_218828 |
| XM_220232 |
| XM_221426 |
| XM_223205 |
| XM_223837 |
| XM_224474 |
| XM_227623 |
| XM_228644 |

TABLE 13-continued

CA3 - AU ANOVA POSITIVE CORRELATION

XM_233798
XM_234901
XM_235179
XM_236268
XM_236362
XM_237241
XM_238072
XM_238336
XM_241981
XM_340747
XM_341081
XM_341104
XM_341201
XM_341341
XM_341857
XM_341961
XM_342521
XM_342535
XM_342682
XM_342684
XM_342808
XM_343059
XM_343109
XM_343157
XM_343427
XM_343483
XM_343513
XM_343582
XM_343630
XM_343736
XM_343764
XM_573205
XM_573259
XM_573634
XM_576311
XM_579869
UniGene ID Rn.122667
Rn.78244

The genes in this set show abundance of expressed gene product(s) in the Aged Unimpaired population that are significantly decreased, as determined by ANOVA, compared to those abundances in Young and Aged Impaired populations combined. In addition, the abundance of expressed gene product(s) in the aged animals positively correlate with learning index of the animals, such that poorer learners have higher abundances of expressed gene products of the selected genes. Therefore, compounds useful in treating cognitive impairment selected using these genes should decrease the abundance or attenuate the function of the expressed gene products of these genes.

Example 14

An ANOVA was conducted on the probe set signal values for all present probe sets by combining two groups of animals and comparing them to the third group. An "AU ANOVA" was performed, where Aged Impaired were combined with Young and compared to Aged Unimpaired. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 14 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 14

CA3 - AU ANOVA NEGATIVE CORRELATION GENBANK ® ID

NM_001003978
NM_001004075
NM_001006991
NM_001011905
NM_001011992
NM_001012160
NM_001013206
NM_001013224
NM_001013234
NM_001013873
NM_012645
NM_013154
NM_019364
NM_020308
NM_022210
NM_022394
NM_022541
NM_024374
NM_024385
NM_031062
NM_031345
NM_031596
NM_031978
NM_032079
NM_053295
NM_053442
NM_053539
NM_053642
NM_053713
NM_053714
NM_053787
NM_130413
NM_134326
NM_134456
NM_145778
NM_145785
NM_171995
NM_173117
NM_175579
NM_182816
XM_213658
XM_213993
XM_214730
XM_214890
XM_215637
XM_215908
XM_216380
XM_216661
XM_217050
XM_219297
XM_221050
XM_224588
XM_231052
XM_232168
XM_232860
XM_233767
XM_235051
XM_236210
XM_237828
XM_243652
XM_340911
XM_341750
XM_342032
XM_342044
XM_342396
XM_342578
XM_345160
XM_578548

The genes in this set show abundance of expressed gene product(s) in the Aged Unimpaired population that are significantly increased, as determined by ANOVA, compared to those abundances in Young and Aged Impaired populations combined. In addition, the abundance of expressed gene product(s) in the aged animals negatively correlate with learning index of the animals, such that poorer learners have lower abundances of expressed gene products of the selected genes. Therefore, compounds useful in treating cognitive impairment selected using these genes should increase the abundance or enhance the function of the expressed gene products of these genes.

Example 15

An ANOVA was conducted on the probe set signal values for all present probe sets by combining two groups of animals and comparing them to the third group. An "AU ANOVA" was performed, where Aged Impaired were combined with Young and compared to Aged Unimpaired. Any probe sets having a p-value less than 0.05 were considered significantly changed and the genes or plurality of genes selected.

Microarray Results

Table 15 shows the genes that were identified as being associated with cognitive impairment in this experiment. The reference sequence transcript ID (GENBANK®) number for the exemplar sequence) was used to identify genes considered significantly changed. When this exemplar ID was not available, a UniGene identifier was used in conjunction with the GENBANK® accession number.

TABLE 15

| CA3 - AU ANOVA INCREASE |
|---|
| GENBANK ® ID |
| BF287008 |
| AF442812 |
| AY597251 |
| NM_001002854 |
| NM_001004199 |
| NM_001004443 |
| NM_001005557 |
| NM_001006602 |
| NM_001006976 |
| NM_001007686 |
| NM_001007734 |
| NM_001008309 |
| NM_001008515 |
| NM_001008521 |
| NM_001009349 |
| NM_001009369 |
| NM_001009632 |
| NM_001009641 |
| NM_001009645 |
| NM_001009973 |
| NM_001011896 |
| NM_001011948 |
| NM_001012021 |
| NM_001012133 |
| NM_001013033 |
| NM_001013082 |
| NM_001013213 |
| NM_001013223 |
| NM_001013233 |
| NM_012512 |
| NM_012550 |
| NM_012562 |
| NM_012656 |
| NM_012731 |
| NM_012857 |
| NM_012870 |
| NM_012887 |

TABLE 15-continued

| CA3 - AU ANOVA INCREASE |
|---|
| NM_012895 |
| NM_012904 |
| NM_012935 |
| NM_012939 |
| NM_012940 |
| NM_012988 |
| NM_013001 |
| NM_013022 |
| NM_013055 |
| NM_017116 |
| NM_017264 |
| NM_019238 |
| NM_021763 |
| NM_021846 |
| NM_021863 |
| NM_021997 |
| NM_022197 |
| NM_022219 |
| NM_022282 |
| NM_022515 |
| NM_022599 |
| NM_022626 |
| NM_022941 |
| NM_022949 |
| NM_024144 |
| NM_024150 |
| NM_024377 |
| NM_024388 |
| NM_031078 |
| NM_031083 |
| NM_031094 |
| NM_031122 |
| NM_031622 |
| NM_031640 |
| NM_031721 |
| NM_031728 |
| NM_031751 |
| NM_032612 |
| NM_033096 |
| NM_052809 |
| NM_053455 |
| NM_053541 |
| NM_053580 |
| NM_053584 |
| NM_053698 |
| NM_053774 |
| NM_053826 |
| NM_053832 |
| NM_053884 |
| NM_053946 |
| NM_053998 |
| NM_130409 |
| NM_133314 |
| NM_133387 |
| NM_133548 |
| NM_133552 |
| NM_134389 |
| NM_138508 |
| NM_138846 |
| NM_138847 |
| NM_138907 |
| NM_139083 |
| NM_139094 |
| NM_145783 |
| NM_148890 |
| NM_172324 |
| NM_173323 |
| NM_175756 |
| NM_175762 |
| NM_177933 |
| NM_181432 |
| NM_181628 |
| NM_182844 |
| NM_183331 |
| NM_183402 |
| NM_199111 |
| NM_201988 |
| U31866 |

TABLE 15-continued

CA3 - AU ANOVA INCREASE

XM_213324
XM_213346
XM_213418
XM_213823
XM_214958
XM_215037
XM_215469
XM_215528
XM_215812
XM_215858
XM_216316
XM_216757
XM_218041
XM_218759
XM_220606
XM_220736
XM_221077
XM_222152
XM_223508
XM_223684
XM_224971
XM_225039
XM_225644
XM_226769
XM_228197
XM_228305
XM_232202
XM_232466
XM_232608
XM_233138
XM_233341
XM_233611
XM_233820
XM_233944
XM_234328
XM_234441
XM_238163
XM_242005
XM_242556
XM_340943
XM_341066
XM_341251
XM_341346
XM_341444
XM_341644
XM_341688
XM_342002
XM_342154
XM_342470
XM_343126
XM_343318
XM_345114
XM_574371
XM_579460
XM_579522

UniGene ID

Rn.14733

The genes in this set show abundance of expressed gene product(s) in the Aged Unimpaired population that are significantly increased, as determined by ANOVA, compared to those abundances in Young and Aged Impaired populations combined. Therefore, compounds useful in treating cognitive impairment selected using these genes should increase the abundance or enhance the function of the expressed gene products of these genes.

Example 16

An ANOVA was conducted on the probe set signal values for all present probe sets by combining two groups of animals and comparing them to the third group. An "AU ANOVA" was performed, where Aged Impaired were combined with Young and compared to Aged Unimpaired. Any probe sets having a p-value less than 0.05 were considered significantly changed and the genes or plurality of genes selected.

Microarray Results

Table 16 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 16

CA3 - AU ANOVA DECREASE

GENBANK ® ID

AI171809
BI395698
NM_001004083
NM_001006971
NM_001007616
NM_001008519
NM_001008694
NM_001009681
NM_001011930
NM_001011938
NM_001011939
NM_001012004
NM_001012175
NM_001012189
NM_001012345
NM_001013045
NM_001013094
NM_001013096
NM_001013138
NM_001013186
NM_012506
NM_012508
NM_012545
NM_012569
NM_012581
NM_012673
NM_012686
NM_012756
NM_012798
NM_012820
NM_012830
NM_012841
NM_012918
NM_013116
NM_013181
NM_013189
NM_016990
NM_017093
NM_017094
NM_017131
NM_017204
NM_017253
NM_017254
NM_017259
NM_017298
NM_017312
NM_019159
NM_019208
NM_019295
NM_019306
NM_019343
NM_020094
NM_021748
NM_021775
NM_021859
NM_022193
NM_022206
NM_022217
NM_022252
NM_022267
NM_022382
NM_022384

TABLE 16-continued

CA3 - AU ANOVA DECREASE

| |
|---|
| NM_022589 |
| NM_022606 |
| NM_022666 |
| NM_022668 |
| NM_022675 |
| NM_022855 |
| NM_022864 |
| NM_022945 |
| NM_023988 |
| NM_024000 |
| NM_024146 |
| NM_024394 |
| NM_030858 |
| NM_030862 |
| NM_031008 |
| NM_031315 |
| NM_031353 |
| NM_031568 |
| NM_031657 |
| NM_031667 |
| NM_031821 |
| NM_031831 |
| NM_053335 |
| NM_053440 |
| NM_053464 |
| NM_053503 |
| NM_053553 |
| NM_053675 |
| NM_053721 |
| NM_053724 |
| NM_053777 |
| NM_053788 |
| NM_053811 |
| NM_053864 |
| NM_053894 |
| NM_053895 |
| NM_053903 |
| NM_053924 |
| NM_053931 |
| NM_053997 |
| NM_057118 |
| NM_057125 |
| NM_057140 |
| NM_057152 |
| NM_057201 |
| NM_080885 |
| NM_133406 |
| NM_133419 |
| NM_133535 |
| NM_133567 |
| NM_133582 |
| NM_134366 |
| NM_134376 |
| NM_134398 |
| NM_134455 |
| NM_134458 |
| NM_134461 |
| NM_139329 |
| NM_139330 |
| NM_139333 |
| NM_145089 |
| NM_145090 |
| NM_145680 |
| NM_147209 |
| NM_148889 |
| NM_173105 |
| NM_175708 |
| NM_175754 |
| NM_175760 |
| NM_175761 |
| NM_175869 |
| NM_177481 |
| NM_178106 |
| NM_181478 |
| NM_181822 |
| NM_182842 |
| NM_199372 |
| NM_199397 |
| NM_212458 |
| XM_213574 |
| XM_213777 |
| XM_213842 |
| XM_213925 |
| XM_213954 |
| XM_213963 |
| XM_214751 |
| XM_214780 |
| XM_214888 |
| XM_215182 |
| XM_215371 |
| XM_215655 |
| XM_215963 |
| XM_215984 |
| XM_216152 |
| XM_216228 |
| XM_216349 |
| XM_216398 |
| XM_216725 |
| XM_216965 |
| XM_217078 |
| XM_217283 |
| XM_217381 |
| XM_217388 |
| XM_218615 |
| XM_220055 |
| XM_220062 |
| XM_220224 |
| XM_220315 |
| XM_222103 |
| XM_222177 |
| XM_222245 |
| XM_222773 |
| XM_224713 |
| XM_225468 |
| XM_227282 |
| XM_227409 |
| XM_227428 |
| XM_228753 |
| XM_230814 |
| XM_230899 |
| XM_232351 |
| XM_233737 |
| XM_233839 |
| XM_235064 |
| XM_235156 |
| XM_235496 |
| XM_235662 |
| XM_236009 |
| XM_236735 |
| XM_238398 |
| XM_340886 |
| XM_341091 |
| XM_341248 |
| XM_341500 |
| XM_341807 |
| XM_343114 |
| XM_343175 |
| XM_343339 |
| XM_343839 |
| XM_345861 |
| XM_573915 |
| XM_575018 |
| XM_575080 |
| XM_579523 |
| XM_579696 |
| UniGene ID |
| Rn.129749 |
| Rn.116507 |

The genes in this set show abundance of expressed gene product(s) in the Aged Unimpaired population that are significantly decreased, as determined by ANOVA, compared to those abundances in Young and Aged Impaired populations combined. Therefore, compounds useful in treating cognitive impairment selected using these genes should decrease the abundance or attenuate the function of the expressed gene products of these genes.

Example 17

An ANOVA was conducted on the probe set signal values for all present probe sets by combining two groups of animals and comparing them to the third group. An "AI ANOVA" was performed, where Aged Unimpaired were combined with Young and compared to Aged Impaired. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 17 shows the genes that were identified as being associated with cognitive impairment in this experiment. The reference sequence transcript ID (GENBANK®) number for the exemplar sequence) was used to identify genes considered significantly changed. When this exemplar ID was not available, a UniGene identifier was used in conjunction with the GENBANK® accession number.

TABLE 17

| DG - AI ANOVA POSITIVE CORRELATION GENBANK ® ID |
|---|
| NM_001001516 |
| NM_001004080 |
| NM_001004081 |
| NM_001004199 |
| NM_001004209 |
| NM_001004225 |
| NM_001004247 |
| NM_001004273 |
| NM_001004275 |
| NM_001005539 |
| NM_001006987 |
| NM_001006998 |
| NM_001007684 |
| NM_001007691 |
| NM_001008312 |
| NM_001008324 |
| NM_001008374 |
| NM_001009618 |
| NM_001009677 |
| NM_001009708 |
| NM_001011890 |
| NM_001011910 |
| NM_001011946 |
| NM_001011999 |
| NM_001012137 |
| NM_001012149 |
| NM_001012235 |
| NM_001013105 |
| NM_001013167 |
| NM_001013175 |
| NM_001013206 |
| NM_001013213 |
| NM_001013874 |
| NM_001017385 |
| NM_012543 |
| NM_012577 |
| NM_012628 |
| NM_012686 |
| NM_012701 |
| NM_012749 |
| NM_012777 |
| NM_012781 |
| NM_012788 |

TABLE 17-continued

| DG - AI ANOVA POSITIVE CORRELATION GENBANK ® ID |
|---|
| NM_012820 |
| NM_012893 |
| NM_013000 |
| NM_013015 |
| NM_013107 |
| NM_013135 |
| NM_017051 |
| NM_017052 |
| NM_017068 |
| NM_017075 |
| NM_017109 |
| NM_017142 |
| NM_017181 |
| NM_017232 |
| NM_017288 |
| NM_019124 |
| NM_019131 |
| NM_019159 |
| NM_019204 |
| NM_019257 |
| NM_019359 |
| NM_020308 |
| NM_021766 |
| NM_021869 |
| NM_022400 |
| NM_022499 |
| NM_022500 |
| NM_022502 |
| NM_022523 |
| NM_022539 |
| NM_022592 |
| NM_022595 |
| NM_022596 |
| NM_022617 |
| NM_022637 |
| NM_022853 |
| NM_024359 |
| NM_024400 |
| NM_030859 |
| NM_031035 |
| NM_031049 |
| NM_031057 |
| NM_031101 |
| NM_031105 |
| NM_031120 |
| NM_031357 |
| NM_031514 |
| NM_031576 |
| NM_031587 |
| NM_031599 |
| NM_031632 |
| NM_031654 |
| NM_031725 |
| NM_031798 |
| NM_032612 |
| NM_053295 |
| NM_053418 |
| NM_053588 |
| NM_053598 |
| NM_053612 |
| NM_053670 |
| NM_053698 |
| NM_053777 |
| NM_053870 |
| NM_053945 |
| NM_057114 |
| NM_080888 |
| NM_130416 |
| NM_130420 |
| NM_130894 |
| NM_133551 |
| NM_133557 |
| NM_134367 |
| NM_134370 |
| NM_138508 |
| NM_138900 |
| NM_138917 |

TABLE 17-continued

DG - AI ANOVA POSITIVE CORRELATION
GENBANK® ID

NM_139107
NM_139186
NM_147210
NM_153469
NM_172063
NM_172068
NM_173111
NM_175578
NM_175582
NM_199119
NM_207591
NM_207602
XM_214172
XM_214383
XM_214518
XM_214588
XM_214968
XM_215069
XM_215371
XM_215754
XM_215939
XM_216641
XM_216740
XM_216872
XM_218425
XM_219374
XM_220264
XM_220699
XM_221387
XM_223190
XM_224944
XM_225726
XM_227066
XM_228114
XM_230637
XM_232323
XM_240330
XM_341249
XM_341785
XM_341957
XM_342092
XM_342318
XM_342757
XM_342887
XM_343119
XM_343318
XM_343773
XM_345674
XM_346244
XM_346854
XM_573772
XM_574670
XM_579675

The genes in this set show abundance of expressed gene product(s) in the Aged Impaired population that are significantly increased, as determined by ANOVA, compared to those abundances in Young and Aged Unimpaired populations combined. In addition, the abundance of expressed gene product(s) in the aged animals positively correlate with learning index of the animals, such that poorer learners have higher abundances of expressed gene products of the selected genes. Therefore, compounds useful in treating cognitive impairment selected using these genes should decrease the abundance or attenuate the function of the expressed gene products of these genes.

Example 18

An ANOVA was conducted on the probe set signal values for all present probe sets by combining two groups of animals and comparing them to the third group. An "AI ANOVA" was performed, where Aged Unimpaired were combined with Young and compared to Aged Impaired. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 18 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 18

DG - AI ANOVA NEGATIVE CORRELATION

GENBANK® ID

AI043800
NM_001001512
NM_001004208
NM_001004446
NM_001008353
NM_001008520
NM_001011923
NM_001012025
NM_001012072
NM_001013873
NM_001015021
NM_012590
NM_012609
NM_012727
NM_012769
NM_012874
NM_012959
NM_012994
NM_013083
NM_013131
NM_017290
NM_019128
NM_019347
NM_020089
NM_021758
NM_021842
NM_022281
NM_022289
NM_022297
NM_022387
NM_022506
NM_022541
NM_022546
NM_022599
NM_022934
NM_022938
NM_023977
NM_024373
NM_024375
NM_031016
NM_031123
NM_031510
NM_031613
NM_031685
NM_031694
NM_031730
NM_053321
NM_053328
NM_053349
NM_053358
NM_053360
NM_053625
NM_053669
NM_053787
NM_053883

TABLE 18-continued

DG - AI ANOVA NEGATIVE CORRELATION

NM_080899
NM_080902
NM_131907
NM_138506
NM_138850
NM_138911
NM_138914
NM_139192
NM_139259
NM_144758
NM_145184
NM_153317
NM_172034
NM_172062
NM_173117
NM_173119
NM_173137
NM_176857
NM_181626
NM_199106
NM_201560
XM_213762
XM_213963
XM_213969
XM_215883
XM_215890
XM_218226
XM_218515
XM_219879
XM_220708
XM_220992
XM_222103
XM_222717
XM_222773
XM_224733
XM_225895
XM_231148
XM_232413
XM_234011
XM_234470
XM_236210
XM_236614
XM_241375
XM_341089
XM_341091
XM_341106
XM_341310
XM_342044
XM_342325
XM_342612
XM_342643
XM_343263
XM_343442
XM_344785
XM_345981
XM_574916
XM_576437
UniGene ID Rn.18726

The genes in this set show abundance of expressed gene product(s) in the Aged Impaired population that are significantly decreased, as determined by ANOVA, compared to those abundances in Young and Aged Unimpaired populations combined. In addition, the abundance of expressed gene product(s) in the aged animals negatively correlate with learning index of the animals, such that poorer learners have lower abundances of expressed gene products of the selected genes. Therefore, compounds useful in treating cognitive impairment selected using these genes should increase the abundance or enhance the function of the expressed gene products of these genes.

Example 19

An ANOVA was conducted on the probe set signal values for all present probe sets by combining two groups of animals and comparing them to the third group. An "AI ANOVA" was performed, where Aged Unimpaired were combined with Young and compared to Aged Impaired. Any probe sets having a p-value less than 0.05 were considered significantly changed and the genes or plurality of genes selected.

Microarray Results

Table 19 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 19

DG - AI ANOVA INCREASE

GENBANK ® ID

BI303253
BF567886
BE112341
AW142720
AI231999
BF398752
AF030087
AY190520
NM_001002016
NM_001004076
NM_001004099
NM_001004218
NM_001005907
NM_001006989
NM_001007557
NM_001007625
NM_001007654
NM_001007712
NM_001007729
NM_001007749
NM_001008287
NM_001008725
NM_001008767
NM_001008768
NM_001009474
NM_001009502
NM_001009662
NM_001009669
NM_001009719
NM_001011985
NM_001012004
NM_001012088
NM_001012147
NM_001012162
NM_001013044
NM_001013112
NM_001013121
NM_001013179
NM_001013194
NM_001013210
NM_001013233
NM_001013249
NM_012512
NM_012546
NM_012562
NM_012581
NM_012637
NM_012663
NM_012762
NM_012844
NM_012862
NM_012913
NM_012925

TABLE 19-continued

DG - AI ANOVA INCREASE

| |
|---|
| NM_012939 |
| NM_012971 |
| NM_012974 |
| NM_012985 |
| NM_012992 |
| NM_012993 |
| NM_013044 |
| NM_013070 |
| NM_013122 |
| NM_013137 |
| NM_013146 |
| NM_013156 |
| NM_013194 |
| NM_017060 |
| NM_017116 |
| NM_017125 |
| NM_017132 |
| NM_017175 |
| NM_017192 |
| NM_017200 |
| NM_017280 |
| NM_017307 |
| NM_017320 |
| NM_017351 |
| NM_019156 |
| NM_019232 |
| NM_019249 |
| NM_019253 |
| NM_019289 |
| NM_019312 |
| NM_019363 |
| NM_019904 |
| NM_019906 |
| NM_020073 |
| NM_020074 |
| NM_020075 |
| NM_020088 |
| NM_020099 |
| NM_021690 |
| NM_021769 |
| NM_021909 |
| NM_022210 |
| NM_022226 |
| NM_022270 |
| NM_022382 |
| NM_022390 |
| NM_022526 |
| NM_022530 |
| NM_022531 |
| NM_022601 |
| NM_022638 |
| NM_022692 |
| NM_023967 |
| NM_024155 |
| NM_024353 |
| NM_024358 |
| NM_024369 |
| NM_030826 |
| NM_030831 |
| NM_030863 |
| NM_031013 |
| NM_031099 |
| NM_031114 |
| NM_031140 |
| NM_031328 |
| NM_031509 |
| NM_031511 |
| NM_031525 |
| NM_031544 |
| NM_031593 |
| NM_031677 |
| NM_031683 |
| NM_031778 |
| NM_031789 |
| NM_031797 |
| NM_031818 |
| NM_032067 |
| NM_032416 |
| NM_052983 |
| NM_053314 |
| NM_053356 |
| NM_053404 |
| NM_053411 |
| NM_053455 |
| NM_053485 |
| NM_053516 |
| NM_053560 |
| NM_053583 |
| NM_053584 |
| NM_053592 |
| NM_053618 |
| NM_053714 |
| NM_053783 |
| NM_053886 |
| NM_053896 |
| NM_053927 |
| NM_053936 |
| NM_053999 |
| NM_05710 |
| NM_057197 |
| NM_080480 |
| NM_080584 |
| NM_080691 |
| NM_080698 |
| NM_130409 |
| NM_133296 |
| NM_133298 |
| NM_133305 |
| NM_133605 |
| NM_134449 |
| NM_138542 |
| NM_138855 |
| NM_139110 |
| NM_139216 |
| NM_139327 |
| NM_153297 |
| NM_153628 |
| NM_172029 |
| NM_172033 |
| NM_172325 |
| NM_173118 |
| NM_173123 |
| NM_175756 |
| NM_177426 |
| NM_181365 |
| NM_183328 |
| NM_198134 |
| NM_198786 |
| NM_199093 |
| NM_199115 |
| NM_199118 |
| NM_199378 |
| NM_199388 |
| NM_207598 |
| NM_212463 |
| NM_212501 |
| XM_213972 |
| XM_213995 |
| XM_214441 |
| XM_214656 |
| XM_214927 |
| XM_215095 |
| XM_215222 |
| XM_215285 |
| XM_215576 |
| XM_215733 |
| XM_215840 |
| XM_215935 |
| XM_215942 |
| XM_215994 |
| XM_216410 |
| XM_217061 |
| XM_217152 |
| XM_217154 |
| XM_217271 |
| XM_217283 |

TABLE 19-continued

DG - AI ANOVA INCREASE

XM_217297
XM_217367
XM_217690
XM_218292
XM_218816
XM_220567
XM_220736
XM_220810
XM_220982
XM_222476
XM_223524
XM_223583
XM_223690
XM_223781
XM_224969
XM_225014
XM_225259
XM_226016
XM_226211
XM_228073
XM_231620
XM_233138
XM_233345
XM_235518
XM_236380
XM_236675
XM_237371
XM_237825
XM_242644
XM_243637
XM_341107
XM_341227
XM_341352
XM_341574
XM_341578
XM_341653
XM_341657
XM_341664
XM_341790
XM_341948
XM_342007
XM_342048
XM_342409
XM_342542
XM_342591
XM_342759
XM_343006
XM_343065
XM_343126
XM_343166
XM_343174
XM_343198
XM_343332
XM_343564
XM_343570
XM_343845
XM_346594
XM_574170
XM_574618
XM_575585

UniGene ID

Rn.105382
Rn.108166
Rn.114169
Rn.128732
Rn.24825
Rn.48866

The genes in this set show abundance of expressed gene product(s) in the Aged Impaired population that are significantly increased, as determined by ANOVA, compared to those abundances in Young and Aged Unimpaired populations combined. Therefore, compounds useful in treating cognitive impairment selected using these genes should decrease the abundance or attenuate the function of the expressed gene products of these genes.

Example 20

An ANOVA was conducted on the probe set signal values for all present probe sets by combining two groups of animals and comparing them to the third group. An "AI ANOVA" was performed, where Aged Unimpaired were combined with Young and compared to Aged Impaired. Any probe sets having a p-value less than 0.05 were considered significantly changed and the genes or plurality of genes selected.

Microarray Results

Table 20 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 20

DG - AI ANOVA DECREASE

GENBANK ® ID

BG381750
BM391206
BG374818
AI406842
BM388719
BE103926
NM_001001508
NM_001002819
NM_001003978
NM_001004082
NM_001004133
NM_001005765
NM_001006970
NM_001007680
NM_001007742
NM_001008299
NM_001008317
NM_001009679
NM_001009704
NM_001012017
NM_001012131
NM_001012150
NM_001012197
NM_001012214
NM_001013035
NM_001013092
NM_001013128
NM_001014187
NM_012585
NM_012916
NM_012934
NM_013002
NM_013060
NM_013066
NM_013111
NM_013192
NM_017011
NM_017093
NM_017105
NM_017155
NM_017171
NM_017215
NM_017303
NM_017311
NM_017318
NM_017328
NM_017357
NM_017359
NM_019356
NM_021597

TABLE 20-continued

DG - AI ANOVA DECREASE

NM_021849
NM_022188
NM_022254
NM_022262
NM_022264
NM_022532
NM_022548
NM_022615
NM_022668
NM_022678
NM_022688
NM_022962
NM_024484
NM_030842
NM_030846
NM_030871
NM_031005
NM_031054
NM_031325
NM_031563
NM_031573
NM_031596
NM_031727
NM_031777
NM_031977
NM_052801
NM_053492
NM_053589
NM_053642
NM_053729
NM_053779
NM_053801
NM_053834
NM_053851
NM_053891
NM_053931
NM_057208
NM_080482
NM_080776
NM_080781
NM_130749
NM_133425
NM_133562
NM_133568
NM_133596
NM_134376
NM_134395
NM_134398
NM_138849
NM_138922
NM_139091
NM_145676
NM_145783
NM_153318
NM_172008
NM_173133
NM_173337
NM_183331
NM_198787
NM_207590
XM_213610
XM_213765
XM_214155
XM_214690
XM_214856
XM_215134
XM_215573
XM_215896
XM_216047
XM_216227
XM_217063
XM_217115
XM_217147
XM_217464
XM_218660
XM_219576
XM_220992
XM_221888

TABLE 20-continued

DG - AI ANOVA DECREASE

XM_221910
XM_221962
XM_222946
XM_223729
XM_224335
XM_224588
XM_224707
XM_224713
XM_225138
XM_225468
XM_226888
XM_232197
XM_232760
XM_235705
XM_237288
XM_239171
XM_340739
XM_340856
XM_340999
XM_341112
XM_341337
XM_341683
XM_341688
XM_341803
XM_342134
XM_342763
XM_342854
XM_342920
XM_343358
XM_343395
XM_343469
XM_343910
XM_344063
XM_344594
XM_344744
NM_134383
NM_053410
XM_579362

UniGene ID

Rn.101929
Rn.11688
Rn.39092
Rn.6994
Rn.8562
Rn.98343

The genes in this set show abundance of expressed gene product(s) in the Aged Impaired population that are significantly decreased, as determined by ANOVA, compared to those abundances in Young and Aged Unimpaired populations combined. Therefore, compounds useful in treating cognitive impairment selected using these genes should increase the abundance or enhance the function of the expressed gene products of these genes.

Example 21

An ANOVA was conducted on the probe set signal values for all present probe sets by combining two groups of animals and comparing them to the third group. An "AU ANOVA" was performed, where Aged Impaired were combined with Young and compared to Aged Unimpaired. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 21 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 21

DG - AU ANOVA POSITIVE CORRELATION
GENBANK ® ID

AF022087
NM_001001514
NM_001005534
NM_001005547
NM_001008301
NM_001009825
NM_001010953
NM_001011895
NM_001011920
NM_001011941
NM_001011990
NM_012634
NM_017346
NM_019379
NM_022675
NM_022936
NM_031034
NM_031575
NM_031631
NM_031735
NM_052981
NM_053440
NM_053639
NM_053804
NM_053842
NM_053871
NM_053965
NM_057141
NM_080478
NM_130406
NM_133313
NM_152935
NM_183402
NM_184049
NM_198785
NM_199380
X76489
XM_213421
XM_213484
XM_213782
XM_213824
XM_214035
XM_214420
XM_216349
XM_216661
XM_220574
XM_220754
XM_227749
XM_232531
XM_232809
XM_233341
XM_236181
XM_236992
XM_340970
XM_341550
XM_341666
XM_341796
XM_342300
XM_342592
XM_342686
XM_343513

The genes in this set show abundance of expressed gene product(s) in the Aged Unimpaired population that are significantly decreased, as determined by ANOVA, compared to those abundances in Young and Aged Impaired populations combined. In addition, the abundance of expressed gene product(s) in the aged animals positively correlate with learning index of the animals, such that poorer learners have higher abundances of expressed gene products of the selected genes. Therefore, compounds useful in treating cognitive impairment selected using these genes should decrease the abundance or attenuate the function of the expressed gene products of these genes.

Example 22

An ANOVA was conducted on the probe set signal values for all present probe sets by combining two groups of animals and comparing them to the third group. An "AU ANOVA" was performed, where Aged Impaired were combined with Young and compared to Aged Unimpaired. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 22 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 22

DG - AU ANOVA NEGATIVE CORRELATION
GENBANK ® ID

NM_001004075
NM_001004200
NM_001005529
NM_001007146
NM_001008511
NM_001008885
NM_001011959
NM_001012034
NM_001012140
NM_001013065
NM_001013165
NM_001013198
NM_001017382
NM_012630
NM_012775
NM_012806
NM_012953
NM_012955
NM_012991
NM_013031
NM_013094
NM_013159
NM_013189
NM_017158
NM_017319
NM_019123
NM_019149
NM_019168
NM_019349
NM_021688
NM_021774
NM_022946
NM_024394
NM_030872
NM_031036
NM_031131
NM_031354
NM_031569
NM_053499
NM_053733
NM_053961

TABLE 22-continued

DG - AU ANOVA NEGATIVE CORRELATION GENBANK ® ID

NM_054006
NM_133411
NM_134326
NM_134373
NM_172039
NM_172317
NM_175604
NM_175764
NM_182737
NM_198750
NM_199111
NM_199400
NM_199463
NM_212496
XM_213749
XM_214344
XM_215286
XM_215813
XM_216025
XM_216548
XM_216784
XM_217359
XM_218459
XM_218523
XM_219349
XM_222242
XM_223938
XM_224256
XM_224947
XM_225168
XM_225717
XM_227090
XM_230303
XM_230616
XM_232735
XM_233141
XM_235185
XM_235662
XM_239329
XM_242005
XM_340742
XM_341312
XM_341842
XM_342392
XM_342828
XM_343175
XM_343278
XM_343535
XM_343559
XM_347168
XM_573428
XM_576252
XM_579545

The genes in this set show abundance of expressed gene product(s) in the Aged Unimpaired population that are significantly increased, as determined by ANOVA, compared to those abundances in Young and Aged Impaired populations combined. In addition, the abundance of expressed gene product(s) in the aged animals negatively correlate with learning index of the animals, such that poorer learners have lower abundances of expressed gene products of the selected genes. Therefore, compounds useful in treating cognitive impairment selected using these genes should increase the abundance or enhance the function of the expressed gene products of these genes.

Example 23

An ANOVA was conducted on the probe set signal values for all present probe sets by combining two groups of animals and comparing them to the third group. An "AU ANOVA" was performed, where Aged Impaired were combined with Young and compared to Aged Unimpaired. Any probe sets having a p-value less than 0.05 were considered significantly changed and the genes or plurality of genes selected.

Microarray Results

Table 23 shows the genes that were identified as being associated with cognitive impairment in this experiment. The reference sequence transcript ID (GENBANK®) number for the exemplar sequence) was used to identify genes considered significantly changed. When this exemplar ID was not available, a UniGene identifier was used in conjunction with the GENBANK® accession number.

TABLE 23

DG - AU ANOVA INCREASE GENBANK ® ID

AF452647
NM_001004230
NM_001004279
NM_001004449
NM_001005565
NM_001007011
NM_001007613
NM_001007637
NM_001007739
NM_001008309
NM_001008316
NM_001008339
NM_001008515
NM_001008521
NM_001009619
NM_001009653
NM_001010965
NM_001011942
NM_001011979
NM_001012159
NM_001012174
NM_001013036
NM_001013163
NM_012576
NM_012583
NM_012774
NM_012858
NM_012935
NM_013220
NM_016994
NM_017138
NM_017263
NM_017294
NM_019170
NM_019251
NM_019302
NM_019374
NM_019623
NM_021262
NM_021264
NM_022236
NM_022269
NM_022398
NM_022515
NM_022694
NM_022709
NM_022961
NM_024125
NM_024139
NM_030844
NM_030858
NM_031028
NM_031138
NM_031518
NM_031597
NM_031822
NM_053402
NM_053421
NM_053502
NM_053613
NM_053621
NM_053826

TABLE 23-continued

DG - AU ANOVA INCREASE

GENBANK ® ID

NM_053876
NM_053901
NM_057152
NM_057196
NM_057204
NM_130740
NM_133405
NM_134356
NM_134411
NM_134432
NM_134457
NM_138889
NM_139253
NM_153316
NM_173837
NM_175598
NM_178101
NM_198751
NM_212525
NM_213567
XM_213240
XM_213336
XM_213992
XM_214720
XM_214895
XM_215184
XM_215372
XM_215424
XM_215566
XM_215602
XM_215949
XM_216112
XM_216191
XM_216515
XM_217326
XM_217825
XM_217837
XM_219045
XM_220506
XM_220606
XM_221030
XM_221635
XM_222251
XM_222832
XM_225866
XM_226237
XM_226722
XM_230846
XM_230856
XM_231552
XM_232855
XM_233377
XM_233535
XM_233679
XM_234017
XM_234441
XM_237291
XM_238063
XM_240417
XM_340918
XM_341239
XM_341857
XM_341950
XM_342141
XM_342312
XM_342398
XM_342579
XM_342662
XM_343446
XM_574233
XM_577170

The genes in this set show abundance of expressed gene product(s) in the Aged Unimpaired population that are significantly increased, as determined by ANOVA, compared to those abundances in Young and Aged Impaired populations combined. Therefore, compounds useful in treating cognitive impairment selected using these genes should increase the abundance or enhance the function of the expressed gene products of these genes.

Example 24

An ANOVA was conducted on the probe set signal values for all present probe sets by combining two groups of animals and comparing them to the third group. An "AU ANOVA" was performed, where Aged Impaired were combined with Young and compared to Aged Unimpaired. Any probe sets having a p-value less than 0.05 were considered significantly changed and the genes or plurality of genes selected.

Microarray Results

Table 24 shows the genes that were identified as being associated with cognitive impairment in this experiment. The reference sequence transcript ID (GENBANK®) number for the exemplar sequence) was used to identify genes considered significantly changed. When this exemplar ID was not available, a UniGene identifier was used in conjunction with the GENBANK® accession number.

TABLE 24

DG - AU ANOVA DECREASE

GENBANK ® ID

BF564995
BM389079
AI171599
NM_001000510
NM_001001515
NM_001001799
NM_001004132
NM_001005381
NM_001005876
NM_001005879
NM_001006968
NM_001006994
NM_001007667
NM_001008331
NM_001009652
NM_001011891
NM_001012053
NM_001012083
NM_001012175
NM_001013090
NM_001013153
NM_012568
NM_012740
NM_012798
NM_012809
NM_012829
NM_017063
NM_017066
NM_017197
NM_017201
NM_017305
NM_017321
NM_019185
NM_021671
NM_021751
NM_021770
NM_022217
NM_022282
NM_022589
NM_022690
NM_022863
NM_022928
NM_023991
NM_024000
NM_024146
NM_024159
NM_030861

TABLE 24-continued

DG - AU ANOVA DECREASE

NM_030994
NM_031022
NM_031043
NM_031235
NM_031351
NM_031356
NM_031520
NM_031594
NM_031646
NM_032062
NM_032072
NM_032616
NM_053448
NM_053542
NM_053868
NM_057201
NM_080886
NM_080887
NM_080895
NM_131906
NM_131914
NM_134468
NM_138840
NM_138858
NM_138891
NM_139254
NM_145089
NM_145785
NM_152790
NM_171994
NM_172157
NM_173120
NM_177481
NM_177927
NM_178095
NM_178847
NM_181388
NM_182674
NM_198764
NM_199097
XM_213270
XM_213591
XM_213779
XM_213954
XM_214238
XM_214709
XM_214751
XM_215286
XM_215403
XM_215574
XM_216102
XM_216400
XM_217078
XM_217732
XM_218502
XM_220805
XM_222111
XM_222152
XM_225983
XM_226789
XM_227025
XM_230967
XM_232640
XM_234483
XM_235156
XM_235179
XM_235940
XM_238151
XM_238213
XM_340775
XM_340802
XM_341058
XM_341104
XM_341497
XM_341558
XM_341584
XM_342477
XM_342588
XM_342682
XM_342863
XM_343273
XM_343415
XM_347236
XM_573983
XM_579546
NM_022250
UniGene ID Rn.17829
Rn.21816
Rn.22355

The genes in this set show abundance of expressed gene product(s) in the Aged Unimpaired population that are significantly decreased, as determined by ANOVA, compared to those abundances in Young and Aged Impaired populations combined. Therefore, compounds useful in treating cognitive impairment selected using these genes should decrease the abundance or attenuate the function of the expressed gene products of these genes.

Example 25

An ANOVA was conducted on the probe set signal values for all probe sets by combining two groups of animals and comparing them to the third group. An "AI ANOVA" was performed, where Aged Unimpaired were combined with Young and compared to Aged Impaired. All probe sets were considered in the statistical analysis based on the gcRMA method of data extraction from the perfect match sequences for each probe. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 25 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 25

CA1 - AI ANOVA POSITIVE CORRELATION GENBANK ® ID

AA800031
AI101331
AI639001
BG377379
BG662522
NM_001004209
NM_001005762
NM_001005898
NM_001007651
NM_001008322
NM_001008324
NM_001009600
NM_001011946
NM_001012079

TABLE 25-continued

CA1 - AI ANOVA POSITIVE CORRELATION GENBANK® ID

NM_001012111
NM_001012126
NM_001012177
NM_001012223
NM_001013082
NM_001017386
NM_001017450
NM_001024371
NM_001024925
NM_001025419
NM_001029901
NM_001033852
NM_001034933
NM_012543
NM_012562
NM_012577
NM_012671
NM_012686
NM_012777
NM_012884
NM_013015
NM_013060
NM_013091
NM_013107
NM_013173
NM_013191
NM_013198
NM_013219
NM_017068
NM_017223
NM_017267
NM_017356
NM_019318
NM_019362
NM_021775
NM_022198
NM_022226
NM_022502
NM_022617
NM_023978
NM_024163
NM_030863
NM_030992
NM_031014
NM_031034
NM_031147
NM_031521
NM_031552
NM_031812
NM_032066
NM_033443
NM_053021
NM_053407
NM_053445
NM_053467
NM_053485
NM_053538
NM_053777
NM_053783
NM_053910
NM_054001
NM_057204
NM_080907
NM_133534
NM_134390
NM_138502
NM_138914
NM_145674
NM_152790
NM_173101
NM_175578
NM_175582
NM_181639
NM_207602
NM_207617
NM_212528
XM_213329
XM_214968
XM_215037
XM_215095
XM_216837
XM_219262
XM_222242
XM_224337
XM_225631
XM_227870
XM_228072
XM_232608
XM_238362
XM_341081
XM_341851
XM_341936
XM_341940
XM_342291
XM_342297
XM_342317
XM_342521
XM_343274
XM_343468
XM_343773
XM_343776
XM_344421
XM_573100

The genes in this set show abundance of expressed gene product(s) in the Aged Impaired population that are significantly increased, as determined by ANOVA, compared to those abundances in Young and Aged Unimpaired populations combined. In addition, the abundance of expressed gene product(s) in the aged animals positively correlate with learning index of the animals, such that poorer learners have higher abundances of expressed gene products of the selected genes. Therefore, compounds useful in treating cognitive impairment selected using these genes should decrease the abundance or attenuate the function of the expressed gene products of these genes.

Example 26

An ANOVA was conducted on the probe set signal values for all probe sets by combining two groups of animals and comparing them to the third group. An "AI ANOVA" was performed, where Aged Unimpaired were combined with Young and compared to Aged Impaired. All probe sets were considered in the statistical analysis based on the gcRMA method of data extraction from the perfect match sequences for each probe. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 26 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 26

CA1 - AI ANOVA NEGATIVE CORRELATION
GENBANK ® ID

AI227598
AW529408
BF397258
NM_001005381
NM_001008354
NM_001008557
NM_001010946
NM_001012012
NM_001012021
NM_001012187
NM_001012195
NM_001013198
NM_001017376
NM_001025271
NM_001025711
NM_001025738
NM_001033701
NM_012736
NM_013083
NM_013113
NM_017030
NM_017059
NM_019128
NM_019142
NM_019194
NM_021840
NM_022229
NM_022289
NM_022300
NM_022615
NM_031069
NM_031315
NM_031707
NM_031821
NM_053316
NM_053410
NM_053434
NM_053633
NM_053698
NM_053713
NM_053849
NM_053883
NM_080402
NM_133580
NM_138838
NM_138911
NM_139060
NM_139091
NM_172034
NM_199394
NM_199463
NM_213627
XM_213658
XM_214245
XM_214369
XM_214697
XM_215826
XM_216102
XM_216679
XM_216762
XM_216884
XM_217115
XM_217210
XM_218506
XM_219500
XM_219525
XM_221333
XM_221635
XM_223693
XM_224389
XM_224929
XM_225039
XM_232936
XM_234385
XM_235179
XM_235552
XM_235878

TABLE 26-continued

CA1 - AI ANOVA NEGATIVE CORRELATION
GENBANK ® ID

XM_236953
XM_242556
XM_243390
XM_340809
XM_341663
XM_342107
XM_342179
XM_342763
XM_342930
XM_343046
XM_343326
XM_343574
XM_343761
XM_344130
XM_345861
XM_345981
XM_573165
XM_575396
XM_577023

The genes in this set show abundance of expressed gene product(s) in the Aged Impaired population that are significantly decreased, as determined by ANOVA, compared to those abundances in Young and Aged Unimpaired populations combined. In addition, the abundance of expressed gene product(s) in the aged animals negatively correlate with learning index of the animals, such that poorer learners have lower abundances of expressed gene products of the selected genes. Therefore, compounds useful in treating cognitive impairment selected using these genes should increase the abundance or enhance the function of the expressed gene products of these genes.

Example 27

An ANOVA was conducted on the probe set signal values for all probe sets by combining two groups of animals and comparing them to the third group. An "AI ANOVA" was performed, where Aged Unimpaired were combined with Young and compared to Aged Impaired. All probe sets were considered in the statistical analysis based on the gcRMA method of data extraction from the perfect match sequences for each probe. Any probe sets having a p-value less than 0.05 were considered significantly changed and the genes or plurality of genes selected.

Microarray Results

Table 27 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 27

CA1 - AI ANOVA INCREASE
GENBANK ® ID

AI012566
AI170346
AI179982
AI410079
AI717047
BF396482
BF417285
BG672075

TABLE 27-continued

CA1 - AI ANOVA INCREASE
GENBANK ® ID

BG673602
BM392140
L26525
NM_001001511
NM_001001513
NM_001001800
NM_001004072
NM_001004081
NM_001004226
NM_001004250
NM_001004273
NM_001005534
NM_001005539
NM_001005565
NM_001006989
NM_001007000
NM_001007617
NM_001007624
NM_001007625
NM_001007629
NM_001007654
NM_001007665
NM_001007677
NM_001007682
NM_001008344
NM_001008365
NM_001008374
NM_001008829
NM_001008835
NM_001009474
NM_001009623
NM_001011893
NM_001011903
NM_001011917
NM_001011920
NM_001011925
NM_001011959
NM_001011981
NM_001011989
NM_001011991
NM_001011993
NM_001012051
NM_001012057
NM_001012065
NM_001012222
NM_001012744
NM_001013081
NM_001013086
NM_001013087
NM_001013121
NM_001013137
NM_001013174
NM_001013179
NM_001013190
NM_001013240
NM_001017383
NM_001024247
NM_001024261
NM_001025056
NM_001025282
NM_001025289
NM_001025423
NM_001025648
NM_001025721
NM_001025722
NM_001031641
NM_001031644
NM_001033968
NM_001034004
NM_001034090
NM_001034164
NM_012488
NM_012497
NM_012512
NM_012512
NM_012531
NM_012595

TABLE 27-continued

CA1 - AI ANOVA INCREASE
GENBANK ® ID

NM_012645
NM_012671
NM_012703
NM_012747
NM_012749
NM_012771
NM_012815
NM_012819
NM_012823
NM_012837
NM_012838
NM_012925
NM_012939
NM_013001
NM_013044
NM_013055
NM_013069
NM_013137
NM_013157
NM_016986
NM_017008
NM_017009
NM_017014
NM_017113
NM_017125
NM_017132
NM_017154
NM_017160
NM_017169
NM_017177
NM_017181
NM_017193
NM_017196
NM_017257
NM_017264
NM_017274
NM_017288
NM_017320
NM_017333
NM_017348
NM_017351
NM_017356
NM_017359
NM_019238
NM_019289
NM_019290
NM_019346
NM_019358
NM_019359
NM_020082
NM_021576
NM_021690
NM_021989
NM_022266
NM_022285
NM_022381
NM_022390
NM_022392
NM_022500
NM_022510
NM_022512
NM_022525
NM_022526
NM_022597
NM_022602
NM_022668
NM_022697
NM_022703
NM_022856
NM_024155
NM_024160
NM_024366
NM_024396
NM_030826
NM_030859
NM_030872
NM_030987

TABLE 27-continued

CA1 - AI ANOVA INCREASE
GENBANK® ID

| |
|---|
| NM_031057 |
| NM_031090 |
| NM_031140 |
| NM_031357 |
| NM_031509 |
| NM_031614 |
| NM_031624 |
| NM_031648 |
| NM_031660 |
| NM_031668 |
| NM_031672 |
| NM_031685 |
| NM_031698 |
| NM_031756 |
| NM_031789 |
| NM_031818 |
| NM_031827 |
| NM_031841 |
| NM_031973 |
| NM_040669 |
| NM_053323 |
| NM_053442 |
| NM_053455 |
| NM_053516 |
| NM_053536 |
| NM_053553 |
| NM_053554 |
| NM_053560 |
| NM_053597 |
| NM_053612 |
| NM_053684 |
| NM_053773 |
| NM_053794 |
| NM_053838 |
| NM_053959 |
| NM_053979 |
| NM_053985 |
| NM_054006 |
| NM_057114 |
| NM_057137 |
| NM_057197 |
| NM_080887 |
| NM_080890 |
| NM_130403 |
| NM_130416 |
| NM_130419 |
| NM_130428 |
| NM_130739 |
| NM_133297 |
| NM_133298 |
| NM_133392 |
| NM_133405 |
| NM_133418 |
| NM_133605 |
| NM_133618 |
| NM_133621 |
| NM_134334 |
| NM_134349 |
| NM_134389 |
| NM_134410 |
| NM_134432 |
| NM_138508 |
| NM_138521 |
| NM_138826 |
| NM_138828 |
| NM_138900 |
| NM_138905 |
| NM_138917 |
| NM_139103 |
| NM_139110 |
| NM_139189 |
| NM_139216 |
| NM_139327 |
| NM_145081 |
| NM_145775 |
| NM_147210 |
| NM_153621 |

TABLE 27-continued

CA1 - AI ANOVA INCREASE
GENBANK® ID

| |
|---|
| NM_153628 |
| NM_172033 |
| NM_172038 |
| NM_172222 |
| NM_172335 |
| NM_173095 |
| NM_173118 |
| NM_173123 |
| NM_173147 |
| NM_175756 |
| NM_175838 |
| NM_176077 |
| NM_178095 |
| NM_181363 |
| NM_181381 |
| NM_181628 |
| NM_183330 |
| NM_184046 |
| NM_198738 |
| NM_199087 |
| NM_199092 |
| NM_199118 |
| NM_199399 |
| NM_199404 |
| NM_207591 |
| NM_207599 |
| NM_207609 |
| NM_212495 |
| NM_212525 |
| NM_212538 |
| XM_213335 |
| XM_213408 |
| XM_213540 |
| XM_213650 |
| XM_213777 |
| XM_213824 |
| XM_213879 |
| XM_214250 |
| XM_214316 |
| XM_214478 |
| XM_214480 |
| XM_214518 |
| XM_214583 |
| XM_214769 |
| XM_214838 |
| XM_215524 |
| XM_215607 |
| XM_215733 |
| XM_215897 |
| XM_216565 |
| XM_216688 |
| XM_216704 |
| XM_216740 |
| XM_216962 |
| XM_217239 |
| XM_217335 |
| XM_217372 |
| XM_218617 |
| XM_218816 |
| XM_218977 |
| XM_219948 |
| XM_220095 |
| XM_220357 |
| XM_220541 |
| XM_221100 |
| XM_223012 |
| XM_223785 |
| XM_224535 |
| XM_224538 |
| XM_225014 |
| XM_225147 |
| XM_225160 |
| XM_225628 |
| XM_225644 |
| XM_225711 |
| XM_226165 |
| XM_228701 |

TABLE 27-continued

CA1 - AI ANOVA INCREASE
GENBANK® ID

XM_230036
XM_230291
XM_231287
XM_231620
XM_231749
XM_235497
XM_235558
XM_235710
XM_237381
XM_237790
XM_238019
XM_238380
XM_238770
XM_243637
XM_341389
XM_341509
XM_341796
XM_341882
XM_341957
XM_342002
XM_342300
XM_342528
XM_342600
XM_342686
XM_343034
XM_343259
XM_343268
XM_343306
XM_343396
XM_343427
XM_344524
XM_345535
XM_345584
XM_345825
XM_345849
XM_345870
XM_347163
XM_575585
XM_576343
XM_576401
XM_576459

The genes in this set show abundance of expressed gene product(s) in the Aged Impaired population that are significantly increased, as determined by ANOVA, compared to those abundances in Young and Aged Unimpaired populations combined. Therefore, compounds useful in treating cognitive impairment selected using these genes should decrease the abundance or attenuate the function of the expressed gene products of these genes.

Example 28

An ANOVA was conducted on the probe set signal values for all probe sets by combining two groups of animals and comparing them to the third group. An "AI ANOVA" was performed, where Aged Unimpaired were combined with Young and compared to Aged Impaired. All probe sets were considered in the statistical analysis based on the gcRMA method of data extraction from the perfect match sequences for each probe. Any probe sets having a p-value less than 0.05 were considered significantly changed and the genes or plurality of genes selected.

Microarray Results

Table 28 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 28

CA1 - AI ANOVA DECREASE
GENBANK® ID

AF073379
AI029288
AI229643
AI599699
AW528891
BE118251
BF404393
BF410962
NM_001002289
NM_001002851
NM_001003957
NM_001004198
NM_001004210
NM_001004277
NM_001004279
NM_001004442
NM_001005536
NM_001005872
NM_001007728
NM_001008320
NM_001008353
NM_001009268
NM_001009605
NM_001011901
NM_001011966
NM_001012043
NM_001012143
NM_001012144
NM_001012211
NM_001012475
NM_001013066
NM_001013096
NM_001013099
NM_001013128
NM_001013133
NM_001013178
NM_001013244
NM_001014792
NM_001015011
NM_001024318
NM_001024766
NM_001024790
NM_001024794
NM_001025136
NM_001025402
NM_001025414
NM_001025650
NM_001025667
NM_001025705
NM_001033655
NM_001033699
NM_001033974
NM_001033984
NM_001034014
NM_001034068
NM_001034131
NM_012568
NM_012573
NM_012576
NM_012596
NM_012651
NM_012653
NM_012688
NM_012701
NM_012727
NM_012780
NM_012835
NM_012934
NM_012991
NM_013036
NM_013100
NM_013102
NM_013111
NM_013126
NM_013161
NM_013179
NM_013189

TABLE 28-continued

CA1 - AI ANOVA DECREASE GENBANK® ID

| |
|---|
| NM_013199 |
| NM_017041 |
| NM_017073 |
| NM_017238 |
| NM_017303 |
| NM_017352 |
| NM_019163 |
| NM_019218 |
| NM_019282 |
| NM_019288 |
| NM_019347 |
| NM_019348 |
| NM_020306 |
| NM_021266 |
| NM_021653 |
| NM_021763 |
| NM_021843 |
| NM_022249 |
| NM_022254 |
| NM_022688 |
| NM_022847 |
| NM_022850 |
| NM_022867 |
| NM_022962 |
| NM_023971 |
| NM_023989 |
| NM_024362 |
| NM_024401 |
| NM_031056 |
| NM_031123 |
| NM_031130 |
| NM_031318 |
| NM_031720 |
| NM_031730 |
| NM_031753 |
| NM_031777 |
| NM_031828 |
| NM_033485 |
| NM_053349 |
| NM_053441 |
| NM_053487 |
| NM_053503 |
| NM_053530 |
| NM_053616 |
| NM_053693 |
| NM_053703 |
| NM_053718 |
| NM_053740 |
| NM_053775 |
| NM_053781 |
| NM_053786 |
| NM_053876 |
| NM_053888 |
| NM_053895 |
| NM_054008 |
| NM_057212 |
| NM_130748 |
| NM_133318 |
| NM_133411 |
| NM_133548 |
| NM_133591 |
| NM_133596 |
| NM_134383 |
| NM_134388 |
| NM_138837 |
| NM_138907 |
| NM_138922 |
| NM_144758 |
| NM_147135 |
| NM_147142 |
| NM_153317 |
| NM_173145 |
| NM_177419 |
| NM_181370 |
| NM_181380 |
| NM_182668 |
| NM_182844 |
| NM_198749 |
| NM_198760 |
| NM_198761 |
| NM_198770 |
| NM_199373 |
| U48828 |
| XM_213440 |
| XM_213842 |
| XM_213954 |
| XM_214093 |
| XM_214312 |
| XM_214621 |
| XM_214673 |
| XM_214696 |
| XM_214823 |
| XM_214883 |
| XM_215376 |
| XM_215451 |
| XM_215883 |
| XM_215892 |
| XM_215984 |
| XM_216047 |
| XM_216161 |
| XM_216225 |
| XM_216318 |
| XM_217560 |
| XM_217570 |
| XM_217601 |
| XM_218138 |
| XM_218187 |
| XM_218200 |
| XM_218347 |
| XM_218845 |
| XM_219372 |
| XM_219905 |
| XM_221050 |
| XM_221212 |
| XM_221231 |
| XM_221380 |
| XM_221426 |
| XM_221641 |
| XM_221724 |
| XM_221888 |
| XM_221962 |
| XM_222103 |
| XM_222184 |
| XM_222476 |
| XM_222770 |
| XM_223643 |
| XM_223729 |
| XM_225138 |
| XM_225138 |
| XM_225168 |
| XM_225169 |
| XM_225220 |
| XM_226349 |
| XM_226436 |
| XM_226843 |
| XM_226874 |
| XM_227104 |
| XM_227444 |
| XM_227811 |
| XM_230449 |
| XM_230877 |
| XM_231798 |
| XM_231803 |
| XM_232197 |
| XM_232220 |
| XM_232599 |
| XM_233141 |
| XM_233499 |
| XM_233792 |
| XM_234219 |
| XM_234263 |
| XM_234299 |
| XM_234345 |
| XM_234345 |

TABLE 28-continued

CA1 - AI ANOVA DECREASE
GENBANK® ID

XM_234470
XM_234481
XM_234514
XM_234540
XM_234546
XM_235768
XM_239074
XM_239260
XM_341111
XM_341391
XM_341590
XM_341642
XM_341653
XM_341709
XM_342151
XM_342217
XM_342481
XM_342552
XM_342692
XM_342734
XM_342775
XM_342804
XM_342808
XM_343045
XM_343148
XM_343548
XM_344594
XM_345418
XM_345789
XM_574979
XM_575397

The genes in this set show abundance of expressed gene product(s) in the Aged Impaired population that are significantly decreased, as determined by ANOVA, compared to those abundances in Young and Aged Unimpaired populations combined. Therefore, compounds useful in treating cognitive impairment selected using these genes should increase the abundance or enhance the function of the expressed gene products of these genes.

Example 29

An ANOVA was conducted on the probe set signal values for all probe sets by combining two groups of animals and comparing them to the third group. An "AU ANOVA" was performed, where Aged Impaired were combined with Young and compared to Aged Unimpaired. All probe sets were considered in the statistical analysis based on the gcRMA method of data extraction from the perfect match sequences for each probe. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 29 shows the genes that were identified as being associated with cognitive impairment in this experiment. The reference sequence transcript ID (GENBANK®) number for the exemplar sequence) was used to identify genes considered significantly changed. When this exemplar ID was not available, a UniGene identifier was used in conjunction with the GENBANK® accession number.

TABLE 29

AU ANOVA POSITIVE CORRELATION
GENBANK® ID

AA955871
BF288303
BF410275
NM_001002016
NM_001025403
NM_001025744
NM_001035233
NM_012623
NM_012660
NM_012869
NM_013159
NM_013176
NM_013197
NM_017007
NM_017103
NM_017294
NM_017306
NM_017347
NM_017354
NM_019183
NM_019239
NM_019309
NM_019351
NM_019354
NM_031097
NM_033359
NM_053383
NM_053644
NM_053669
NM_053721
NM_053811
NM_053824
NM_053930
NM_053972
NM_057208
NM_080577
NM_080786
NM_130406
NM_131906
NM_138848
NM_153469
NM_172041
NM_172224
NM_173325
XM_213564
XM_214400
XM_216018
XM_216784
XM_218336
XM_220775
XM_223057
XM_223227
XM_224618
XM_230288
XM_230616
XM_230765
XM_234508
XM_239329
XM_341972
XM_342003
XM_342723
XM_343303
XM_343764
XM_573915
XM_575671

The genes in this set show abundance of expressed gene product(s) in the Aged Unimpaired population that are significantly decreased, as determined by ANOVA, compared to those abundances in Young and Aged Impaired populations combined. In addition, the abundance of expressed gene product(s) in the aged animals positively correlate with learning index of the animals, such that poorer learners have higher abundances of expressed gene products of the selected genes. Therefore, compounds useful in treating cognitive impairment selected using these genes should decrease the abundance or attenuate the function of the expressed gene products of these genes.

Example 30

An ANOVA was conducted on the probe set signal values for all probe sets by combining two groups of animals and comparing them to the third group. An "AU ANOVA" was performed, where Aged Impaired were combined with Young and compared to Aged Unimpaired. All probe sets were considered in the statistical analysis based on the gcRMA method of data extraction from the perfect match sequences for each probe. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 30 shows the genes that were identified as being associated with cognitive impairment in this experiment. The reference sequence transcript ID (GENBANK®) number for the exemplar sequence) was used to identify genes considered significantly changed. When this exemplar ID was not available, a UniGene identifier was used in conjunction with the GENBANK® accession number.

TABLE 30

CA1 - AU ANOVA NEGATIVE CORRELATION
GENBANK ® ID

BG378690
NM_001002830
NM_001004075
NM_001008382
NM_001008524
NM_001011936
NM_001013204
NM_001013212
NM_001033674
NM_001034129
NM_017089
NM_017271
NM_019161
NM_019364
NM_021262
NM_022921
NM_024002
NM_024131
NM_031041
NM_031082
NM_031122
NM_031133
NM_031139
NM_031642
NM_031645
NM_032058
NM_053389
NM_053499
NM_053500
NM_053578
NM_057207
NM_134395
NM_134408
NM_134417
NM_138536
NM_138856
NM_145677
NM_152861
NM_172243

TABLE 30-continued

CA1 - AU ANOVA NEGATIVE CORRELATION
GENBANK ® ID

XM_213725
XM_215082
XM_215616
XM_216295
XM_216400
XM_216712
XM_216841
XM_223674
XM_225726
XM_228197
XM_233467
XM_236745
XM_237179
XM_239510
XM_340856
XM_342131
XM_342268
XM_343318
XM_343413
XM_343513

The genes in this set show abundance of expressed gene product(s) in the Aged Unimpaired population that are significantly increased, as determined by ANOVA, compared to those abundances in Young and Aged Impaired populations combined. In addition, the abundance of expressed gene product(s) in the aged animals negatively correlate with learning index of the animals, such that poorer learners have lower abundances of expressed gene products of the selected genes. Therefore, compounds useful in treating cognitive impairment selected using these genes should increase the abundance or enhance the function of the expressed gene products of these genes.

Example 31

An ANOVA was conducted on the probe set signal values for all probe sets by combining two groups of animals and comparing them to the third group. An "AU ANOVA" was performed, where Aged Impaired were combined with Young and compared to Aged Unimpaired. All probe sets were considered in the statistical analysis based on the gcRMA method of data extraction from the perfect match sequences for each probe. Any probe sets having a p-value less than 0.05 were considered significantly changed and the genes or plurality of genes selected.

Microarray Results

Table 31 shows the genes that were identified as being associated with cognitive impairment in this experiment. The reference sequence transcript ID (GENBANK®) number for the exemplar sequence) was used to identify genes considered significantly changed. When this exemplar ID was not available, a UniGene identifier was used in conjunction with the GENBANK® accession number.

TABLE 31

CA1 - AU ANOVA INCREASE
GENBANK ® ID

AA859127
AA998007
AI137495
BF287008
BI294974
BM384139
BM388245

TABLE 31-continued

CA1 - AU ANOVA INCREASE
GENBANK ® ID

BM390128
NM_001004090
NM_001004238
NM_001004255
NM_001004443
NM_001005528
NM_001006969
NM_001007557
NM_001007609
NM_001007654
NM_001008339
NM_001008364
NM_001008515
NM_001009604
NM_001009973
NM_001009974
NM_001010961
NM_001011922
NM_001011950
NM_001011953
NM_001012003
NM_001012030
NM_001012039
NM_001012096
NM_001012105
NM_001012131
NM_001012181
NM_001012459
NM_001013151
NM_001013152
NM_001013154
NM_001013165
NM_001013165
NM_001013184
NM_001024964
NM_001025035
NM_001025137
NM_001025709
NM_001025725
NM_001030024
NM_001033866
NM_001034110
NM_012592
NM_012720
NM_012805
NM_012806
NM_012848
NM_012895
NM_012913
NM_012924
NM_012935
NM_012992
NM_013057
NM_013088
NM_013150
NM_013151
NM_016994
NM_017212
NM_017290
NM_017318
NM_019251
NM_019361
NM_021584
NM_021846
NM_022205
NM_022252
NM_022499
NM_022529
NM_022545
NM_024125
NM_024153
NM_031058
NM_031112
NM_031148
NM_031517
NM_031623
NM_031740

TABLE 31-continued

CA1 - AU ANOVA INCREASE
GENBANK ® ID

NM_031763
NM_053482
NM_053662
NM_053707
NM_053926
NM_057107
NM_057108
NM_057143
NM_057196
NM_080906
NM_080910
NM_130740
NM_131911
NM_131914
NM_133303
NM_134326
NM_138530
NM_138835
NM_138873
NM_145084
NM_145670
NM_145673
NM_145788
NM_147205
NM_153475
NM_172325
NM_175764
NM_182821
NM_182955
NM_201415
NM_212496
NM_213628
XM_213370
XM_213560
XM_213898
XM_213906
XM_214153
XM_214163
XM_214927
XM_215423
XM_215564
XM_215947
XM_215949
XM_216202
XM_216403
XM_216407
XM_216643
XM_216757
XM_216893
XM_217086
XM_218162
XM_218502
XM_218648
XM_219879
XM_219925
XM_220398
XM_221120
XM_221307
XM_223327
XM_223580
XM_223597
XM_224863
XM_225439
XM_226076
XM_226329
XM_230845
XM_233535
XM_233883
XM_234238
XM_234377
XM_234394
XM_235296
XM_236948
XM_237093
XM_238731
XM_340798
XM_341508

TABLE 31-continued

CA1 - AU ANOVA INCREASE
GENBANK ® ID

XM_341578
XM_342154
XM_342580
XM_342662
XM_342810
XM_342819
XM_343050
XM_344976
XM_574504
XM_575968
XM_578542

The genes in this set show abundance of expressed gene product(s) in the Aged Unimpaired population that are significantly increased, as determined by ANOVA, compared to those abundances in Young and Aged Impaired populations combined. Therefore, compounds useful in treating cognitive impairment selected using these genes should increase the abundance or enhance the function of the expressed gene products of these genes.

Example 32

An ANOVA was conducted on the probe set signal values for all probe sets by combining two groups of animals and comparing them to the third group. An "AU ANOVA" was performed, where Aged Impaired were combined with Young and compared to Aged Unimpaired. All probe sets were considered in the statistical analysis based on the gcRMA method of data extraction from the perfect match sequences for each probe. Any probe sets having a p-value less than 0.05 were considered significantly changed and the genes or plurality of genes selected.
Microarray Results
Table 32 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 32

CA1 - AU ANOVA DECREASE
GENBANK ® ID

AA945615
AI764408
BE103926
BF403383
BF567766
BI287800
NM_001002815
NM_001004132
NM_001007607
NM_001007616
NM_001007629
NM_001007725
NM_001007758
NM_001008369
NM_001008823
NM_001009258
NM_001009405
NM_001011894
NM_001011995
NM_001012101
NM_001012191

TABLE 32-continued

CA1 - AU ANOVA DECREASE
GENBANK ® ID

NM_001012737
NM_001013044
NM_001013108
NM_001013161
NM_001013224
NM_001013432
NM_001013910
NM_001015004
NM_001017381
NM_001024756
NM_001024781
NM_001024795
NM_001024823
NM_001025032
NM_001025032
NM_001025416
NM_001025693
NM_001031656
NM_001031845
NM_001033757
NM_001033882
NM_001033951
NM_001034020
NM_001034133
NM_001034163
NM_001034849
NM_012504
NM_012555
NM_012572
NM_012598
NM_012654
NM_012774
NM_012853
NM_012863
NM_012877
NM_012950
NM_012983
NM_013002
NM_013127
NM_013160
NM_017049
NM_017134
NM_017139
NM_017239
NM_017256
NM_017316
NM_019140
NM_019156
NM_020074
NM_021659
NM_021859
NM_022202
NM_022382
NM_022396
NM_022600
NM_022609
NM_022676
NM_022690
NM_022853
NM_022946
NM_023972
NM_024147
NM_024355
NM_024356
NM_024383
NM_030862
NM_031008
NM_031037
NM_031046
NM_031073
NM_031132
NM_031332
NM_031353
NM_031356
NM_031511
NM_031528
NM_031569

TABLE 32-continued

CA1 - AU ANOVA DECREASE GENBANK® ID

NM_031571
NM_031575
NM_031617
NM_031738
NM_031771
NM_031967
NM_032062
NM_032613
NM_033097
NM_033376
NM_053306
NM_053310
NM_053360
NM_053428
NM_053559
NM_053594
NM_053599
NM_053601
NM_053643
NM_053655
NM_053686
NM_053764
NM_053788
NM_053801
NM_053842
NM_053846
NM_053859
NM_053870
NM_053960
NM_053994
NM_057213
NM_080394
NM_080580
NM_080885
NM_130829
NM_131913
NM_133397
NM_133410
NM_133511
NM_133566
NM_134331
NM_134377
NM_134461
NM_139104
NM_139263
NM_144740
NM_171992
NM_172039
NM_173115
NM_173146
NM_173312
NM_173837
NM_181092
NM_181638
NM_182673
NM_182824
NM_182842
NM_198758
NM_199111
NM_203338
NM_207592
X55812
XM_213318
XM_213993
XM_214630
XM_214669
XM_214720
XM_214775
XM_214916
XM_215469
XM_215742
XM_215887
XM_215939
XM_216189
XM_216745
XM_217021
XM_217124
XM_217188
XM_217279
XM_217388
XM_218412
XM_218851
XM_219529
XM_219801
XM_220224
XM_220602
XM_220884
XM_220982
XM_221672
XM_221977
XM_222223
XM_222896
XM_224261
XM_224952
XM_225259
XM_225625
XM_226213
XM_230296
XM_232488
XM_232640
XM_233231
XM_234205
XM_235426
XM_235500
XM_235640
XM_239504
XM_240330
XM_241981
XM_242982
XM_340775
XM_340911
XM_340967
XM_340999
XM_341790
XM_341998
XM_342032
XM_342134
XM_342389
XM_342409
XM_342632
XM_342905
XM_343058
XM_343247
XM_343394
XM_343459
XM_343483
XM_343582
XM_344434
XM_346464
XM_576183

The genes in this set show abundance of expressed gene product(s) in the Aged Unimpaired population that are significantly decreased, as determined by ANOVA, compared to those abundances in Young and Aged Impaired populations combined. Therefore, compounds useful in treating cognitive impairment selected using these genes should decrease the abundance or attenuate the function of the expressed gene products of these genes.

Example 33

An ANOVA was conducted on the probe set signal values for all probe sets by combining two groups of animals and comparing them to the third group. An "AI ANOVA" was performed, where Aged Unimpaired were combined with Young and compared to Aged Impaired. All probe sets were considered in the statistical analysis based on the gcRMA method of data extraction from the perfect match sequences for each probe. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 33 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 33

CA3 - AI ANOVA POSITIVE CORRELATION
GENBANK ® ID

AA800192
AA892549
AA956317
AI103026
AI556426
BF398122
BI282114
BM391371
NM_001001511
NM_001002016
NM_001004080
NM_001004255
NM_001005765
NM_001007145
NM_001007677
NM_001007797
NM_001008316
NM_001008331
NM_001008374
NM_001008725
NM_001008767
NM_001008880
NM_001009474
NM_001010961
NM_001011893
NM_001011929
NM_001011946
NM_001011954
NM_001011991
NM_001012025
NM_001012040
NM_001012075
NM_001012097
NM_001012111
NM_001012137
NM_001012138
NM_001012150
NM_001012203
NM_001012215
NM_001012235
NM_001013110
NM_001013121
NM_001013130
NM_001013200
NM_001013246
NM_001015009
NM_001017386
NM_001017503
NM_001024238
NM_001024771
NM_001025125
NM_001025289
NM_001031647
NM_001033696
NM_001033701
NM_001033852

TABLE 33-continued

CA3 - AI ANOVA POSITIVE CORRELATION
GENBANK ® ID

NM_001034090
NM_012507
NM_012514
NM_012543
NM_012569
NM_012577
NM_012618
NM_012655
NM_012671
NM_012720
NM_012720
NM_012747
NM_012749
NM_012777
NM_012778
NM_012804
NM_012816
NM_012825
NM_012894
NM_012920
NM_012925
NM_012963
NM_012983
NM_013005
NM_013044
NM_013045
NM_013058
NM_013060
NM_013065
NM_013096
NM_013137
NM_013176
NM_013198
NM_017006
NM_017031
NM_017037
NM_017041
NM_017068
NM_017073
NM_017092
NM_017148
NM_017166
NM_017197
NM_017206
NM_017223
NM_017251
NM_017261
NM_017307
NM_017333
NM_017354
NM_017357
NM_019161
NM_019168
NM_019175
NM_019204
NM_019257
NM_019321
NM_019359
NM_021595
NM_021682
NM_021762
NM_021868
NM_022207
NM_022238
NM_022276
NM_022285
NM_022390
NM_022799
NM_022861
NM_023978
NM_024398
NM_030832
NM_030868
NM_030872
NM_031031
NM_031033
NM_031034

TABLE 33-continued

CA3 - AI ANOVA POSITIVE CORRELATION
GENBANK ® ID

| |
|---|
| NM_031035 |
| NM_031049 |
| NM_031087 |
| NM_031091 |
| NM_031092 |
| NM_031093 |
| NM_031140 |
| NM_031144 |
| NM_031521 |
| NM_031552 |
| NM_031665 |
| NM_031841 |
| NM_032990 |
| NM_052807 |
| NM_053021 |
| NM_053323 |
| NM_053328 |
| NM_053369 |
| NM_053424 |
| NM_053467 |
| NM_053475 |
| NM_053502 |
| NM_053576 |
| NM_053598 |
| NM_053612 |
| NM_053681 |
| NM_053735 |
| NM_053757 |
| NM_053766 |
| NM_053799 |
| NM_053824 |
| NM_053926 |
| NM_053936 |
| NM_053985 |
| NM_053994 |
| NM_054001 |
| NM_057114 |
| NM_057148 |
| NM_057197 |
| NM_057200 |
| NM_057208 |
| NM_080691 |
| NM_130403 |
| NM_133317 |
| NM_133398 |
| NM_133548 |
| NM_133560 |
| NM_133602 |
| NM_133605 |
| NM_138905 |
| NM_138914 |
| NM_139038 |
| NM_139103 |
| NM_139330 |
| NM_145092 |
| NM_145670 |
| NM_147210 |
| NM_152790 |
| NM_152847 |
| NM_153308 |
| NM_153311 |
| NM_172033 |
| NM_172068 |
| NM_173152 |
| NM_175578 |
| NM_175582 |
| NM_175838 |
| NM_176857 |
| NM_178095 |
| NM_181388 |
| NM_199119 |
| XM_213329 |
| XM_213408 |
| XM_213421 |
| XM_213746 |
| XM_213779 |
| XM_213849 |

TABLE 33-continued

CA3 - AI ANOVA POSITIVE CORRELATION
GENBANK ® ID

| |
|---|
| XM_213920 |
| XM_213966 |
| XM_214029 |
| XM_214371 |
| XM_214518 |
| XM_214583 |
| XM_214968 |
| XM_215080 |
| XM_215095 |
| XM_215184 |
| XM_215367 |
| XM_215469 |
| XM_215733 |
| XM_215872 |
| XM_216386 |
| XM_216688 |
| XM_216704 |
| XM_216759 |
| XM_216965 |
| XM_217192 |
| XM_217367 |
| XM_217372 |
| XM_217409 |
| XM_218162 |
| XM_218816 |
| XM_219998 |
| XM_220207 |
| XM_221100 |
| XM_221497 |
| XM_221562 |
| XM_222024 |
| XM_222617 |
| XM_222661 |
| XM_222745 |
| XM_222780 |
| XM_223227 |
| XM_223583 |
| XM_224256 |
| XM_224337 |
| XM_224732 |
| XM_224852 |
| XM_225008 |
| XM_225014 |
| XM_225160 |
| XM_225404 |
| XM_225512 |
| XM_226165 |
| XM_227203 |
| XM_227409 |
| XM_227581 |
| XM_230036 |
| XM_230592 |
| XM_231287 |
| XM_231620 |
| XM_232354 |
| XM_232671 |
| XM_232732 |
| XM_233761 |
| XM_234328 |
| XM_234345 |
| XM_234377 |
| XM_234468 |
| XM_235064 |
| XM_235657 |
| XM_236362 |
| XM_237042 |
| XM_237241 |
| XM_237381 |
| XM_238019 |
| XM_238057 |
| XM_238103 |
| XM_238213 |
| XM_238362 |
| XM_238649 |
| XM_240978 |
| XM_241375 |
| XM_241671 |

TABLE 33-continued

CA3 - AI ANOVA POSITIVE CORRELATION
GENBANK ® ID

XM_340810
XM_340879
XM_340997
XM_341052
XM_341172
XM_341215
XM_341288
XM_341538
XM_341605
XM_341633
XM_341882
XM_341911
XM_342100
XM_342102
XM_342291
XM_342297
XM_342317
XM_342521
XM_342535
XM_342626
XM_342662
XM_342928
XM_343055
XM_343092
XM_343157
XM_343268
XM_343274
XM_343281
XM_343427
XM_343570
XM_343630
XM_343764
XM_343773
XM_343856
XM_343971
XM_344046
XM_344785
XM_345446
XM_345584
XM_345825
XM_347166
XM_347223
XM_573100
XM_575396
XM_576311
XM_576343
XM_576401

The genes in this set show abundance of expressed gene product(s) in the Aged Impaired population that are significantly increased, as determined by ANOVA, compared to those abundances in Young and Aged Unimpaired populations combined. In addition, the abundance of expressed gene product(s) in the aged animals positively correlate with learning index of the animals, such that poorer learners have higher abundances of expressed gene products of the selected genes. Therefore, compounds useful in treating cognitive impairment selected using these genes should decrease the abundance or attenuate the function of the expressed gene products of these genes.

Example 34

An ANOVA was conducted on the probe set signal values for all probe sets by combining two groups of animals and comparing them to the third group. An "AI ANOVA" was performed, where Aged Unimpaired were combined with Young and compared to Aged Impaired. All probe sets were considered in the statistical analysis based on the gcRMA method of data extraction from the perfect match sequences for each probe. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 34 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 34

CA3 - AI ANOVA NEGATIVE CORRELATION
GENBANK ® ID

BF282715
BM391206
NM_001001718
NM_001002818
NM_001003653
NM_001004075
NM_001004217
NM_001004222
NM_001005543
NM_001006602
NM_001006984
NM_001006994
NM_001007656
NM_001007707
NM_001008304
NM_001008511
NM_001008553
NM_001008557
NM_001009422
NM_001009666
NM_001009677
NM_001010946
NM_001011923
NM_001011934
NM_001011957
NM_001011996
NM_001012012
NM_001012098
NM_001012101
NM_001012125
NM_001012192
NM_001013133
NM_001013201
NM_001013906
NM_001014785
NM_001024250
NM_001024756
NM_001029898
NM_001031649
NM_001033069
NM_012500
NM_012600
NM_012739
NM_013083
NM_013090
NM_013111
NM_013113
NM_013130
NM_013174
NM_017126
NM_017135
NM_017352
NM_021688
NM_021699
NM_022186
NM_022188
NM_022264
NM_022272
NM_022511

TABLE 34-continued

CA3 - AI ANOVA NEGATIVE CORRELATION GENBANK ® ID

NM_022599
NM_022688
NM_022860
NM_022938
NM_022941
NM_022948
NM_022961
NM_023104
NM_024366
NM_024381
NM_024390
NM_030830
NM_030841
NM_031006
NM_031030
NM_031062
NM_031070
NM_031344
NM_031520
NM_031569
NM_031583
NM_031742
NM_031749
NM_031851
NM_032079
NM_033349
NM_053334
NM_053388
NM_053528
NM_053575
NM_053613
NM_053621
NM_053622
NM_053792
NM_053810
NM_053849
NM_053883
NM_053950
NM_053990
NM_053997
NM_054008
NM_133394
NM_133425
NM_133562
NM_133596
NM_133596
NM_138833
NM_138866
NM_138893
NM_139254
NM_139337
NM_145098
NM_147141
NM_152861
NM_172062
NM_173094
NM_173115
NM_178091
NM_182844
NM_184051
NM_198726
NM_198756
NM_198783
NM_199098
NM_199500
NM_206881
NM_212496
NM_212544
XM_213426
XM_213626
XM_213672
XM_214331
XM_214400
XM_214475
XM_214485
XM_214491
XM_214550
XM_214895
XM_215069
XM_215082
XM_215134
XM_215826
XM_215883
XM_215931
XM_216112
XM_217385
XM_217908
XM_218851
XM_219796
XM_220219
XM_221270
XM_221304
XM_221627
XM_221833
XM_221910
XM_222717
XM_223327
XM_223693
XM_223921
XM_225039
XM_225072
XM_226843
XM_227414
XM_227428
XM_232735
XM_232745
XM_232901
XM_233544
XM_234219
XM_235295
XM_235878
XM_236614
XM_240178
XM_340884
XM_340889
XM_341015
XM_341249
XM_341314
XM_341326
XM_341520
XM_341663
XM_341955
XM_341969
XM_342107
XM_342295
XM_342692
XM_343140
XM_343413
XM_343429
XM_343614
XM_344009
XM_344168
XM_344426
XM_345668
XM_345848
XM_346887

The genes in this set show abundance of expressed gene product(s) in the Aged Impaired population that are significantly decreased, as determined by ANOVA, compared to those abundances in Young and Aged Unimpaired populations combined. In addition, the abundance of expressed gene product(s) in the aged animals negatively correlate with learning index of the animals, such that poorer learners have lower abundances of expressed gene products of the selected genes. Therefore, compounds useful in treating cognitive impairment selected using these genes should increase the abundance or enhance the function of the expressed gene products of these genes.

Example 35

An ANOVA was conducted on the probe set signal values for all probe sets by combining two groups of animals and comparing them to the third group. An "AI ANOVA" was performed, where Aged Unimpaired were combined with Young and compared to Aged Impaired. All probe sets were considered in the statistical analysis based on the gcRMA method of data extraction from the perfect match sequences for each probe. Any probe sets having a p-value less than 0.05 were considered significantly changed and the genes or plurality of genes selected.

Microarray Results

Table 35 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 35

CA3 - AI ANOVA INCREASE
GENBANK ® ID

AI029288
AI235284
AW535280
BE118404
BF288606
BI273920
BI274299
BM390128
NM_001001800
NM_001004068
NM_001004214
NM_001004239
NM_001005539
NM_001006963
NM_001007641
NM_001007712
NM_001007734
NM_001007739
NM_001007803
NM_001008312
NM_001008509
NM_001008861
NM_001008893
NM_001009239
NM_001009641
NM_001009660
NM_001009668
NM_001009683
NM_001011890
NM_001011910
NM_001011920
NM_001011970
NM_001011974
NM_001011989
NM_001012039
NM_001012057
NM_001012061
NM_001012067
NM_001012123
NM_001012162
NM_001012181
NM_001012201
NM_001012208
NM_001012217
NM_001012275
NM_001013087
NM_001013120
NM_001013179
NM_001013210
NM_001013213
NM_001013250

TABLE 35-continued

CA3 - AI ANOVA INCREASE
GENBANK ® ID

NM_001015026
NM_001024903
NM_001024925
NM_001025418
NM_001025423
NM_001025739
NM_001025744
NM_001031641
NM_001033683
NM_001033964
NM_001034004
NM_001034110
NM_001034157
NM_001034933
NM_001034999
NM_012519
NM_012532
NM_012555
NM_012573
NM_012703
NM_012713
NM_012717
NM_012722
NM_012775
NM_012788
NM_012806
NM_012842
NM_012884
NM_013015
NM_013016
NM_013029
NM_013047
NM_013070
NM_013086
NM_013088
NM_013091
NM_013107
NM_013132
NM_013164
NM_013191
NM_013194
NM_016989
NM_017009
NM_017013
NM_017015
NM_017024
NM_017052
NM_017060
NM_017062
NM_017109
NM_017125
NM_017137
NM_017181
NM_017193
NM_017196
NM_017200
NM_017212
NM_017234
NM_017259
NM_017274
NM_017289
NM_017320
NM_017347
NM_017351
NM_019160
NM_019242
NM_019249
NM_019269
NM_019358
NM_020082
NM_021264
NM_021695
NM_021989
NM_022178
NM_022281
NM_022401
NM_022500

TABLE 35-continued

CA3 - AI ANOVA INCREASE
GENBANK ® ID

| |
|---|
| NM_022502 |
| NM_022516 |
| NM_022592 |
| NM_022617 |
| NM_022677 |
| NM_022699 |
| NM_022800 |
| NM_022853 |
| NM_022856 |
| NM_023025 |
| NM_024001 |
| NM_024155 |
| NM_024372 |
| NM_024396 |
| NM_030871 |
| NM_030989 |
| NM_031005 |
| NM_031018 |
| NM_031027 |
| NM_031099 |
| NM_031107 |
| NM_031132 |
| NM_031321 |
| NM_031357 |
| NM_031509 |
| NM_031576 |
| NM_031620 |
| NM_031648 |
| NM_031672 |
| NM_031677 |
| NM_031694 |
| NM_031797 |
| NM_031806 |
| NM_031818 |
| NM_031827 |
| NM_031970 |
| NM_032067 |
| NM_032462 |
| NM_032619 |
| NM_033097 |
| NM_033230 |
| NM_033443 |
| NM_052981 |
| NM_053434 |
| NM_053442 |
| NM_053493 |
| NM_053506 |
| NM_053516 |
| NM_053550 |
| NM_053553 |
| NM_053560 |
| NM_053599 |
| NM_053633 |
| NM_053639 |
| NM_053796 |
| NM_053840 |
| NM_053893 |
| NM_053895 |
| NM_058211 |
| NM_078622 |
| NM_080584 |
| NM_080688 |
| NM_131911 |
| NM_133298 |
| NM_133303 |
| NM_133307 |
| NM_133511 |
| NM_133534 |
| NM_133545 |
| NM_133598 |
| NM_133611 |
| NM_134334 |
| NM_134349 |
| NM_134390 |
| NM_134408 |
| NM_134453 |
| NM_138520 |
| NM_138828 |
| NM_138832 |
| NM_139043 |
| NM_139105 |
| NM_139110 |
| NM_139216 |
| NM_139255 |
| NM_147136 |
| NM_147206 |
| NM_147207 |
| NM_171992 |
| NM_172030 |
| NM_173116 |
| NM_173118 |
| NM_175595 |
| NM_175843 |
| NM_176075 |
| NM_177419 |
| NM_181475 |
| NM_182821 |
| NM_182843 |
| NM_198743 |
| NM_198787 |
| NM_199093 |
| NM_199118 |
| NM_199388 |
| NM_199499 |
| NM_203366 |
| NM_206950 |
| NM_207609 |
| NM_212523 |
| NM_213563 |
| NM_214457 |
| XM_213688 |
| XM_214035 |
| XM_214480 |
| XM_214958 |
| XM_215076 |
| XM_215177 |
| XM_215466 |
| XM_215576 |
| XM_215607 |
| XM_215757 |
| XM_215935 |
| XM_215949 |
| XM_216004 |
| XM_216407 |
| XM_216565 |
| XM_216717 |
| XM_216872 |
| XM_216910 |
| XM_216968 |
| XM_217062 |
| XM_217188 |
| XM_217254 |
| XM_217263 |
| XM_217441 |
| XM_217570 |
| XM_218293 |
| XM_218336 |
| XM_218382 |
| XM_218617 |
| XM_219296 |
| XM_219539 |
| XM_219785 |
| XM_220175 |
| XM_220333 |
| XM_220805 |
| XM_220918 |
| XM_220986 |
| XM_221307 |
| XM_221387 |
| XM_222911 |
| XM_223781 |
| XM_224474 |
| XM_224535 |
| XM_224561 |

TABLE 35-continued

CA3 - AI ANOVA INCREASE
GENBANK® ID

XM_225020
XM_225147
XM_225628
XM_226510
XM_226874
XM_226987
XM_227066
XM_227870
XM_228044
XM_228073
XM_231566
XM_231620
XM_231650
XM_231763
XM_232809
XM_232865
XM_233603
XM_234281
XM_235480
XM_235552
XM_235558
XM_235609
XM_235710
XM_236009
XM_236020
XM_236196
XM_236560
XM_237371
XM_237415
XM_238205
XM_240311
XM_242032
XM_242644
XM_242982
XM_243637
XM_341111
XM_341133
XM_341877
XM_341940
XM_341957
XM_342002
XM_342052
XM_342218
XM_342286
XM_342397
XM_342800
XM_343259
XM_343303
XM_343396
XM_343412
XM_343479
XM_344524
XM_345535
XM_574504
XM_575585
XM_576238
XM_576459

The genes in this set show abundance of expressed gene product(s) in the Aged Impaired population that are significantly increased, as determined by ANOVA, compared to those abundances in Young and Aged Unimpaired populations combined. Therefore, compounds useful in treating cognitive impairment selected using these genes should decrease the abundance or attenuate the function of the expressed gene products of these genes.

Example 36

An ANOVA was conducted on the probe set signal values for all probe sets by combining two groups of animals and comparing them to the third group. An "AI ANOVA" was performed, where Aged Unimpaired were combined with Young and compared to Aged Impaired. All probe sets were considered in the statistical analysis based on the gcRMA method of data extraction from the perfect match sequences for each probe. Any probe sets having a p-value less than 0.05 were considered significantly changed and the genes or plurality of genes selected.

Microarray Results

Table 36 shows the genes that were identified as being associated with cognitive impairment in this experiment. The reference sequence transcript ID (GENBANK®) number for the exemplar sequence) was used to identify genes considered significantly changed. When this exemplar ID was not available, a UniGene identifier was used in conjunction with the GENBANK® accession number.

TABLE 36

CA3 - AI ANOVA DECREASE
GENBANK® ID

AA943681
AI228348
AW524426
AW524733
BE103926
BF282660
BF407666
BG379941
BG380494
BI287800
NM_001002253
NM_001002828
NM_001003978
NM_001004078
NM_001004132
NM_001004133
NM_001004210
NM_001004227
NM_001004235
NM_001004250
NM_001004277
NM_001004279
NM_001004442
NM_001005884
NM_001005885
NM_001005905
NM_001005908
NM_001006970
NM_001006981
NM_001006997
NM_001007014
NM_001007149
NM_001007643
NM_001007720
NM_001007742
NM_001008299
NM_001008317
NM_001008382
NM_001008766
NM_001008888
NM_001009180
NM_001009258
NM_001009424
NM_001009536
NM_001009619
NM_001009640
NM_001009661
NM_001009719
NM_001009831
NM_001009967
NM_001010963
NM_001010965
NM_001011901
NM_001011906
NM_001011924
NM_001011932
NM_001011950
NM_001011951
NM_001011955

TABLE 36-continued

CA3 - AI ANOVA DECREASE
GENBANK ® ID

| |
|---|
| NM_001011966 |
| NM_001011998 |
| NM_001012017 |
| NM_001012035 |
| NM_001012038 |
| NM_001012060 |
| NM_001012068 |
| NM_001012103 |
| NM_001012119 |
| NM_001012129 |
| NM_001012144 |
| NM_001012152 |
| NM_001012187 |
| NM_001012191 |
| NM_001012195 |
| NM_001012197 |
| NM_001012473 |
| NM_001012738 |
| NM_001013058 |
| NM_001013076 |
| NM_001013170 |
| NM_001013183 |
| NM_001013189 |
| NM_001013198 |
| NM_001013218 |
| NM_001013235 |
| NM_001013426 |
| NM_001013434 |
| NM_001014793 |
| NM_001017377 |
| NM_001024261 |
| NM_001024360 |
| NM_001024754 |
| NM_001025032 |
| NM_001025114 |
| NM_001025271 |
| NM_001025411 |
| NM_001025686 |
| NM_001025696 |
| NM_001025705 |
| NM_001025738 |
| NM_001029900 |
| NM_001029910 |
| NM_001030023 |
| NM_001030029 |
| NM_001030030 |
| NM_001030037 |
| NM_001031645 |
| NM_001031659 |
| NM_001033079 |
| NM_001033674 |
| NM_001033675 |
| NM_001033679 |
| NM_001033684 |
| NM_001033702 |
| NM_001033708 |
| NM_001033715 |
| NM_001033899 |
| NM_001033974 |
| NM_001034014 |
| NM_001034083 |
| NM_001034104 |
| NM_001034112 |
| NM_001034925 |
| NM_001034937 |
| NM_001034994 |
| NM_001035001 |
| NM_001035221 |
| NM_012508 |
| NM_012513 |
| NM_012526 |
| NM_012598 |
| NM_012647 |
| NM_012664 |
| NM_012670 |
| NM_012736 |
| NM_012757 |
| NM_012828 |
| NM_012839 |
| NM_012856 |
| NM_012887 |
| NM_012905 |
| NM_012932 |
| NM_012934 |
| NM_012956 |
| NM_012985 |
| NM_013002 |
| NM_013018 |
| NM_013055 |
| NM_013067 |
| NM_013079 |
| NM_013131 |
| NM_013134 |
| NM_013177 |
| NM_013179 |
| NM_013189 |
| NM_013192 |
| NM_013214 |
| NM_013219 |
| NM_013223 |
| NM_017011 |
| NM_017025 |
| NM_017042 |
| NM_017063 |
| NM_017107 |
| NM_017136 |
| NM_017175 |
| NM_017243 |
| NM_017268 |
| NM_017278 |
| NM_017295 |
| NM_017313 |
| NM_017318 |
| NM_017322 |
| NM_017332 |
| NM_017344 |
| NM_017346 |
| NM_017352 |
| NM_017359 |
| NM_019124 |
| NM_019140 |
| NM_019169 |
| NM_019182 |
| NM_019194 |
| NM_019196 |
| NM_019218 |
| NM_019226 |
| NM_019234 |
| NM_019264 |
| NM_019277 |
| NM_019304 |
| NM_019348 |
| NM_019376 |
| NM_019377 |
| NM_021697 |
| NM_021739 |
| NM_021757 |
| NM_021758 |
| NM_021765 |
| NM_021850 |
| NM_022008 |
| NM_022209 |
| NM_022278 |
| NM_022289 |
| NM_022300 |
| NM_022301 |
| NM_022383 |
| NM_022387 |
| NM_022521 |
| NM_022585 |
| NM_022609 |
| NM_022674 |
| NM_022685 |
| NM_022850 |

TABLE 36-continued

CA3 - AI ANOVA DECREASE
GENBANK® ID

| |
|---|
| NM_022863 |
| NM_022869 |
| NM_022934 |
| NM_022962 |
| NM_023957 |
| NM_023960 |
| NM_023974 |
| NM_023975 |
| NM_023977 |
| NM_023979 |
| NM_024137 |
| NM_024139 |
| NM_024156 |
| NM_024161 |
| NM_024351 |
| NM_024362 |
| NM_024374 |
| NM_024403 |
| NM_024486 |
| NM_030835 |
| NM_031090 |
| NM_031138 |
| NM_031146 |
| NM_031152 |
| NM_031153 |
| NM_031235 |
| NM_031237 |
| NM_031325 |
| NM_031330 |
| NM_031334 |
| NM_031358 |
| NM_031360 |
| NM_031579 |
| NM_031603 |
| NM_031639 |
| NM_031662 |
| NM_031675 |
| NM_031676 |
| NM_031693 |
| NM_031718 |
| NM_031719 |
| NM_031728 |
| NM_031745 |
| NM_031757 |
| NM_031783 |
| NM_031785 |
| NM_031786 |
| NM_031802 |
| NM_031813 |
| NM_031824 |
| NM_031828 |
| NM_031969 |
| NM_031977 |
| NM_031978 |
| NM_031987 |
| NM_032057 |
| NM_032083 |
| NM_032614 |
| NM_052809 |
| NM_053291 |
| NM_053301 |
| NM_053316 |
| NM_053319 |
| NM_053337 |
| NM_053339 |
| NM_053346 |
| NM_053349 |
| NM_053351 |
| NM_053357 |
| NM_053404 |
| NM_053410 |
| NM_053420 |
| NM_053428 |
| NM_053441 |
| NM_053458 |
| NM_053490 |
| NM_053522 |

TABLE 36-continued

CA3 - AI ANOVA DECREASE
GENBANK® ID

| |
|---|
| NM_053556 |
| NM_053558 |
| NM_053588 |
| NM_053594 |
| NM_053605 |
| NM_053607 |
| NM_053623 |
| NM_053655 |
| NM_053682 |
| NM_053690 |
| NM_053693 |
| NM_053698 |
| NM_053707 |
| NM_053747 |
| NM_053748 |
| NM_053750 |
| NM_053764 |
| NM_053772 |
| NM_053775 |
| NM_053795 |
| NM_053801 |
| NM_053825 |
| NM_053868 |
| NM_053876 |
| NM_053888 |
| NM_053909 |
| NM_053928 |
| NM_053933 |
| NM_053947 |
| NM_053948 |
| NM_053979 |
| NM_054009 |
| NM_057098 |
| NM_057099 |
| NM_057108 |
| NM_057196 |
| NM_080402 |
| NM_080411 |
| NM_080481 |
| NM_080582 |
| NM_080781 |
| NM_080887 |
| NM_080902 |
| NM_130429 |
| NM_130746 |
| NM_130779 |
| NM_131904 |
| NM_133313 |
| NM_133427 |
| NM_133528 |
| NM_133539 |
| NM_133566 |
| NM_134383 |
| NM_134456 |
| NM_138519 |
| NM_138856 |
| NM_138865 |
| NM_138890 |
| NM_138910 |
| NM_138911 |
| NM_139097 |
| NM_139325 |
| NM_144758 |
| NM_145184 |
| NM_145772 |
| NM_145788 |
| NM_147211 |
| NM_153297 |
| NM_153630 |
| NM_171990 |
| NM_172039 |
| NM_172074 |
| NM_172243 |
| NM_172332 |
| NM_173133 |
| NM_173137 |
| NM_173154 |

TABLE 36-continued

CA3 - AI ANOVA DECREASE
GENBANK ® ID

| |
|---|
| NM_173290 |
| NM_173308 |
| NM_175595 |
| NM_177425 |
| NM_177929 |
| NM_181083 |
| NM_181473 |
| NM_181626 |
| NM_182814 |
| NM_182819 |
| NM_183052 |
| NM_183332 |
| NM_184050 |
| NM_198749 |
| NM_198757 |
| NM_198788 |
| NM_199094 |
| NM_199104 |
| NM_199385 |
| NM_199393 |
| NM_199410 |
| NM_201421 |
| NM_207617 |
| NM_212494 |
| NM_212519 |
| NM_212549 |
| NM_213559 |
| X53232 |
| XM_213362 |
| XM_213382 |
| XM_213782 |
| XM_213898 |
| XM_214021 |
| XM_214053 |
| XM_214241 |
| XM_214296 |
| XM_214420 |
| XM_214446 |
| XM_214505 |
| XM_214625 |
| XM_214701 |
| XM_214833 |
| XM_214954 |
| XM_215044 |
| XM_215113 |
| XM_215118 |
| XM_215178 |
| XM_215286 |
| XM_215416 |
| XM_215424 |
| XM_215481 |
| XM_215549 |
| XM_215570 |
| XM_215612 |
| XM_215706 |
| XM_215717 |
| XM_215751 |
| XM_215758 |
| XM_215769 |
| XM_215771 |
| XM_216013 |
| XM_216212 |
| XM_216378 |
| XM_216393 |
| XM_216398 |
| XM_216563 |
| XM_216643 |
| XM_216661 |
| XM_217019 |
| XM_217124 |
| XM_217464 |
| XM_217560 |
| XM_217587 |
| XM_217592 |
| XM_218196 |
| XM_218790 |
| XM_219525 |

TABLE 36-continued

CA3 - AI ANOVA DECREASE
GENBANK ® ID

| |
|---|
| XM_219685 |
| XM_219693 |
| XM_219801 |
| XM_219939 |
| XM_220047 |
| XM_220155 |
| XM_220167 |
| XM_220178 |
| XM_220269 |
| XM_220281 |
| XM_220428 |
| XM_220506 |
| XM_220534 |
| XM_220541 |
| XM_220753 |
| XM_220992 |
| XM_221050 |
| XM_221212 |
| XM_221276 |
| XM_221888 |
| XM_221941 |
| XM_221946 |
| XM_221962 |
| XM_222177 |
| XM_222214 |
| XM_222478 |
| XM_222670 |
| XM_222946 |
| XM_223485 |
| XM_223580 |
| XM_223981 |
| XM_224271 |
| XM_224332 |
| XM_224417 |
| XM_224478 |
| XM_225078 |
| XM_225138 |
| XM_225923 |
| XM_226014 |
| XM_226238 |
| XM_226422 |
| XM_227811 |
| XM_229106 |
| XM_230523 |
| XM_230531 |
| XM_230861 |
| XM_231148 |
| XM_231251 |
| XM_232252 |
| XM_232343 |
| XM_233231 |
| XM_233467 |
| XM_233609 |
| XM_233944 |
| XM_234011 |
| XM_234272 |
| XM_234483 |
| XM_235185 |
| XM_235224 |
| XM_235496 |
| XM_235497 |
| XM_236476 |
| XM_236745 |
| XM_236941 |
| XM_237291 |
| XM_237327 |
| XM_237787 |
| XM_237957 |
| XM_238334 |
| XM_238346 |
| XM_340874 |
| XM_340986 |
| XM_340987 |
| XM_340999 |
| XM_341071 |
| XM_341337 |
| XM_341354 |

TABLE 36-continued

CA3 - AI ANOVA DECREASE
GENBANK® ID

XM_341558
XM_341653
XM_341661
XM_341669
XM_341686
XM_341700
XM_341709
XM_341803
XM_341947
XM_342048
XM_342101
XM_342149
XM_342174
XM_342180
XM_342217
XM_342223
XM_342340
XM_342442
XM_342489
XM_342534
XM_342551
XM_342581
XM_342600
XM_342632
XM_342657
XM_342829
XM_342851
XM_342857
XM_342924
XM_343018
XM_343154
XM_343175
XM_343175
XM_343459
XM_343469
XM_343557
XM_343579
XM_344130
XM_344450
XM_344706
XM_344971
XM_345150
XM_345266
XM_345938
XM_573165
XM_573256
XM_574503
XM_574916
XM_574979
XM_574991
XM_576252
XM_578542

The genes in this set show abundance of expressed gene product(s) in the Aged Impaired population that are significantly decreased, as determined by ANOVA, compared to those abundances in Young and Aged Unimpaired populations combined. Therefore, compounds useful in treating cognitive impairment selected using these genes should increase the abundance or enhance the function of the expressed gene products of these genes.

Example 37

An ANOVA was conducted on the probe set signal values for all probe sets by combining two groups of animals and comparing them to the third group. An "AU ANOVA" was performed, where Aged Impaired were combined with Young and compared to Aged Unimpaired. All probe sets were considered in the statistical analysis based on the gcRMA method of data extraction from the perfect match sequences for each probe. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 37 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 37

CA3 - AU ANOVA POSITIVE CORRELATION
GENBANK® ID

AW525560
BF562800
M59859
NM_001002277
NM_001003401
NM_001004082
NM_001004220
NM_001005761
NM_001005889
NM_001006957
NM_001007616
NM_001008335
NM_001008368
NM_001008879
NM_001009692
NM_001009825
NM_001011915
NM_001012064
NM_001012157
NM_001012183
NM_001012504
NM_001017960
NM_001024371
NM_001024790
NM_001024906
NM_001029897
NM_001033961
NM_001034020
NM_001034131
NM_001034924
NM_012504
NM_012518
NM_012673
NM_012734
NM_012809
NM_012836
NM_012877
NM_012886
NM_013038
NM_013066
NM_013126
NM_013135
NM_013181
NM_017155
NM_017190
NM_017211
NM_017242
NM_017288
NM_017290
NM_017294
NM_017304
NM_017327
NM_019128
NM_019148
NM_019288
NM_019375

TABLE 37-continued

CA3 - AU ANOVA POSITIVE CORRELATION GENBANK ® ID

NM_020075
NM_020088
NM_021597
NM_021659
NM_021748
NM_021767
NM_021775
NM_022206
NM_022254
NM_022533
NM_022589
NM_022668
NM_022690
NM_022703
NM_022946
NM_023020
NM_024397
NM_030862
NM_030990
NM_031036
NM_031037
NM_031066
NM_031117
NM_031150
NM_031515
NM_031608
NM_031613
NM_031690
NM_031707
NM_031715
NM_031730
NM_031743
NM_032617
NM_053311
NM_053335
NM_053358
NM_053391
NM_053457
NM_053589
NM_053664
NM_053777
NM_053818
NM_053859
NM_053878
NM_053910
NM_053980
NM_054003
NM_057139
NM_057140
NM_057201
NM_080482
NM_080904
NM_133395
NM_133405
NM_133567
NM_133568
NM_134413
NM_138502
NM_138896
NM_138907
NM_139060
NM_144756
NM_145091
NM_145094
NM_148891
NM_153317
NM_172023
NM_173120
NM_175708
NM_175761
NM_181087
NM_181634
NM_184049
NM_199372
XM_213824
XM_214031
XM_214172
XM_214253
XM_214740
XM_214775
XM_215182
XM_215919
XM_216739
XM_217021
XM_217059
XM_217279
XM_217432
XM_218226
XM_218704
XM_220420
XM_220423
XM_221672
XM_222245
XM_224538
XM_224713
XM_226076
XM_227510
XM_231121
XM_232345
XM_232351
XM_232946
XM_232987
XM_233767
XM_233798
XM_234901
XM_234908
XM_235179
XM_235639
XM_236268
XM_237790
XM_238072
XM_238336
XM_239329
XM_240330
XM_241981
XM_340912
XM_341081
XM_341201
XM_341341
XM_341352
XM_341548
XM_341789
XM_341857
XM_341961
XM_342279
XM_342405
XM_342612
XM_342682
XM_342684
XM_343114
XM_343175
XM_343358
XM_343468
XM_343483
XM_343513
XM_343588
XM_344661
XM_344862
XM_345867

The genes in this set show abundance of expressed gene product(s) in the Aged Unimpaired population that are significantly decreased, as determined by ANOVA, compared to those abundances in Young and Aged Impaired populations combined. In addition, the abundance of expressed gene product(s) in the aged animals positively correlate with learning index of the animals, such that poorer learners have higher abundances of expressed gene products of the selected genes. Therefore, compounds useful in treating cognitive impairment selected using these genes should decrease the abundance or attenuate the function of the expressed gene products of these genes.

Example 38

An ANOVA was conducted on the probe set signal values for all probe sets by combining two groups of animals and comparing them to the third group. An "AU ANOVA" was performed, where Aged Impaired were combined with Young and compared to Aged Unimpaired. All probe sets were considered in the statistical analysis based on the gcRMA method of data extraction from the perfect match sequences for each probe. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 38 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 38

CA3 - AU ANOVA NEGATIVE CORRELATION
GENBANK ® ID

AA956668
AI716912
NM_001002807
NM_001005561
NM_001008773
NM_001008826
NM_001009651
NM_001011983
NM_001014044
NM_001017376
NM_001024274
NM_001025407
NM_012517
NM_012548
NM_013001
NM_013218
NM_017171
NM_019318
NM_019384
NM_020308
NM_022282
NM_022626
NM_022681
NM_022686
NM_031642
NM_031686
NM_031807
NM_031985
NM_033021
NM_053539
NM_053635
NM_053642
NM_053787
NM_053890
NM_080899
NM_133304
NM_134457
NM_138710
NM_138839

TABLE 38-continued

CA3 - AU ANOVA NEGATIVE CORRELATION
GENBANK ® ID

NM_138874
NM_138887
NM_139192
NM_181638
NM_199084
XM_213658
XM_214191
XM_214509
XM_214906
XM_215303
XM_215540
XM_215858
XM_215947
XM_216380
XM_218759
XM_219297
XM_222184
XM_224232
XM_228305
XM_228644
XM_230634
XM_230846
XM_232247
XM_232253
XM_233970
XM_234017
XM_234238
XM_236380
XM_238163
XM_342432
XM_343910
XM_344606
XM_345418
XM_347168
XM_573259

The genes in this set show abundance of expressed gene product(s) in the Aged Unimpaired population that are significantly increased, as determined by ANOVA, compared to those abundances in Young and Aged Impaired populations combined. In addition, the abundance of expressed gene product(s) in the aged animals negatively correlate with learning index of the animals, such that poorer learners have lower abundances of expressed gene products of the selected genes. Therefore, compounds useful in treating cognitive impairment selected using these genes should increase the abundance or enhance the function of the expressed gene products of these genes.

Example 39

An ANOVA was conducted on the probe set signal values for all probe sets by combining two groups of animals and comparing them to the third group. An "AU ANOVA" was performed, where Aged Impaired were combined with Young and compared to Aged Unimpaired. All probe sets were considered in the statistical analysis based on the gcRMA method of data extraction from the perfect match sequences for each probe. Any probe sets having a p-value less than 0.05 were considered significantly changed and the genes or plurality of genes selected.

Microarray Results

Table 39 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 39

CA3 - AU ANOVA INCREASE
GENBANK ® ID

AI071000
BI285065
NM_001004253
NM_001004273
NM_001005557
NM_001005907
NM_001007666
NM_001007704
NM_001007755
NM_001008293
NM_001008344
NM_001008521
NM_001011894
NM_001011941
NM_001012016
NM_001012021
NM_001012049
NM_001012087
NM_001012128
NM_001012160
NM_001012169
NM_001012174
NM_001012459
NM_001013077
NM_001013137
NM_001013148
NM_001013178
NM_001013193
NM_001013873
NM_001014790
NM_001015027
NM_001017381
NM_001024247
NM_001024275
NM_001025027
NM_001025123
NM_001025693
NM_001025708
NM_001025716
NM_001029909
NM_001031655
NM_001031660
NM_001033699
NM_001033705
NM_001034111
NM_001034164
NM_001034199
NM_012636
NM_012645
NM_012731
NM_012801
NM_012935
NM_012945
NM_012988
NM_013006
NM_013040
NM_013057
NM_016993
NM_017067
NM_017103
NM_017172
NM_017303
NM_017305
NM_019163
NM_019340
NM_019363
NM_022197
NM_022506
NM_022715
NM_022921
NM_024002
NM_024373
NM_024388
NM_024405
NM_024489
NM_030987
NM_030992

TABLE 39-continued

CA3 - AU ANOVA INCREASE
GENBANK ® ID

NM_031021
NM_031023
NM_031082
NM_031083
NM_031098
NM_031114
NM_031322
NM_031597
NM_031599
NM_031640
NM_031656
NM_031699
NM_031721
NM_031771
NM_031779
NM_031789
NM_031793
NM_031798
NM_053453
NM_053541
NM_053584
NM_053604
NM_053713
NM_053714
NM_053826
NM_053842
NM_053887
NM_053946
NM_053965
NM_053998
NM_057107
NM_057147
NM_130400
NM_130409
NM_130413
NM_133392
NM_133571
NM_133593
NM_133620
NM_134326
NM_134364
NM_134389
NM_138873
NM_138888
NM_139332
NM_139336
NM_145789
NM_172157
NM_173123
NM_181363
NM_181432
NM_182816
NM_182953
NM_183331
NM_199111
NM_199268
NM_199403
NM_201988
NM_207602
XM_213338
XM_213370
XM_213418
XM_213679
XM_214043
XM_214362
XM_214621
XM_216225
XM_216517
XM_216725
XM_217146
XM_217191
XM_217209
XM_217210
XM_217284
XM_219531
XM_220095
XM_220335

TABLE 39-continued

CA3 - AU ANOVA INCREASE
GENBANK ® ID

XM_220612
XM_220813
XM_221034
XM_221231
XM_221263
XM_221333
XM_222155
XM_222773
XM_223117
XM_223161
XM_223390
XM_223418
XM_223643
XM_223820
XM_224588
XM_224627
XM_224733
XM_225559
XM_225644
XM_225688
XM_225864
XM_226237
XM_226769
XM_226976
XM_227475
XM_227657
XM_231524
XM_232330
XM_232466
XM_232578
XM_233485
XM_233535
XM_233815
XM_234205
XM_234540
XM_234921
XM_234942
XM_235248
XM_236275
XM_236292
XM_236914
XM_237458
XM_237808
XM_238039
XM_238166
XM_341173
XM_341208
XM_341280
XM_341295
XM_341312
XM_341380
XM_341508
XM_341578
XM_341590
XM_341639
XM_341688
XM_342044
XM_342271
XM_342528
XM_342605
XM_342641
XM_342837
XM_343002
XM_343088
XM_343318
XM_343326
XM_343548
XM_343559
XM_344002
XM_345652
XM_347163
XM_575968
XM_576312

The genes in this set show abundance of expressed gene product(s) in the Aged Unimpaired population that are significantly increased, as determined by ANOVA, compared to those abundances in Young and Aged Impaired populations combined. Therefore, compounds useful in treating cognitive impairment selected using these genes should increase the abundance or enhance the function of the expressed gene products of these genes.

Example 40

An ANOVA was conducted on the probe set signal values for all probe sets by combining two groups of animals and comparing them to the third group. An "AU ANOVA" was performed, where Aged Impaired were combined with Young and compared to Aged Unimpaired. All probe sets were considered in the statistical analysis based on the gcRMA method of data extraction from the perfect match sequences for each probe. Any probe sets having a p-value less than 0.05 were considered significantly changed and the genes or plurality of genes selected.

Microarray Results

Table 40 shows the genes that were identified as being associated with cognitive impairment in this experiment. The reference sequence transcript ID (GENBANK®) number for the exemplar sequence) was used to identify genes considered significantly changed. When this exemplar ID was not available, a UniGene identifier was used in conjunction with the GENBANK® accession number.

TABLE 40

CA3 - AU ANOVA DECREASE
GENBANK ® ID

AW251888
BE111604
BI303536
NM_001004200
NM_001004206
NM_001004233
NM_001004262
NM_001005555
NM_001005560
NM_001005881
NM_001007607
NM_001008364
NM_001008694
NM_001009618
NM_001011925
NM_001011926
NM_001012004
NM_001012065
NM_001012066
NM_001012113
NM_001012175
NM_001013079
NM_001013103
NM_001013231
NM_001024269
NM_001025414
NM_001025649
NM_001025688
NM_001025722
NM_001025770
NM_001031845
NM_001033670
NM_001033681
NM_001033889
NM_001033914
NM_001033968
NM_001034009
NM_001034135
NM_012506
NM_012527
NM_012613
NM_012628
NM_012660

TABLE 40-continued

CA3 - AU ANOVA DECREASE
GENBANK® ID

NM_012686
NM_012700
NM_012755
NM_012756
NM_012776
NM_012798
NM_012841
NM_012918
NM_012941
NM_012947
NM_013073
NM_013199
NM_013222
NM_016990
NM_017008
NM_017049
NM_017051
NM_017053
NM_017102
NM_017204
NM_017253
NM_017262
NM_017312
NM_017319
NM_019133
NM_019164
NM_019224
NM_019306
NM_019326
NM_019343
NM_019378
NM_019621
NM_021681
NM_021739
NM_021760
NM_021835
NM_021847
NM_021859
NM_022185
NM_022262
NM_022267
NM_022382
NM_022386
NM_022507
NM_022675
NM_022693
NM_022864
NM_022953
NM_023101
NM_023972
NM_024000
NM_024146
NM_024163
NM_030846
NM_031008
NM_031056
NM_031081
NM_031097
NM_031147
NM_031331
NM_031342
NM_031518
NM_031522
NM_031595
NM_031614
NM_031646
NM_031654
NM_031667
NM_031692
NM_031765
NM_031776
NM_031777
NM_031820
NM_031831
NM_031975
NM_032062
NM_032616
NM_033359
NM_053310
NM_053409
NM_053435
NM_053440
NM_053486
NM_053573
NM_053620
NM_053684
NM_053788
NM_053837
NM_053846
NM_053894
NM_053955
NM_053972
NM_053973
NM_057116
NM_057136
NM_057152
NM_057207
NM_057209
NM_057213
NM_080583
NM_080896
NM_130420
NM_130428
NM_130755
NM_133406
NM_133414
NM_133582
NM_134336
NM_134376
NM_134400
NM_134404
NM_138921
NM_145090
NM_145781
NM_147209
NM_172075
NM_175754
NM_177481
NM_181092
NM_182668
NM_182842
NM_198749
NM_198758
NM_207599
NM_212458
XM_213437
XM_213777
XM_214313
XM_214316
XM_214673
XM_214720
XM_214751
XM_214899
XM_215371
XM_215451
XM_215467
XM_216835
XM_218432
XM_218615
XM_219529
XM_220232
XM_222103
XM_222662
XM_224389
XM_226439
XM_227282
XM_228114
XM_233737
XM_234514
XM_234909
XM_235156
XM_238177
XM_238280
XM_239780

TABLE 40-continued

| CA3 - AU ANOVA DECREASE GENBANK ® ID |
|---|
| XM_242062 |
| XM_243390 |
| XM_340886 |
| XM_340911 |
| XM_340967 |
| XM_341088 |
| XM_341091 |
| XM_341157 |
| XM_341896 |
| XM_341963 |
| XM_342244 |
| XM_342477 |
| XM_342653 |
| XM_342808 |
| XM_342823 |
| XM_342854 |
| XM_343581 |
| XM_343613 |
| XM_343839 |
| XM_345870 |
| XM_345909 |
| XM_345970 |
| XM_577103 |
| XM_578287 |

The genes in this set show abundance of expressed gene product(s) in the Aged Unimpaired population that are significantly decreased, as determined by ANOVA, compared to those abundances in Young and Aged Impaired populations combined. Therefore, compounds useful in treating cognitive impairment selected using these genes should decrease the abundance or attenuate the function of the expressed gene products of these genes.

Example 41

An ANOVA was conducted on the probe set signal values for all probe sets by combining two groups of animals and comparing them to the third group. An "AI ANOVA" was performed, where Aged Unimpaired were combined with Young and compared to Aged Impaired. All probe sets were considered in the statistical analysis based on the gcRMA method of data extraction from the perfect match sequences for each probe. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 41 shows the genes that were identified as being associated with cognitive impairment in this experiment. The reference sequence transcript ID (GENBANK®) number for the exemplar sequence) was used to identify genes considered significantly changed. When this exemplar ID was not available, a UniGene identifier was used in conjunction with the GENBANK® accession number.

TABLE 41

| DG - AI ANOVA POSITIVE CORRELATION GENBANK ® ID |
|---|
| AA892549 |
| AF023090 |
| AI317821 |
| AI717047 |
| BG662522 |
| BI298090 |
| BM390128 |
| BM391371 |
| NM_001001513 |
| NM_001002815 |
| NM_001002828 |
| NM_001004080 |
| NM_001004081 |
| NM_001004090 |
| NM_001004199 |
| NM_001004209 |
| NM_001004247 |
| NM_001004254 |
| NM_001004255 |
| NM_001004273 |
| NM_001005383 |
| NM_001005539 |
| NM_001005872 |
| NM_001005898 |
| NM_001005902 |
| NM_001006967 |
| NM_001006968 |
| NM_001006987 |
| NM_001006989 |
| NM_001007146 |
| NM_001007616 |
| NM_001007624 |
| NM_001007625 |
| NM_001007654 |
| NM_001007682 |
| NM_001007691 |
| NM_001007712 |
| NM_001008279 |
| NM_001008319 |
| NM_001008324 |
| NM_001008356 |
| NM_001008374 |
| NM_001008509 |
| NM_001009474 |
| NM_001009536 |
| NM_001009625 |
| NM_001009686 |
| NM_001009690 |
| NM_001009693 |
| NM_001009708 |
| NM_001009973 |
| NM_001011891 |
| NM_001011893 |
| NM_001011903 |
| NM_001011906 |
| NM_001011910 |
| NM_001011920 |
| NM_001011946 |
| NM_001011958 |
| NM_001011970 |
| NM_001011974 |
| NM_001012004 |
| NM_001012030 |
| NM_001012050 |
| NM_001012051 |
| NM_001012067 |
| NM_001012083 |
| NM_001012106 |
| NM_001012120 |
| NM_001012159 |
| NM_001012161 |
| NM_001012171 |
| NM_001012180 |
| NM_001012217 |
| NM_001012235 |
| NM_001013034 |
| NM_001013046 |
| NM_001013070 |
| NM_001013082 |

TABLE 41-continued

DG - AI ANOVA POSITIVE CORRELATION
GENBANK® ID

| |
|---|
| NM_001013086 |
| NM_001013087 |
| NM_001013105 |
| NM_001013118 |
| NM_001013121 |
| NM_001013167 |
| NM_001013174 |
| NM_001013206 |
| NM_001013231 |
| NM_001013874 |
| NM_001014772 |
| NM_001015005 |
| NM_001024256 |
| NM_001024261 |
| NM_001024746 |
| NM_001024773 |
| NM_001025123 |
| NM_001025130 |
| NM_001025142 |
| NM_001025152 |
| NM_001025625 |
| NM_001025633 |
| NM_001025664 |
| NM_001025678 |
| NM_001025716 |
| NM_001031641 |
| NM_001031644 |
| NM_001033683 |
| NM_001033696 |
| NM_001033699 |
| NM_001033707 |
| NM_001033715 |
| NM_001033852 |
| NM_001033866 |
| NM_001033868 |
| NM_001033926 |
| NM_001033951 |
| NM_001033968 |
| NM_001033987 |
| NM_001034020 |
| NM_001034068 |
| NM_001034090 |
| NM_001034110 |
| NM_001034998 |
| NM_001034999 |
| NM_001035221 |
| NM_012500 |
| NM_012512 |
| NM_012527 |
| NM_012543 |
| NM_012569 |
| NM_012577 |
| NM_012595 |
| NM_012618 |
| NM_012628 |
| NM_012663 |
| NM_012732 |
| NM_012744 |
| NM_012749 |
| NM_012777 |
| NM_012788 |
| NM_012816 |
| NM_012820 |
| NM_012838 |
| NM_012884 |
| NM_012913 |
| NM_012963 |
| NM_012971 |
| NM_012993 |
| NM_013000 |
| NM_013013 |
| NM_013022 |
| NM_013088 |
| NM_013091 |
| NM_013154 |
| NM_013156 |
| NM_013164 |
| NM_013194 |
| NM_013198 |
| NM_013226 |
| NM_016990 |
| NM_017051 |
| NM_017052 |
| NM_017060 |
| NM_017068 |
| NM_017109 |
| NM_017116 |
| NM_017125 |
| NM_017132 |
| NM_017137 |
| NM_017148 |
| NM_017181 |
| NM_017204 |
| NM_017212 |
| NM_017216 |
| NM_017223 |
| NM_017232 |
| NM_017234 |
| NM_017264 |
| NM_017274 |
| NM_017288 |
| NM_017317 |
| NM_017320 |
| NM_017340 |
| NM_017343 |
| NM_019124 |
| NM_019132 |
| NM_019141 |
| NM_019204 |
| NM_019211 |
| NM_019226 |
| NM_019232 |
| NM_019242 |
| NM_019253 |
| NM_019257 |
| NM_019272 |
| NM_019289 |
| NM_019359 |
| NM_019362 |
| NM_020308 |
| NM_021663 |
| NM_021694 |
| NM_021703 |
| NM_021746 |
| NM_021748 |
| NM_021766 |
| NM_021847 |
| NM_021859 |
| NM_021863 |
| NM_022207 |
| NM_022226 |
| NM_022265 |
| NM_022281 |
| NM_022286 |
| NM_022382 |
| NM_022390 |
| NM_022499 |
| NM_022500 |
| NM_022502 |
| NM_022523 |
| NM_022526 |
| NM_022538 |
| NM_022592 |
| NM_022595 |
| NM_022596 |
| NM_022597 |
| NM_022601 |
| NM_022617 |
| NM_022699 |
| NM_022701 |
| NM_022799 |
| NM_022853 |
| NM_022939 |
| NM_023972 |

TABLE 41-continued

DG - AI ANOVA POSITIVE CORRELATION
GENBANK® ID

NM_023978
NM_024155
NM_024359
NM_024374
NM_024399
NM_024404
NM_030826
NM_030992
NM_031022
NM_031035
NM_031057
NM_031099
NM_031114
NM_031120
NM_031147
NM_031149
NM_031357
NM_031509
NM_031525
NM_031553
NM_031554
NM_031589
NM_031596
NM_031632
NM_031654
NM_031657
NM_031664
NM_031683
NM_031711
NM_031729
NM_031745
NM_031752
NM_031770
NM_031774
NM_031786
NM_031789
NM_031812
NM_031816
NM_031827
NM_031830
NM_031837
NM_031970
NM_031981
NM_032067
NM_032416
NM_032619
NM_053323
NM_053401
NM_053411
NM_053448
NM_053462
NM_053467
NM_053507
NM_053538
NM_053555
NM_053598
NM_053599
NM_053600
NM_053604
NM_053665
NM_053698
NM_053750
NM_053776
NM_053777
NM_053794
NM_053804
NM_053851
NM_053870
NM_053886
NM_053911
NM_053927
NM_053936
NM_053959
NM_053985
NM_054001
NM_057100
NM_057114
NM_057118
NM_057131
NM_057192
NM_057197
NM_057204
NM_057208
NM_057210
NM_080480
NM_080577
NM_080691
NM_080767
NM_080773
NM_080888
NM_080910
NM_130409
NM_130416
NM_133398
NM_133401
NM_133404
NM_133421
NM_133551
NM_133585
NM_134376
NM_134390
NM_134410
NM_134415
NM_134449
NM_134456
NM_134468
NM_138508
NM_138877
NM_138889
NM_138896
NM_138917
NM_139107
NM_139110
NM_139256
NM_139325
NM_139329
NM_147177
NM_147210
NM_153469
NM_153628
NM_153630
NM_172009
NM_172033
NM_172334
NM_173116
NM_175578
NM_175582
NM_175765
NM_177927
NM_181388
NM_181475
NM_182953
NM_183328
NM_183402
NM_198787
NM_199087
NM_199108
NM_199118
NM_199119
NM_199384
NM_199388
NM_199408
NM_206847
NM_207591
NM_207599
NM_212463
NM_212491
NM_212509
XM_213329
XM_213342
XM_213463
XM_213673
XM_213677
XM_213729

TABLE 41-continued

DG - AI ANOVA POSITIVE CORRELATION
GENBANK ® ID

XM_213739
XM_213824
XM_213832
XM_213972
XM_213993
XM_214147
XM_214172
XM_214279
XM_214518
XM_214843
XM_214859
XM_214963
XM_214968
XM_215028
XM_215101
XM_215113
XM_215177
XM_215222
XM_215285
XM_215674
XM_215733
XM_215754
XM_215935
XM_215939
XM_216124
XM_216230
XM_216306
XM_216386
XM_216407
XM_216515
XM_216565
XM_216629
XM_216704
XM_216740
XM_216835
XM_216872
XM_216968
XM_217061
XM_217195
XM_217478
XM_217740
XM_218336
XM_218816
XM_218858
XM_219001
XM_219515
XM_219885
XM_219948
XM_220512
XM_220574
XM_220775
XM_221297
XM_221747
XM_222661
XM_223012
XM_223125
XM_223597
XM_223938
XM_224232
XM_224630
XM_224788
XM_225014
XM_225259
XM_225457
XM_225726
XM_226237
XM_226987
XM_227074
XM_228044
XM_228701
XM_230291
XM_230637
XM_231162
XM_232323
XM_232745
XM_232855
XM_233415
XM_233761
XM_233798
XM_234008
XM_234205
XM_234394
XM_235400
XM_235426
XM_235518
XM_235657
XM_236189
XM_236192
XM_236362
XM_236468
XM_236659
XM_236687
XM_237415
XM_237787
XM_238019
XM_238155
XM_241632
XM_242032
XM_243652
XM_340798
XM_340818
XM_340825
XM_340997
XM_341051
XM_341052
XM_341086
XM_341157
XM_341704
XM_341785
XM_341790
XM_341796
XM_341799
XM_341826
XM_341867
XM_341882
XM_341934
XM_341940
XM_341957
XM_342002
XM_342409
XM_342542
XM_342866
XM_342918
XM_343119
XM_343157
XM_343268
XM_343336
XM_343396
XM_343564
XM_343570
XM_343773
XM_343776
XM_343986
XM_344286
XM_344403
XM_344409
XM_344870
XM_344970
XM_345477
XM_345535
XM_345870
XM_346083
XM_573258
XM_574670
XM_577023

The genes in this set show abundance of expressed gene product(s) in the Aged Impaired population that are significantly increased, as determined by ANOVA, compared to those abundances in Young and Aged Unimpaired populations combined. In addition, the abundance of expressed gene product(s) in the aged animals positively correlate with learning index of the animals, such that poorer learners have higher abundances of expressed gene products of the selected genes. Therefore, compounds useful in treating cognitive impairment selected using these genes should decrease the abundance or attenuate the function of the expressed gene products of these genes.

Example 42

An ANOVA was conducted on the probe set signal values for all probe sets by combining two groups of animals and comparing them to the third group. An "AI ANOVA" was performed, where Aged Unimpaired were combined with Young and compared to Aged Impaired. All probe sets were considered in the statistical analysis based on the gcRMA method of data extraction from the perfect match sequences for each probe. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 42 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 42

| DG - AI ANOVA NEGATIVE CORRELATION GENBANK ® ID |
|---|
| BF557865 |
| BM391206 |
| NM_001004102 |
| NM_001009689 |
| NM_001013071 |
| NM_001024238 |
| NM_013111 |
| NM_024355 |
| NM_031123 |
| NM_031127 |
| NM_053775 |
| NM_134383 |
| NM_173094 |
| NM_212504 |
| XM_218939 |
| XM_219292 |
| XM_219879 |
| XM_221074 |
| XM_223729 |
| XM_224733 |
| XM_230288 |
| XM_231453 |
| XM_234508 |
| XM_343446 |
| XM_344594 |
| XM_345938 |

The genes in this set show abundance of expressed gene product(s) in the Aged Impaired population that are significantly decreased, as determined by ANOVA, compared to those abundances in Young and Aged Unimpaired populations combined. In addition, the abundance of expressed gene product(s) in the aged animals negatively correlate with learning index of the animals, such that poorer learners have lower abundances of expressed gene products of the selected genes. Therefore, compounds useful in treating cognitive impairment selected using these genes should increase the abundance or enhance the function of the expressed gene products of these genes.

Example 43

An ANOVA was conducted on the probe set signal values for all probe sets by combining two groups of animals and comparing them to the third group. An "AI ANOVA" was performed, where Aged Unimpaired were combined with Young and compared to Aged Impaired. All probe sets were considered in the statistical analysis based on the gcRMA method of data extraction from the perfect match sequences for each probe. Any probe sets having a p-value less than 0.05 were considered significantly changed and the genes or plurality of genes selected.

Microarray Results

Table 43 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 43

| DG - AI ANOVA INCREASE GENBANK ® ID |
|---|
| AI103331 |
| AI235284 |
| AW526364 |
| BI291997 |
| NM_001001511 |
| NM_001001516 |
| NM_001002016 |
| NM_001002802 |
| NM_001002835 |
| NM_001004076 |
| NM_001004099 |
| NM_001004218 |
| NM_001004245 |
| NM_001005528 |
| NM_001005529 |
| NM_001005893 |
| NM_001005907 |
| NM_001006971 |
| NM_001007001 |
| NM_001007557 |
| NM_001007677 |
| NM_001007684 |
| NM_001007749 |
| NM_001007755 |
| NM_001007802 |
| NM_001008315 |
| NM_001008725 |
| NM_001008767 |
| NM_001008768 |
| NM_001008829 |
| NM_001009172 |
| NM_001009502 |
| NM_001009623 |
| NM_001009668 |
| NM_001009669 |
| NM_001009683 |
| NM_001011919 |
| NM_001011985 |
| NM_001012147 |
| NM_001012190 |
| NM_001012464 |
| NM_001013047 |
| NM_001013059 |
| NM_001013072 |

TABLE 43-continued

DG - AI ANOVA INCREASE
GENBANK ® ID

NM_001013081
NM_001013135
NM_001013179
NM_001013193
NM_001013204
NM_001013207
NM_001013210
NM_001013233
NM_001013246
NM_001015026
NM_001017382
NM_001024268
NM_001024771
NM_001024775
NM_001024782
NM_001025423
NM_001025630
NM_001025721
NM_001030026
NM_001030041
NM_001033653
NM_001033656
NM_001033757
NM_001034004
NM_001034164
NM_012515
NM_012523
NM_012532
NM_012546
NM_012562
NM_012576
NM_012578
NM_012614
NM_012650
NM_012701
NM_012703
NM_012722
NM_012740
NM_012771
NM_012856
NM_012862
NM_012886
NM_012925
NM_012940
NM_012974
NM_013015
NM_013070
NM_013104
NM_013107
NM_013122
NM_013135
NM_013137
NM_013146
NM_017009
NM_017024
NM_017037
NM_017043
NM_017062
NM_017139
NM_017142
NM_017200
NM_017224
NM_017262
NM_017351
NM_019143
NM_019144
NM_019219
NM_019249
NM_019266
NM_019312
NM_019313
NM_019318
NM_019335
NM_019346
NM_019386
NM_019904
NM_019905

TABLE 43-continued

DG - AI ANOVA INCREASE
GENBANK ® ID

NM_020082
NM_020088
NM_021578
NM_021582
NM_021690
NM_021769
NM_021771
NM_021989
NM_022215
NM_022244
NM_022251
NM_022257
NM_022266
NM_022270
NM_022285
NM_022401
NM_022504
NM_022516
NM_022531
NM_022677
NM_022692
NM_022866
NM_024129
NM_024131
NM_024133
NM_024353
NM_024358
NM_024369
NM_024372
NM_024400
NM_030843
NM_030847
NM_030863
NM_030872
NM_030987
NM_031018
NM_031031
NM_031118
NM_031140
NM_031145
NM_031242
NM_031320
NM_031332
NM_031511
NM_031514
NM_031549
NM_031560
NM_031630
NM_031728
NM_031739
NM_031797
NM_031814
NM_031818
NM_052804
NM_053356
NM_053455
NM_053485
NM_053503
NM_053536
NM_053554
NM_053560
NM_053570
NM_053583
NM_053612
NM_053618
NM_053654
NM_053670
NM_053684
NM_053796
NM_053838
NM_053857
NM_053882
NM_053896
NM_053933
NM_053936
NM_053992
NM_057107

TABLE 43-continued

DG - AI ANOVA INCREASE
GENBANK ® ID

| |
|---|
| NM_057200 |
| NM_057211 |
| NM_080479 |
| NM_080584 |
| NM_080698 |
| NM_080899 |
| NM_131911 |
| NM_133296 |
| NM_133298 |
| NM_133305 |
| NM_133307 |
| NM_133317 |
| NM_133522 |
| NM_133526 |
| NM_133548 |
| NM_133598 |
| NM_133605 |
| NM_133624 |
| NM_134419 |
| NM_138502 |
| NM_138521 |
| NM_138542 |
| NM_139185 |
| NM_139216 |
| NM_139255 |
| NM_144757 |
| NM_145091 |
| NM_147205 |
| NM_147206 |
| NM_172022 |
| NM_172029 |
| NM_173118 |
| NM_173145 |
| NM_175579 |
| NM_175756 |
| NM_181087 |
| NM_181368 |
| NM_181377 |
| NM_183330 |
| NM_184051 |
| NM_198786 |
| NM_199093 |
| NM_199208 |
| NM_199270 |
| NM_206849 |
| NM_207596 |
| NM_207598 |
| NM_207609 |
| NM_212466 |
| NM_212505 |
| NM_212523 |
| NM_212525 |
| NM_212547 |
| XM_213408 |
| XM_213421 |
| XM_213460 |
| XM_213526 |
| XM_213611 |
| XM_214344 |
| XM_214441 |
| XM_214526 |
| XM_214583 |
| XM_214673 |
| XM_214721 |
| XM_214769 |
| XM_214935 |
| XM_214993 |
| XM_215076 |
| XM_215095 |
| XM_215117 |
| XM_215372 |
| XM_215376 |
| XM_215424 |
| XM_215576 |
| XM_215578 |
| XM_216018 |
| XM_216688 |

TABLE 43-continued

DG - AI ANOVA INCREASE
GENBANK ® ID

| |
|---|
| XM_218368 |
| XM_218963 |
| XM_218977 |
| XM_219045 |
| XM_219470 |
| XM_219966 |
| XM_220333 |
| XM_220398 |
| XM_220644 |
| XM_220810 |
| XM_220982 |
| XM_221272 |
| XM_221380 |
| XM_221387 |
| XM_221916 |
| XM_222636 |
| XM_223583 |
| XM_223781 |
| XM_224296 |
| XM_224538 |
| XM_224561 |
| XM_225196 |
| XM_225548 |
| XM_225625 |
| XM_225631 |
| XM_225644 |
| XM_225997 |
| XM_226016 |
| XM_226213 |
| XM_227066 |
| XM_228197 |
| XM_230036 |
| XM_230462 |
| XM_230647 |
| XM_231134 |
| XM_231402 |
| XM_232283 |
| XM_232622 |
| XM_233779 |
| XM_235024 |
| XM_235049 |
| XM_235710 |
| XM_236458 |
| XM_236560 |
| XM_237371 |
| XM_237754 |
| XM_237792 |
| XM_238447 |
| XM_240178 |
| XM_240311 |
| XM_242644 |
| XM_242982 |
| XM_243637 |
| XM_243815 |
| XM_340939 |
| XM_341227 |
| XM_341448 |
| XM_341509 |
| XM_341540 |
| XM_341584 |
| XM_341784 |
| XM_341857 |
| XM_341877 |
| XM_341880 |
| XM_342072 |
| XM_342092 |
| XM_342271 |
| XM_342284 |
| XM_342317 |
| XM_342432 |
| XM_342759 |
| XM_342829 |
| XM_342905 |
| XM_342979 |
| XM_343058 |
| XM_343065 |
| XM_343126 |

TABLE 43-continued

DG - AI ANOVA INCREASE
GENBANK ® ID

XM_343259
XM_343334
XM_343479
XM_343619
XM_344421
XM_344524
XM_345584
XM_345702
XM_345789
XM_345825
XM_573544
XM_573983
XM_574161
XM_574618
XM_575585
XM_576363
XM_576401
XM_580221

The genes in this set show abundance of expressed gene product(s) in the Aged Impaired population that are significantly increased, as determined by ANOVA, compared to those abundances in Young and Aged Unimpaired populations combined. Therefore, compounds useful in treating cognitive impairment selected using these genes should decrease the abundance or attenuate the function of the expressed gene products of these genes.

Example 44

An ANOVA was conducted on the probe set signal values for all probe sets by combining two groups of animals and comparing them to the third group. An "AI ANOVA" was performed, where Aged Unimpaired were combined with Young and compared to Aged Impaired. All probe sets were considered in the statistical analysis based on the gcRMA method of data extraction from the perfect match sequences for each probe. Any probe sets having a p-value less than 0.05 were considered significantly changed and the genes or plurality of genes selected.

Microarray Results

Table 44 shows the genes that were identified as being associated with cognitive impairment in this experiment. The reference sequence transcript ID (GENBANK®) number for the exemplar sequence) was used to identify genes considered significantly changed. When this exemplar ID was not available, a UniGene identifier was used in conjunction with the GENBANK® accession number.

TABLE 44

DG - AI ANOVA DECREASE
GENBANK ® ID

NM_001005530
NM_001005885
NM_001006994
NM_001007000
NM_001007607
NM_001008353
NM_001008553
NM_001009719
NM_001010965
NM_001011942
NM_001012144
NM_001013209
NM_001017376
NM_001024964
NM_001025136
NM_001025400
NM_001031645
NM_001033684
NM_012585
NM_012934
NM_013066
NM_017030
NM_017093
NM_017197
NM_017259
NM_017290
NM_017318
NM_017357
NM_019264
NM_020097
NM_021597
NM_021702
NM_021760
NM_022615
NM_022688
NM_024364
NM_031082
NM_031318
NM_031571
NM_031613
NM_053301
NM_053340
NM_053360
NM_053441
NM_053883
NM_080397
NM_133315
NM_133387
NM_133562
NM_144758
NM_172034
NM_173325
NM_199081
XM_214701
XM_215134
XM_215883
XM_216477
XM_217115
XM_219723
XM_220607
XM_221888
XM_221941
XM_221962
XM_222223
XM_222460
XM_222662
XM_224474
XM_224947
XM_226624
XM_233260
XM_233490
XM_233679
XM_234470
XM_236614
XM_237307
XM_239171
XM_340856
XM_340999
XM_341241
XM_341709
XM_341983
XM_342107
XM_343817
XM_343919
XM_347168
XM_575397

The genes in this set show abundance of expressed gene product(s) in the Aged Impaired population that are significantly decreased, as determined by ANOVA, compared to those abundances in Young and Aged Unimpaired populations combined. Therefore, compounds useful in treating cognitive impairment selected using these genes should increase the abundance or enhance the function of the expressed gene products of these genes.

Example 45

An ANOVA was conducted on the probe set signal values for all probe sets by combining two groups of animals and comparing them to the third group. An "AU ANOVA" was performed, where Aged Impaired were combined with Young and compared to Aged Unimpaired. All probe sets were considered in the statistical analysis based on the gcRMA method of data extraction from the perfect match sequences for each probe. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 45 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 45

| DG - AU ANOVA POSITIVE CORRELATION GENBANK ® ID |
| --- |
| AI501759 |
| BE329232 |
| NM_001003975 |
| NM_001004253 |
| NM_001004269 |
| NM_001004275 |
| NM_001005381 |
| NM_001005876 |
| NM_001006960 |
| NM_001006963 |
| NM_001006981 |
| NM_001007020 |
| NM_001007620 |
| NM_001007714 |
| NM_001007731 |
| NM_001007744 |
| NM_001008277 |
| NM_001008291 |
| NM_001008298 |
| NM_001008338 |
| NM_001008352 |
| NM_001008508 |
| NM_001008556 |
| NM_001008766 |
| NM_001008839 |
| NM_001008891 |
| NM_001009602 |
| NM_001009619 |
| NM_001009637 |
| NM_001009657 |
| NM_001009825 |
| NM_001011964 |
| NM_001011975 |
| NM_001011983 |
| NM_001012138 |
| NM_001012208 |
| NM_001012504 |

TABLE 45-continued

| DG - AU ANOVA POSITIVE CORRELATION GENBANK ® ID |
| --- |
| NM_001013114 |
| NM_001013245 |
| NM_001017385 |
| NM_001017386 |
| NM_001024745 |
| NM_001024756 |
| NM_001024785 |
| NM_001024874 |
| NM_001025409 |
| NM_001025660 |
| NM_001025688 |
| NM_001025695 |
| NM_001025735 |
| NM_001025748 |
| NM_001030023 |
| NM_001031648 |
| NM_001031653 |
| NM_001031659 |
| NM_001033065 |
| NM_001033079 |
| NM_001033670 |
| NM_001033702 |
| NM_001033870 |
| NM_001034009 |
| NM_001034026 |
| NM_001034129 |
| NM_001034834 |
| NM_012615 |
| NM_012809 |
| NM_012836 |
| NM_012991 |
| NM_012998 |
| NM_013053 |
| NM_013192 |
| NM_017029 |
| NM_017040 |
| NM_017075 |
| NM_017190 |
| NM_017201 |
| NM_019133 |
| NM_019271 |
| NM_019352 |
| NM_019379 |
| NM_020099 |
| NM_021262 |
| NM_021697 |
| NM_021770 |
| NM_021835 |
| NM_021869 |
| NM_022198 |
| NM_022282 |
| NM_022296 |
| NM_022498 |
| NM_023971 |
| NM_024147 |
| NM_030989 |
| NM_031028 |
| NM_031125 |
| NM_031137 |
| NM_031139 |
| NM_031152 |
| NM_031515 |
| NM_031521 |
| NM_031528 |
| NM_031600 |
| NM_031641 |
| NM_031646 |
| NM_031768 |
| NM_031783 |
| NM_031979 |
| NM_032066 |
| NM_053291 |
| NM_053404 |
| NM_053440 |
| NM_053457 |
| NM_053508 |
| NM_053561 |

TABLE 45-continued

DG - AU ANOVA POSITIVE CORRELATION GENBANK® ID

NM_053620
NM_053770
NM_053779
NM_053811
NM_053818
NM_053842
NM_053850
NM_053874
NM_053928
NM_053965
NM_053999
NM_054004
NM_054006
NM_057132
NM_057141
NM_080478
NM_080887
NM_080895
NM_130406
NM_130826
NM_130894
NM_133310
NM_133569
NM_133582
NM_133594
NM_133615
NM_138528
NM_138840
NM_138899
NM_138900
NM_139109
NM_139186
NM_139194
NM_139254
NM_144754
NM_145085
NM_145878
NM_152935
NM_153297
NM_171994
NM_172157
NM_173115
NM_173290
NM_175595
NM_175603
NM_175838
NM_181081
NM_182671
NM_182820
NM_183332
NM_184049
NM_198771
NM_198789
NM_199372
NM_199380
NM_199500
XM_213382
XM_213437
XM_213569
XM_214155
XM_214238
XM_214420
XM_214570
XM_214625
XM_214817
XM_215659
XM_215701
XM_215847
XM_215985
XM_216041
XM_216169
XM_216198
XM_216367
XM_216400
XM_216524
XM_216801
XM_217124
XM_217592
XM_217806
XM_218720
XM_218949
XM_219693
XM_220884
XM_220982
XM_221100
XM_223227
XM_223837
XM_224169
XM_224429
XM_225468
XM_225711
XM_225983
XM_232315
XM_233231
XM_235552
XM_235640
XM_237999
XM_238205
XM_238280
XM_238380
XM_240330
XM_340750
XM_340775
XM_341058
XM_341120
XM_341653
XM_341666
XM_341714
XM_341856
XM_341878
XM_341961
XM_342004
XM_342286
XM_342300
XM_342489
XM_342521
XM_342532
XM_342632
XM_342872
XM_343006
XM_343034
XM_343117
XM_343175
XM_343459
XM_343513
XM_343922
XM_344113
XM_347236
XM_577103

The genes in this set show abundance of expressed gene product(s) in the Aged Unimpaired population that are significantly decreased, as determined by ANOVA, compared to those abundances in Young and Aged Impaired populations combined. In addition, the abundance of expressed gene product(s) in the aged animals positively correlate with learning index of the animals, such that poorer learners have higher abundances of expressed gene products of the selected genes. Therefore, compounds useful in treating cognitive impairment selected using these genes should decrease the abundance or attenuate the function of the expressed gene products of these genes.

Example 46

An ANOVA was conducted on the probe set signal values for all probe sets by combining two groups of animals and comparing them to the third group. An "AU ANOVA" was performed, where Aged Impaired were combined with Young and compared to Aged Unimpaired. All probe sets were considered in the statistical analysis based on the gcRMA method of data extraction from the perfect match sequences for each probe. Any probe sets having a p-value less than 0.05 were considered significantly changed and the genes or plurality of genes selected.

Pearson's correlations comparing probe set signal values to learning indices were then calculated for the aged animals (excluding young) across all present probe sets. Again, correlations representing a p-value of less than 0.05 were considered significantly changed.

Microarray Results

Table 46 shows the genes that were identified as being associated with cognitive impairment in this experiment. The reference sequence transcript ID (GENBANK®) number for the exemplar sequence) was used to identify genes considered significantly changed. When this exemplar ID was not available, a UniGene identifier was used in conjunction with the GENBANK® accession number.

TABLE 46

DG - AU ANOVA NEGATIVE CORRELATION
GENBANK ® ID

BF411876
NM_001008511
NM_001012093
NM_001013090
NM_001024258
NM_001024865
NM_001034994
NM_013159
NM_022202
NM_022236
NM_022518
NM_031635
NM_031698
NM_053416
NM_053621
NM_133593
NM_134326
NM_172039
NM_181362
NM_212498
XM_214253
XM_215942
XM_215947
XM_215990
XM_220222
XM_220813
XM_221043
XM_226666
XM_233808
XM_341215
XM_342580
XM_344785

The genes in this set show abundance of expressed gene product(s) in the Aged Unimpaired population that are significantly increased, as determined by ANOVA, compared to those abundances in Young and Aged Impaired populations combined. In addition, the abundance of expressed gene product(s) in the aged animals negatively correlate with learning index of the animals, such that poorer learners have lower abundances of expressed gene products of the selected genes. Therefore, compounds useful in treating cognitive impairment selected using these genes should increase the abundance or enhance the function of the expressed gene products of these genes.

Example 47

An ANOVA was conducted on the probe set signal values for all probe sets by combining two groups of animals and comparing them to the third group. An "AU ANOVA" was performed, where Aged Impaired were combined with Young and compared to Aged Unimpaired. All probe sets were considered in the statistical analysis based on the gcRMA method of data extraction from the perfect match sequences for each probe. Any probe sets having a p-value less than 0.05 were considered significantly changed and the genes or plurality of genes selected.

Microarray Results

Table 47 shows the genes that were identified as being associated with cognitive impairment in this experiment. The reference sequence transcript ID (GENBANK®) number for the exemplar sequence) was used to identify genes considered significantly changed. When this exemplar ID was not available, a UniGene identifier was used in conjunction with the GENBANK® accession number.

TABLE 47

DG - AU ANOVA INCREASE
GENBANK ® ID

NM_001002831
NM_001005888
NM_001007680
NM_001007704
NM_001012092
NM_001012195
NM_001013120
NM_001024767
NM_001025125
NM_001025722
NM_001033701
NM_012853
NM_012935
NM_012959
NM_013126
NM_016994
NM_019170
NM_021688
NM_022269
NM_022525
NM_022684
NM_023095
NM_023977
NM_024378
NM_031569
NM_031610
NM_031742
NM_031751
NM_040669
NM_052807
NM_053355
NM_053442
NM_053644
NM_053826
NM_057196
NM_080897
NM_133302
NM_133558
NM_138922
NM_153740
NM_172327
NM_213562
XM_213921
XM_214730
XM_214906
XM_215742
XM_215949
XM_215984
XM_217246
XM_217293
XM_217837
XM_218293
XM_218432
XM_221037
XM_222155
XM_224720

TABLE 47-continued

DG - AU ANOVA INCREASE
GENBANK ® ID

XM_225168
XM_225253
XM_226315
XM_226976
XM_231143
XM_232253
XM_232735
XM_233421
XM_234238
XM_235986
XM_340785
XM_340879
XM_340935
XM_341590
XM_343146
XM_344785
XM_577078

The genes in this set show abundance of expressed gene product(s) in the Aged Unimpaired population that are significantly increased, as determined by ANOVA, compared to those abundances in Young and Aged Impaired populations combined. Therefore, compounds useful in treating cognitive impairment selected using these genes should increase the abundance or enhance the function of the expressed gene products of these genes.

Example 48

An ANOVA was conducted on the probe set signal values for all probe sets by combining two groups of animals and comparing them to the third group. An "AU ANOVA" was performed, where Aged Impaired were combined with Young and compared to Aged Unimpaired. All probe sets were considered in the statistical analysis based on the gcRMA method of data extraction from the perfect match sequences for each probe. Any probe sets having a p-value less than 0.05 were considered significantly changed and the genes or plurality of genes selected.

Microarray Results

Table 48 shows the genes that were identified as being associated with cognitive impairment in this experiment. The reference sequence transcript ID (GENBANK® number for the exemplar sequence) was used to identify genes considered significantly changed. When this exemplar ID was not available, a UniGene identifier was used in conjunction with the GENBANK® accession number.

TABLE 48

DG - AU ANOVA DECREASE
GENBANK ® ID

AI454679
AW142720
AW524426
BE098467
BF282715
NM_001001510
NM_001001719
NM_001001799
NM_001004094
NM_001004132
NM_001004238
NM_001004274
NM_001005547
NM_001007637
NM_001007721

TABLE 48-continued

DG - AU ANOVA DECREASE
GENBANK ® ID

NM_001008301
NM_001008368
NM_001008558
NM_001009631
NM_001009641
NM_001009713
NM_001010953
NM_001010961
NM_001011896
NM_001011904
NM_001011956
NM_001011978
NM_001011987
NM_001012113
NM_001012152
NM_001012175
NM_001013103
NM_001013199
NM_001017537
NM_001024747
NM_001024784
NM_001024906
NM_001025421
NM_001025753
NM_001033066
NM_001033693
NM_001034131
NM_001034198
NM_012520
NM_012533
NM_012567
NM_012582
NM_012651
NM_012656
NM_012755
NM_012756
NM_012762
NM_012775
NM_012798
NM_012829
NM_012952
NM_012968
NM_013029
NM_013080
NM_013100
NM_013106
NM_013199
NM_016991
NM_017031
NM_017033
NM_017066
NM_017195
NM_017207
NM_017213
NM_017261
NM_017305
NM_017359
NM_019129
NM_019193
NM_019306
NM_019356
NM_021577
NM_021751
NM_021763
NM_021851
NM_022193
NM_022197
NM_022209
NM_022217
NM_022249
NM_022278
NM_022288
NM_022548
NM_022589
NM_022600
NM_022675
NM_022681

TABLE 48-continued

DG - AU ANOVA DECREASE
GENBANK ® ID

NM_022858
NM_022863
NM_022936
NM_022951
NM_024000
NM_024146
NM_024158
NM_024383
NM_030836
NM_030861
NM_030862
NM_030868
NM_031007
NM_031030
NM_031034
NM_031063
NM_031132
NM_031333
NM_031351
NM_031518
NM_031594
NM_031692
NM_031701
NM_031707
NM_031831
NM_031855
NM_032613
NM_032616
NM_033359
NM_053363
NM_053375
NM_053428
NM_053438
NM_053506
NM_053601
NM_053655
NM_053854
NM_053866
NM_053973
NM_057201
NM_057205
NM_131906
NM_131907
NM_131914
NM_133560
NM_133600
NM_134336
NM_134346
NM_134367
NM_139060
NM_139113
NM_139324
NM_173126
NM_173154
NM_175758
NM_175761
NM_182842
NM_198749
NM_198764
NM_199099
NM_199256
NM_199382
NM_206950
NM_212521
NM_212532
NM_214457
XM_213433
XM_213777
XM_213779
XM_214030
XM_214400
XM_214451
XM_214522
XM_214751
XM_214775
XM_215389
XM_215416
XM_215612
XM_216047
XM_216563
XM_216725
XM_216755
XM_216784
XM_216859
XM_216964
XM_217078
XM_217367
XM_217464
XM_217732
XM_218382
XM_219374
XM_220224
XM_220753
XM_221120
XM_221369
XM_221566
XM_222568
XM_222578
XM_222868
XM_223496
XM_224350
XM_224417
XM_224732
XM_225923
XM_226014
XM_230495
XM_231148
XM_231655
XM_232640
XM_232809
XM_232941
XM_233297
XM_233955
XM_233970
XM_234156
XM_234328
XM_235164
XM_235179
XM_235338
XM_236992
XM_237179
XM_237790
XM_238127
XM_238151
XM_238177
XM_243623
XM_340884
XM_341354
XM_341612
XM_342149
XM_342174
XM_342281
XM_342396
XM_342503
XM_342533
XM_342692
XM_342900
XM_343081
XM_343114
XM_343546
XM_343588
XM_343764
XM_344135
XM_344405
XM_345867
XM_573442
XM_574644

The genes in this set show abundance of expressed gene product(s) in the Aged Unimpaired population that are significantly decreased, as determined by ANOVA, compared to those abundances in Young and Aged Impaired populations combined. Therefore, compounds useful in treating cognitive impairment selected using these genes should decrease the abundance or attenuate the function of the expressed gene products of these genes.

While this invention has been particularly shown and described with references to preferred elements thereof, it will be understood by those skilled in the art that various changes in form and details may be made therein without departing from the scope of the invention encompassed by the appended claims.

We claim:

1. A method for treating cognitive impairment in a subject in need thereof, the method comprising the step of administering to the subject a GABA-A α5 receptor agonist in an amount sufficient to beneficially alter cognitive function in said subject in an amount sufficient to beneficially alter cognitive function in said subject.

2. The method according to claim 1, wherein the subject is a human subject.

3. The method according to claim 1 or 2, wherein the agonist is selected from the group consisting of 1-methyl-7-acetyleno-5-phenyl-1,3-dihydro-benzo[e]-1,4-diazepin-2-one; 6,6 dimethyl-3-(3-hydroxypropyl)thio-1-(thiazol-2-yl)-6,7-dihydro-2-benzothiophen-4(5H)-one; and 8-ethylthio-3-methyl-5-(1-oxidopyridin-2-yl)-3,4-dihydronaphthalen-1(2H)-one.

* * * * *

UNITED STATES PATENT AND TRADEMARK OFFICE
CERTIFICATE OF CORRECTION

| | | |
|---|---|---|
| PATENT NO. | : 8,510,055 B2 | Page 1 of 1 |
| APPLICATION NO. | : 11/990049 | |
| DATED | : August 13, 2013 | |
| INVENTOR(S) | : Michela Gallagher et al. | |

It is certified that error appears in the above-identified patent and that said Letters Patent is hereby corrected as shown below:

On the Title page, item (60):

Delete the duplicate recitation of "provisional application No. 60/705,700, filed on Aug. 3, 2005, provisional application No. 60/705,698, filed on Aug. 3, 2005,".

In the Claims

In column 163, claim 1, lines 15-16:

Delete the duplicate recitation of "in an amount sufficient to beneficially alter cognitive function in said subject".

Signed and Sealed this
Twenty-sixth Day of November, 2013

Margaret A. Focarino
*Commissioner for Patents of the United States Patent and Trademark Office*